US009248184B2

(12) United States Patent
Chang et al.

(10) Patent No.: US 9,248,184 B2
(45) Date of Patent: Feb. 2, 2016

(54) DOCK-AND-LOCK (DNL) CONSTRUCTS FOR HUMAN IMMUNODEFICIENCY VIRUS (HIV) THERAPY

(71) Applicant: IBC Pharmaceuticals, Inc., Morris Plain, NJ (US)

(72) Inventors: Chien-Hsing Chang, Downingtown, PA (US); David M. Goldenberg, Mendham, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

(21) Appl. No.: 13/906,523

(22) Filed: May 31, 2013

(65) Prior Publication Data

US 2013/0280250 A1 Oct. 24, 2013

Related U.S. Application Data

(60) Division of application No. 13/288,202, filed on Nov. 3, 2011, now Pat. No. 8,481,041, and a continuation-in-part of application No. 11/745,692, (Continued)

(51) Int. Cl.
| | |
|---|---|
| A61K 39/395 | (2006.01) |
| A61K 47/48 | (2006.01) |
| A61K 39/00 | (2006.01) |
| A61K 39/42 | (2006.01) |
| A61K 39/44 | (2006.01) |
| C07K 16/10 | (2006.01) |
| C07K 16/28 | (2006.01) |

(52) U.S. Cl.
CPC ............. *A61K 39/3955* (2013.01); *A61K 39/42* (2013.01); *A61K 39/44* (2013.01); *A61K 47/48246* (2013.01); *A61K 47/48407* (2013.01); *A61K 47/48523* (2013.01); *A61K 47/48676* (2013.01); *C07K 16/1063* (2013.01); *C07K 16/2887* (2013.01); *A61K 2039/505* (2013.01); *C07K 2317/35* (2013.01); *C07K 2317/51* (2013.01); *C07K 2317/55* (2013.01); *C07K 2317/64* (2013.01); *C07K 2317/73* (2013.01); *C07K 2317/732* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,046,722 A | 9/1977 | Rowland | |
| 4,699,784 A | 10/1987 | Shih et al. | |
| 4,868,109 A | 9/1989 | Lansdorp | |
| 5,770,198 A | 6/1998 | Coller et al. | |
| 5,871,945 A | 2/1999 | Lockerbie et al. | |
| 6,261,537 B1 | 7/2001 | Klaveness | |
| 6,306,393 B1 | 10/2001 | Goldenberg et al. | |
| 6,524,854 B1 | 2/2003 | Mania et al. | |
| 6,617,135 B1 | 9/2003 | Gillies et al. | |
| 7,060,506 B2 | 6/2006 | Craig | |
| 7,151,164 B2 | 12/2006 | Hansen et al. | |
| 7,432,342 B2 | 10/2008 | Braun et al. | |
| 7,521,056 B2 | 4/2009 | Chang et al. | |
| 7,527,787 B2 | 5/2009 | Chang et al. | |
| 7,534,866 B2 | 5/2009 | Chang et al. | |
| 7,541,440 B2 | 6/2009 | Goldenberg et al. | |
| 7,550,143 B2 | 6/2009 | Chang et al. | |
| 7,591,994 B2 | 9/2009 | Govindan et al. | |
| 7,666,400 B2 | 2/2010 | Chang et al. | |
| 7,858,070 B2 | 12/2010 | Chang et al. | |
| 7,871,622 B2 | 1/2011 | Chang et al. | |
| 7,901,680 B2 | 3/2011 | Chang et al. | |
| 7,906,118 B2 | 3/2011 | Chang et al. | |
| 7,906,121 B2 | 3/2011 | Chang et al. | |
| 7,981,398 B2 | 7/2011 | Chang et al. | |
| 8,003,111 B2 | 8/2011 | Chang et al. | |
| 8,034,352 B2 | 10/2011 | Chang et al. | |
| 8,158,129 B2 | 4/2012 | Chang et al. | |
| 8,163,291 B2 | 4/2012 | Chang et al. | |
| 8,211,440 B2 | 7/2012 | Chang et al. | |
| 8,246,960 B2 | 8/2012 | Chang et al. | |
| 8,277,817 B2 | 10/2012 | Chang et al. | |

(Continued)

FOREIGN PATENT DOCUMENTS

| | | |
|---|---|---|
| WO | 9110742 | 7/1991 |
| WO | 9111198 | 8/1991 |

(Continued)

OTHER PUBLICATIONS

Zwick et al., Journal of Virology, 2005, 79(2):1252-1261.*

(Continued)

*Primary Examiner* — Nicole Kinsey White
(74) *Attorney, Agent, or Firm* — Richard A. Nakashima

(57) ABSTRACT

The present invention concerns methods and compositions for treatment of HIV infection in a subject, utilizing a DNL® complex comprising at least one anti-HIV therapeutic agent, attached to an antibody, antibody fragment or PEG. In a preferred embodiment, the antibody or fragment binds to an antigen selected from gp120, gp41, CD4 and CCR5. In a more preferred embodiment the antibody is P4/D10 or 2G12, although other anti-HIV antibodies are known and may be utilized. In a most preferred embodiment, the anti-HIV therapeutic agent is a fusion inhibitor, such as T20, T61, T651, T1249, T2635, CP32M or T-1444, although other anti-HIV therapeutic agents are known and may be utilized. The DNL® complex may be administered alone or may be co-administered with one or more additional anti-HIV therapeutic agents.

9 Claims, 21 Drawing Sheets

Related U.S. Application Data filed on May 8, 2007, now Pat. No. 8,333,971, said application No. 13/288,202 is a continuation-in-part of application No. 13/036,820, filed on Feb. 28, 2011, now Pat. No. 8,883,160, and a continuation-in-part of application No. 13/021,302, filed on Feb. 4, 2011, now Pat. No. 8,246,960, which is a division of application No. 12/417,917, filed on Apr. 3, 2009, now Pat. No. 7,906,121, which is a division of application No. 11/478,021, filed on Jun. 29, 2006, now Pat. No. 7,534,866, said application No. 13/288,202 is a continuation-in-part of application No. 12/968,936, filed on Dec. 15, 2010, now Pat. No. 8,906,377, which is a division of application No. 12/396,965, filed on Mar. 3, 2009, now Pat. No. 7,871,622, which is a division of application No. 11/391,584, filed on Mar. 28, 2006, now Pat. No. 7,521,056, said application No. 13/288,202 is a continuation-in-part of application No. 12/964,021, filed on Dec. 9, 2010, now Pat. No. 8,491,914, said application No. 13/288,202 is a continuation-in-part of application No. 12/949,536, filed on Nov. 18, 2010, now Pat. No. 8,211,440, said application No. 13/288,202 is a division of application No. 12/936,605, filed on Mar. 3, 2009, now Pat. No. 7,858,070, which is a division of application No. 11/633,729, filed on Dec. 5, 2006, now Pat. No. 7,527,787, which is a continuation-in-part of application No. 12/754,740, filed on Apr. 6, 2010, now Pat. No. 8,562,988, said application No. 13/288,202 is a continuation-in-part of application No. 12/468,589, filed on May 19, 2009, now Pat. No. 8,163,291, which is a division of application No. 11/389,358, filed on Mar. 24, 2006, now Pat. No. 7,550,143.

(60) Provisional application No. 61/409,740, filed on Nov. 3, 2010, provisional application No. 61/487,956, filed on May 19, 2011, provisional application No. 60/800,342, filed on May 15, 2006, provisional application No. 60/668,603, filed on Apr. 6, 2005, provisional application No. 60/728,292, filed on Oct. 19, 2005, provisional application No. 60/751,196, filed on Dec. 16, 2005, provisional application No. 60/782,332, filed on Mar. 14, 2006, provisional application No. 61/267,877, filed on Dec. 9, 2009, provisional application No. 61/302,682, filed on Feb. 9, 2010, provisional application No. 61/414,592, filed on Nov. 17, 2010, provisional application No. 60/864,530, filed on Nov. 6, 2006, provisional application No. 61/168,290, filed on Apr. 10, 2009.

(56) References Cited

U.S. PATENT DOCUMENTS

| | | | |
|---|---|---|---|
| 8,282,934 | B2 | 10/2012 | Chang et al. |
| 8,349,332 | B2 | 1/2013 | Chang et al. |
| 8,435,540 | B2 | 5/2013 | Chang et al. |
| 8,475,794 | B2 | 7/2013 | Chang et al. |
| 8,481,041 | B2 | 7/2013 | Chang et al. |
| 8,491,914 | B2 | 7/2013 | Chang et al. |
| 8,551,480 | B2 | 10/2013 | Chang et al. |
| 8,562,988 | B2 | 10/2013 | Chang et al. |
| 8,597,659 | B2 | 12/2013 | Chang et al. |
| 2003/0198956 | A1 | 10/2003 | Makowski et al. |
| 2003/0232420 | A1 | 12/2003 | Braun et al. |
| 2004/0018587 | A1 | 1/2004 | Makowski et al. |
| 2005/0003403 | A1 | 1/2005 | Rossi et al. |
| 2005/0175619 | A1 | 8/2005 | Duffy et al. |
| 2005/0202043 | A1 | 9/2005 | Etzerodt |
| 2006/0210475 | A1 | 9/2006 | Goldenberg et al. |
| 2006/0228300 | A1 | 10/2006 | Chang et al. |
| 2006/0228357 | A1 | 10/2006 | Chang et al. |
| 2007/0020259 | A1 | 1/2007 | Hansen et al. |
| 2007/0086942 | A1 | 4/2007 | Chang et al. |
| 2007/0140966 | A1 | 6/2007 | Chang et al. |
| 2007/0264265 | A1 | 11/2007 | Goldenberg et al. |
| 2008/0171067 | A1 | 7/2008 | Chang et al. |
| 2009/0060862 | A1 | 3/2009 | Chang et al. |
| 2009/0111143 | A1 | 4/2009 | Goldenberg et al. |
| 2009/0191225 | A1 | 7/2009 | Chang et al. |
| 2009/0202433 | A1 | 8/2009 | Chang et al. |
| 2009/0202487 | A1 | 8/2009 | Chang et al. |
| 2009/0269277 | A1 | 10/2009 | Chang et al. |
| 2009/0304580 | A1 | 12/2009 | Goldenberg et al. |
| 2010/0068137 | A1 | 3/2010 | Chang et al. |
| 2010/0104589 | A1 | 4/2010 | Govindan et al. |
| 2010/0189641 | A1 | 7/2010 | Chang et al. |
| 2010/0189689 | A1 | 7/2010 | Chang et al. |
| 2010/0196266 | A1 | 8/2010 | Goldenberg et al. |
| 2010/0204120 | A1 | 8/2010 | Jiang et al. |
| 2011/0020273 | A1 | 1/2011 | Chang et al. |
| 2011/0064754 | A1 | 3/2011 | Taylor et al. |
| 2011/0143417 | A1 | 6/2011 | Chang et al. |
| 2011/0158905 | A1 | 6/2011 | Goldenberg et al. |
| 2011/0189083 | A1 | 8/2011 | Chang et al. |
| 2012/0093769 | A1 | 4/2012 | Chang et al. |
| 2012/0196346 | A1 | 8/2012 | Chang et al. |
| 2012/0276100 | A1 | 11/2012 | Chang et al. |
| 2012/0276608 | A1 | 11/2012 | Chang et al. |
| 2013/0078183 | A1 | 3/2013 | Chang et al. |
| 2013/0109073 | A1 | 5/2013 | Chang et al. |
| 2013/0164816 | A1 | 6/2013 | Chang et al. |
| 2013/0177532 | A1 | 7/2013 | Chang et al. |
| 2013/0217091 | A1 | 8/2013 | Chang et al. |
| 2013/0295005 | A1 | 11/2013 | Chang et al. |

FOREIGN PATENT DOCUMENTS

| | | |
|---|---|---|
| WO | WO0068248 | 11/2000 |
| WO | 2006/107617 | 10/2006 |
| WO | 2006/107786 | 10/2006 |
| WO | 2007046893 | 4/2007 |
| WO | WO2007075270 | 7/2007 |
| WO | 2007127219 | 11/2007 |
| WO | 2007134037 | 11/2007 |
| WO | 2008/033413 | 3/2008 |
| WO | 2009126558 | 10/2009 |
| WO | 2010017500 | 2/2010 |

OTHER PUBLICATIONS

Bartlett, The 13th Conference on Retroviruses and Opportunistic Infections, held in Denver, Colorado, Feb. 5-8, 2006.*
Abbas et al., Cellular and Molecular Immunology, W.B. Saunders Company, 1991, p. 43.
Alto et al., "Bioinformatic design of A-kinase anchoring protein-in silico:A potent and selective peptide antagonist of type II protein kinase A anchoring", PNAS USA 100:4445-50, 2003.
Backer et al., "Self-Assembled "Dock and Lock" System for Linking Payloads to Targeting Proteins", Bioconjugate Chem., 17 (4), pp. 912-919, 2006.
Baillie et al., "Compartmentalisation of phospodiesterases and protein kinase A: opposites attract", FEBS Letters 2005; 579:3264-3270.
Banky et al., "Dimerization/Docking Domain of the Type Iα Regulatory Subunit of cAMP-dependent Protein Kinase", J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.
Belardelli et al., "Interferon-alpha in tumor immunity and immunotherapy" Cytokine Growth Factor Rev. 13(2):110-134 (2002).
Belardelli et al., "International Meeting on Cancer Vaccines: How Can We Enhance Efficacy of Therapeutic Vaccines?" Cancer Res. 64:6827-6830 (2004).

(56) References Cited

OTHER PUBLICATIONS

Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against Listeria monocytogenes" J. Exp. Med. 203(4):933-940 (2006).
Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function", Trends Cell Biol. 6:216-21 (1999).
Corbin et al., "Regulation of Adenosine 3',5'-Monophosphate-dependent Protein Kinase", J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor", Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).
Gillies et al., "High-level expression of chimeric antibodies using adapted cDNA variable region cassettes", J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting", J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site", Nat. Biotechnology Apr. 1990;8(4):343-6.

Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al. "Mutational Analysis of the A-Kinase Anchoring Protein (AKAP)-binding Site on RII", J. Biol. Chem. 271:29016-22 (1996).
Henry et al., "A prostate-specific membrane antigen-targeted monoclonal antibody-chemotherapeutic conjugate designed for the treatment of prostate cancer", Cancer Res. Nov. 1, 2004;64(21):7995-8001.
Hodneland et al., "Selective immobilization of proteins to self-assembled monolayers presenting active site-directed capture ligands", Proc. Natl. Acd. Sci. USA 2002; 99:5048-5052.
Huang et al., "Targeting IFN-α to B Cell Lymphoma by a Tumor-Specific Antibody Elicits Potent Antitumor Activities" J. Immunol. 179:6881-88 (2007).
Hundsrucker et al., "High-affinity AKAPδ-protein kinase A interaction yields novel protein kinase A-anchoring disruptor peptides" Biochem. J. (2006) 396, 297-306.
Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).
Kinderman et al., "A Dynamic Mechanism for AKAP Binding to RII Isoforms of cAMP-Dependent Protein Kinase" Mol. Cell 24(3):397-408 (2006).
Kinstler et al., "Characterization and Stability of N-terminally PEGylated rhG-CSF" Pharm. Res. 1996;13(7):996-1002.
Kramer et al., "Cell and virus sensitivity studies with recombinant human alpha interferons" J. Interferon. Res. 3(4):425-35 (1983).
Le Bon et al., "Type I Interferons Potently Enhance Humoral Immunity and Can Promote Isotype Switching by Stimulating Dendritic Cells in Vivo" Immunity 14:461-470 (2001).
Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.
Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).
Luft et al., "Type I IFNs Enhance the Terminal Differentiation of Dendritic Cells" J. Immunol. 161:1947-1953 (1998).
Mason, Anthony J., "Functional Analysis of the Cysteine Residues of Activin A", Mol. Endocrinol. 8:325-32, 1994.
Cardillo et al., "Targeting both IGF-1R and mTOR synergistically inhibits growth of renal cell carcinoma in vitro", BMC Cancer. Apr. 1, 2013;13:170.
Chang et al., "A new method to produce monoPEGylated dimeric cytokines shown with human interferon-α2b", Bioconjug Chem. Oct. 21, 2009;20(10):1899-907.
Chang et al., "Evaluation of a novel hexavalent humanized anti-IGF-1R antibody and its bivalent parental IgG in diverse cancer cell lines", PLoS One. 2012;7(8):e44235.
Goldenberg et al., "Cancer Imaging and Therapy with Bispecific Antibody Pretargeting", Update Cancer Ther. Mar. 2, 2007(1):19-31.
Govindan et al., "Designing immunoconjugates for cancer therapy", Expert Opin Biol Ther. Jul. 2012;12(7):873-90.
Liu et al., "Trop-2-targeting tetrakis-ranpirnase has potent antitumor activity against triple-negative breast cancer", Mol Cancer Mar. 10, 2014;13:53.

(56) References Cited

OTHER PUBLICATIONS

Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rossi et al., "The dock-and-lock method combines recombinant engineering with site-specific covalent conjugation to generate multifunctional structures", Bioconjug Chem. Mar. 21, 2012;23(3):309-23.
Rossi et al., "Complex and defined biostructures with the dock-and-lock method", Trends Pharmacol Sci. Sep. 2012;33(9):474-81.
Rossi et al. "Optimization of multivalent bispecific antibodies and immunocytokines with improved in vivo properties", Bioconjug Chem. Jan. 16, 2013;24(1):63-71.
Rossi et al., "A new class of bispecific antibodies to redirect T cells for cancer immunotherapy", MAbs. Mar.-Apr. 2014; 6(2):381-91.
Sharkey et al., "Improved cancer therapy and molecular imaging with multivalent, multispecific antibodies", Cancer Biother Radiopharm. Feb. 2010;25(1):1-12.
Matarrese et al., "Type I Interferon Gene Transfer Sensitizes Melanoma Cells to Apoptosis via a Target Activity on Mitochondrial Function" Am. J. Pathol. 2002, 160(4):1507-1520.
Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.
Newlon et al., "A Novel Mechanism of PKA Anchoring Revealed by Solution Structures of Anchoring Complexes", EMBO J. 2001; 20:1651-1662.
Newlon et al., "The molecular basis for protein kinase A anchoring revealed by solution NMR", Nature Struct. Biol. 1999; 3:222-227.
Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.
Nordstrom et al., "First Bispecific Antibody Immunocytokine (Anti-CD20/HLA-DR-Interferon-α2b) is Highly Toxic for Human Lymphoma Cells in Vitro", 2009 ASH Annual Meeting Abstracts, Nov. 20, 2009; 114(22):675, Abstract #1695.
Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).
Oyen et al., "Human testis cDNA for the regulatory subunit RIIα of cAMP-dependent protein kinase encodes an alternate amino-terminal region", FEBS Letters 246:57-64, 1989.
Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48:135-147 (1998).
Paquette et al., "Interferon-α and granulocyte-macrophage colony-stimulating factor differentiate peripheral blood monocytes into potent antigen-presenting cells" J. Leukoc. Biol. 64:358-367; 1998.
Pelham et al., "Interferon-α conjugation to human osteogenic sarcoma monoclonal antibody 791T/36" Cancer Immunol. Immuother 1983;15(3):210-216.
Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.
Pilling et al., "Interferon-β mediates stromal cell rescue of T cells from apoptosis" Eur. J. Immunol. 29:1041-1050 (1999).
Rabjohn et al., "Molecular Cloning and Epitope Analysis of the Peanut Allergen Ara h 3" J. Clinical Investigation 103(4):535-542 (1999).
Raefsky et al., "Studies of Interferon as a regulator of hematopoietic cells proliferation" J. Immunol. 135 (4):2507-2512 (1985).
Riemer et al., "Matching of trastuzumab (Herceptin) epitope mimics onto the surface of Her-2/neu—a new method of epitope definition", Mol Immunol. May 2005;42(9):1121-4.
Rose et al., "Structural basis of dimerization, coactivator recognition and MODY3 mutations in HNF-1α", Nature Struct. Biol. 2000; 7:744-748.

Rosendahl et al., "A Long-Acting, Highly Potent Interferon α-2 Conjugate Created Using Site-Specific PEGylation" Bioconjugate Chem. 2005;16:200-207.
Rossi et al., "Novel Designs of Multivalent Anti-CD20 Humanized Antibodies as Improved Lymphoma Therapeutics", Cancer Res. 68:8384-92, 2008.
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rossi et al., "CD20-targeted tetrameric interferon-α, a novel and potent immunocytokine for the therapy of B-cell lymphomas", Blood 2009;114:3864-3871.
Rossi et al., "A veltuzumab-IFNα2b conjugate with potent in vitro and in vivo anti-lymphoma activity", Proceedings of the American Association for Cancer Research, Apr. 2009;50:783-784, Abstract #3237.
Rustandi et al., "The Ca2+–Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.
Salles et al., "Rituximab combined with chemotherapy and interferon in follicular lymphoma patients: results of the GELA-GOELAMS FL2000 study" Blood 2008; 112:4824-4831.
Santini et al., "Type I Interferon as a Powerful Adjuvant for Monocyte-derived Dendritic Cell Development and Activity In Vivo and in Hu-PBL-SCID Mice" J. Exp. Med. 191(10):1777-1788 (2000).
Scott et al., "Type II Regulatory Subunit Dimerization Determines the Subcellular Localization of the cAMP-dependent Protein Kinase", J. Biol. Chem. 265:21561-66 (1990).
Scott et al., "Cyclic nucleotide-dependent protein kinases" Pharmacol. Ther. 1991;50(1):123-45.
Seffernick et al., "Melamine Deaminase and Atrazine Chlorohydrolase: 98 Percent Identical but Functionally Different" J. Bacteriol. 183(8):2405-2410 (2001).
Sharkey et al., "Improved Therapeutic Results by Pretargeted Radioimmunotherapy of Non—Hodgkin's Lymphoma with a New Recombinant, Trivalent, Anti-CD20, Bispecific Antibody", Cancer Res. 68:5282-90, 2008.
Sharkey et al., "Metastatic Human Colonic Carcinoma: Molecular Imaging with Pretargeted SPECT and PET in a Mouse Model", Radiology 246:497-507, 2008.
Sidky et al., "Inhibition of Angiogenesis by Interferons: Effects on Tumor- and Lymphocyte-induced Vascular Responses" Cancer Res. 47:5155-5161, Oct. 1, 1987.
Stancovski et al., "Mechanistic aspects of the opposing effects of monoclonal antibodies to the ERBB2 receptor on tumor growth", Proc Natl Acad Sci U S A. Oct. 1, 1991;88(19):8691-5.
Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.
Stein et al., "Characterization of a humanized IgG4 anti—HLA-DR monoclonal antibody that lacks effector cell functions but retains direct antilymphoma activity and increases the potency of rituximab" Blood 2006;108:2736-2744.
Stokka et al., "Characterization of A-kinase-anchoring disruption using a solution-based assay" Biochem. J. (2006) 400, 493-499.
Stryer et al., "Levels of Structure in Protein Architecture", Biochemistry, 3rd Ed., pp. 31-33, W.H. Freeman & Co., New York, 1988.
Takaoka et al., "Integration of interferon-α/β signalling to p53 responses in tumour suppression and antiviral defence" Nature Jul. 31, 2003;424(6948):516-23.
Taylor, S., "cAMP-dependent Protein Kinase" J. Biol. Chem. 1989;264(15):8443-8446.
Tol et al. "Chemotherapy, bevacizumab, and cetuximab in metastatic colorectal cancer", N Engl J Med. Feb. 5, 2009;360(6):563-72.

(56) References Cited

OTHER PUBLICATIONS

Walsh et al., "An Adenosine 3′, 5′-Monophosphate-dependant Protein Kinase from Rabbit Skeletal Muscle" J. Biol. Chem. 243(13):3763-3774 (1968).
Weck et al., "Comparison of the Antiviral Activities of Various Cloned Human Interferon-α Subtypes in Mammalian Cell Cultures" J. Gen. Virol. (1981), 57, 233-237.
Winkler et al., "Changing the Antigen Binding Specificity by Single Point Mutations of an Anti-p24 (HIV-1) Antibody", J. Immunol. 165:4505-14, 2000.
Witkowski et al., "Conversion of a β-Ketoacyl Synthase to a Malonyl Decarboxylase by Replacement of the Active-Site Cysteine with Glutamine" Biochemistry 38(36):11643-50 (1999).
Wong et al., "AKAP Signalling Complexes: Focal Points in Space and Time", Nat. Rev. Mol. Cell Biol. 12:959-70 (2004).
Zhu et al., "Inhibition of tumor growth and metastasis by targeting tumor-associated angiogenesis with antagonists to the receptors of vascular endothelial growth factor", Invest. New Drugs 17:195-212, 1999.
Armbruster et al., "Passive immunization with the anti-HIV-1 human monoclonal antibody (hMAb) 4E10 and the hMAb combination 4E10/2F5/2G12", J Antimicrob Chemother. Nov. 2004;54(5):915-20.
Backstrom et al., "Characterization of an internal permissive site in the cholera toxin B-subunit and insertion of epitopes from human immunodeficiency virus-1, hepatitis B virus and enterotoxigenic *Escherichia coli*", Gene. Nov. 20, 1995;165(2):163-71.
Bergamini et al., "Adriamycin selectively inhibits HIV replication in resting macrophages", Int Conf AIDS. Jun. 16-21, 1991;7(2):109 (abstract no. W.A.1071).
Berry et al., "Structure of an anti-HIV monoclonal Fab antibody fragment specific to a gp120 C-4 region peptide", Proteins. Nov. 15, 2001;45(3):281-2.
Broliden et al., "A monoclonal antibody to human immunodeficiency virus type 1 which mediates cellular cytotoxicity and neutralization", J Virol. Feb. 1990;64(2):936-40.
Bryson et al., "Cross-netralizing human monoclonal Anti-HIV-1 antibody 2F5: preparation and crystallographic analysis of the free and epitope-complexed forms of its Fab' fragment", Protein and Peptide Letter, 8(5):413-428 (2001).
Dervillez et al., "Stable expression of soluble therapeutic peptides in eukaryotic cells by multimerisation: application to the HIV-1 fusion inhibitory peptide C46", ChemMedChem. Mar. 2006;1(3):330-9.
Eck et al., "Gene-Based Therapy", The Pharmacological Bases of Therapeutics, Goodman and Gilman, Eds., pp. 77-101 (1996).
Heath et al., "Aggresomes resemble sites specialized for virus assembly", J Cell Biol. Apr. 30, 2001;153(3):449-55.
Herberg et al., "Analysis of A-kinase anchoring protein (AKAP) interaction with protein kinase a (PKA) regulatory subunits: PKA isoform specificity in AKAP binding", J Mol Biol. Apr. 28, 2000;298(2):329-39.
Johansson et al., "Elimination of HIV-1 infection by treatment with a doxorubicin-conjugated anti-envelope antibody", AIDS. Oct. 3, 2006;20(15):1911-5.
Johnston et al., "Aggresomes: a cellular response to misfolded proteins", J Cell Biol. Dec. 28, 1998;143(7):1883-98.
Liu et al., "Different from the HIV fusion inhibitor C34, the anti-HIV drug Fuzeon (T-20) inhibits HIV-1 entry by targeting multiple sites in gp41 and gp120", J Biol Chem. Mar. 25, 2005;280(12):11259-73.
Orkin et al., Report and recommendation of the panel to assess the HIH investment in research on gene therapy, HIH, 1995.
Paulik et al., "Drug-antibody conjugates with anti-HIV activity", Biochem Pharmacol. Dec. 1, 1999;58(11):1781-90.
Sato K, "Integration of cell experiment system", KAST Annual Research Report, 2003, Abstract only.
Schonning et al. "Rapid selection for an N-linked oligosaccharide by monoclonal antibodies directed against the V3 loop of human immunodeficiency virus type 1", J Gen Virol. Apr. 1996;77 ( Pt 4):753-8.
Tozser, J., "HIV inhibitors: problems and reality", Ann NY Acad Sci. Nov. 2001;946:145-59.
Veiga et al., "An insight on the leading HIV entry inhibitors", Recent Pat Antiinfect Drug Discov. Jan. 2006;1(1):67-73.
Verma et al., "Gene therapy—promises, problems and prospects", Nature. Sep. 18, 1997;389(6648):239-42.
Wileman et al., "Aggresomes and autophagy generate sites for virus replication", Science.May 12, 2006;312 (5775):875-8.
Chang et al., "A novel class of anti-HIV agents with multiple copies of enfuvirtide enhances inhibition of viral replication and cellular transmission in vitro", PLoS One. 2012;7(7):e41235.
Song et al., "Antibody mediated in vivo delivery of small interfering RNAs via cell-surface receptors", Nat Biotechnol. Jun. 2005;23(6):709-17.

* cited by examiner

*FIG. 1*
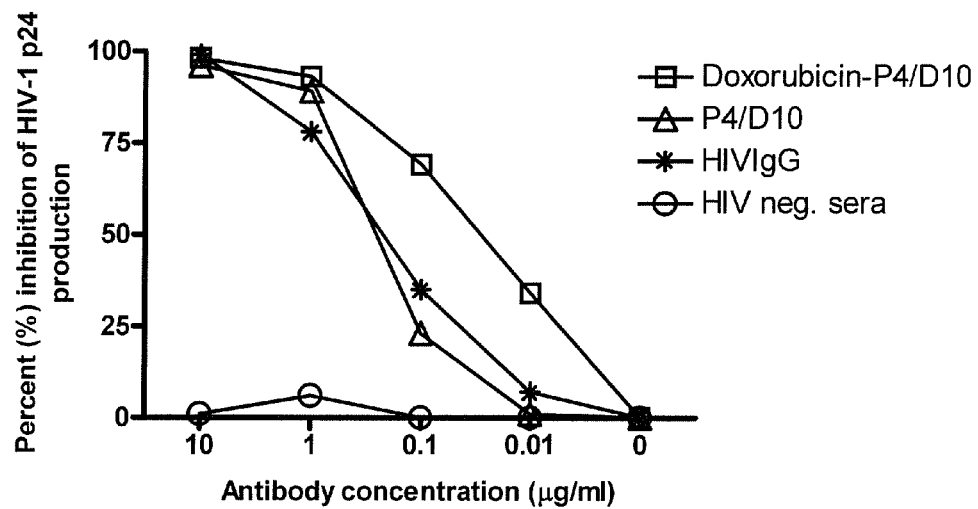
(A)
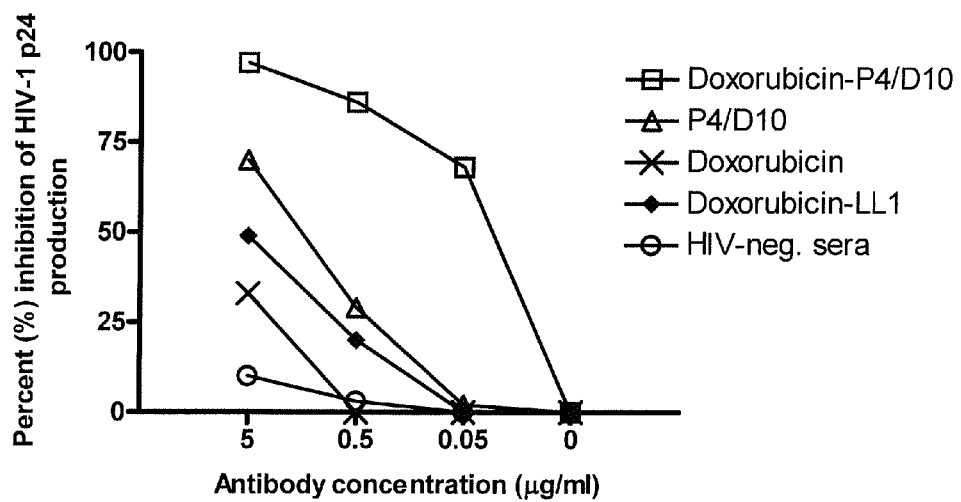
(B)

FIG. 8

(A) $V_K$ sequence of P4/D10

DIQLTQSPASLAVSLGQRATISCR<u>ASESVDDYGISFMH</u>WYQQKLGQPPKLLIY<u>RASNLES</u>GIPARFSGSGSGTEFTLTINPVETDDVATYYC<u>QQSNKDPLT</u>FGAGTKLQIKR (B) $V_H$ sequence of P4/D10

VQLQESGAELASPGASVTLSCKASGYTFT<u>DHIMNW</u>KKRPGQGLEWIG<u>RIFPVSGETNYNQKFMG</u>KATFSVDSSSTVSMVLNSLTSEDPAVYYC<u>DLIYYDYEEDYYFD</u>WGQGTTLTVSS

FIG. 9

(A) cP4/D10-VK DNA SEQUENCE

GACATCCAGCTCACCCAGTCCCCAGCCTCTCTGGCTGTGTCCCTGGACAGAGGGCCACAATCTCTTGCAGAG
CTAGCGAGTCCGTGGACGATTACGGGATTAGTTTCATGCACTGGTATCAGCAGAAGCCAGAAGCTGGGCCAGCCCCTAA
ACTGCTGATCTACCGGGCCAGTAACCTGGAAAGCGGCATTCCAGCTCGCTTCTCTGGCAGTGGAAGCGGGACC
GAGTTTACCCTGACAATCAACCCCGTGGAAACTGACGATGTGGCCACCTACTATTGTCAGCAGAGCAACAAGG
ACCCCCTGACATTTGGCGCTGGAACTAAGCTGCAGATCAAGAGG

(B) cP4/D10-VK PROTEIN SEQUENCE

DIQLTQSPASLAVSLGQRATISCRASESVDDYGISFMHWYQQKLGQPPKLLIYRASNLESGIPARFSGSGSGTEFTLTI
NPVETDDVATYYCQQSNKDPLTFGAGTKLQIKR

(C) cP4/D10-V$_H$ DNA SEQUENCE

GTGCAGCTCCAGGAGTCCGGAGCCGAACTGGCTAGTCCAGGGGCCCAGGCGTGACACTGTCCTGCAAGGCTTCT
GGGTACACTTTCACCGATCACATCATGAACTGGGTGAAGAAAGCCAGGACCAGGACTGGGAGTGGATCGGA
AGAATTTTCCCTGTGTCTGGAGAAACTAATCAGAAGTTCATGGGAAAAGCCACCTTCAGCGTGGACA
GGAGCTCCTCTACTGTGACCAGGCATGGTGCTGAACAGCCTGAGGACCCCGTGTACTATTGTGACCT
GATCTACTATGACTACGAGGAAGATTACTATTTCGACTATTTGGGGGGCAGGGCACCACACTGACAGTGAGTAG
C

(D) cP4/D10-V$_H$ PROTEIN SEQUENCE

VQLQESGAELASPGASVTLSCKASGYTFTDHIMNWVKKRPGQGLEWIGRIFPVSGETNYNQKFMGKATFSVDRSSS
TVSMVLNSLTSEDPAVYYCDLIYYDYEEDYYFDYWGQGTTLTVSS

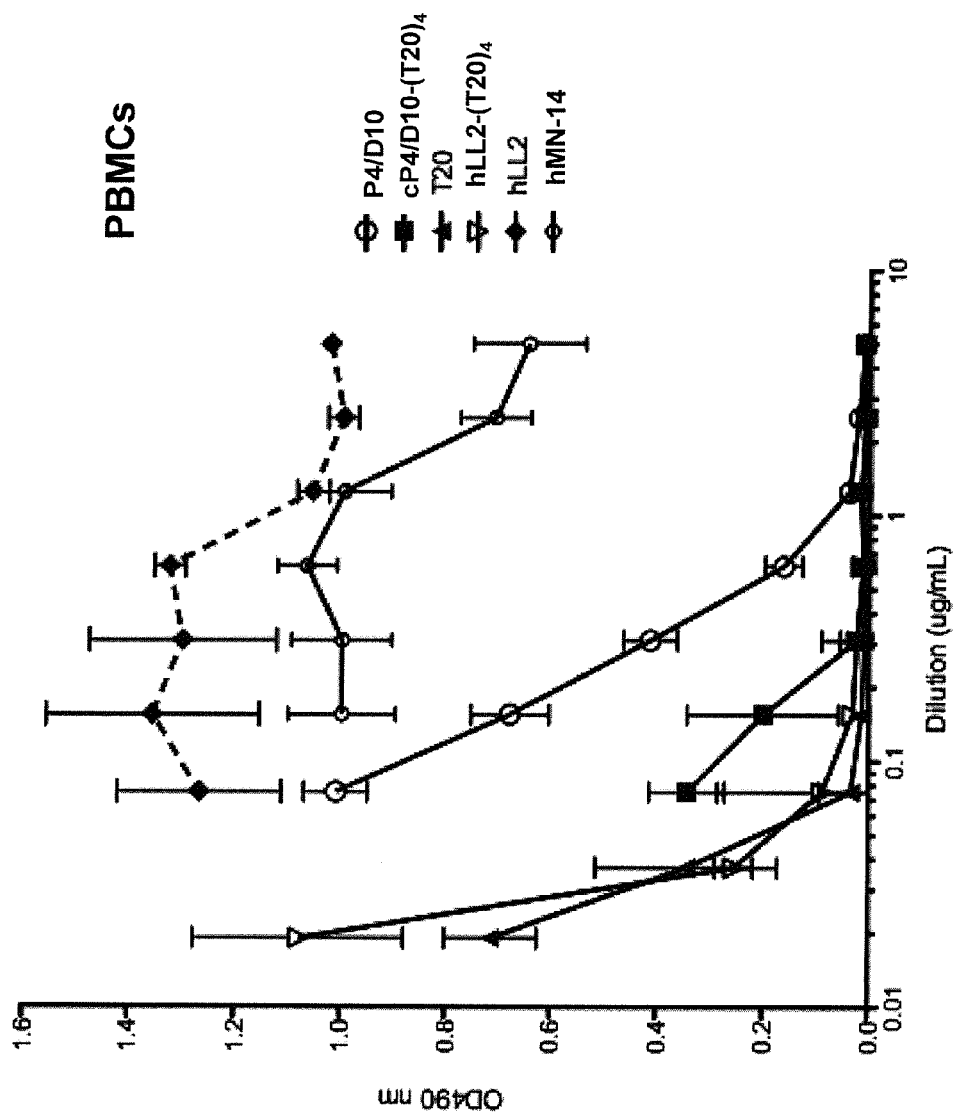

DOCK-AND-LOCK (DNL) CONSTRUCTS FOR HUMAN IMMUNODEFICIENCY VIRUS (HIV) THERAPY

RELATED APPLICATIONS

This application claims the benefit under 35 C.F.R. §119(e) to provisional application Ser. Nos. 61/409,740, filed Nov. 3, 2010, and 61/487,956, filed May 19, 2011. This application is a continuation-in-part of U.S. patent application Ser. No. 11/745,692, filed May 8, 2007, which claimed the benefit under 35 C.F.R. §119(e) to provisional application Ser. No. 60/800,342, filed May 15, 2006. This application is a continuation-in-part of U.S. patent application Ser. No. 13/036,820, filed Feb. 28, 2011; Ser. No. 13/021,302, filed Feb. 4, 2011, (which was a divisional of U.S. Pat. No. 7,906,121, which was a divisional of U.S. Pat. No. 7,534,866); Ser. No. 12/968,936, filed Dec. 15, 2010, (which was a divisional of U.S. Pat. No. 7,871,622; which was a divisional of U.S. Pat. No. 7,521,056); Ser. No. 12/964,021, filed Dec. 9, 2010; Ser. No. 12/949,536, filed Nov. 18, 2010 (which was a divisional U.S. Pat. No. 7,858,070, which was a divisional U.S. Pat. No. 7,527,787); Ser. No. 12/754,740, filed Apr. 6, 2010; and Ser. No. 12/468,589, filed May 19, 2009, (which was a divisional of U.S. Pat. No. 7,550,143). Those applications claimed the benefit under 35 C.F.R. §119(e) to provisional application Ser. Nos. 61/414,592, filed Nov. 17, 2010; 61/302,682, filed Feb. 9, 2010; 61/267,877, filed Dec. 9, 2009; 61/168,290, filed Apr. 10, 2009; 60/864,530, filed Nov. 6, 2006; 60/782,332, filed Mar. 14, 2006; 60/751,196, filed Dec. 16, 2005; 60/728,292, filed Oct. 19, 2005; and 60/668,603, filed Apr. 6, 2005. The text of each priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Nov. 11, 2011, is named IBC129WO.txt and is 48,601 bytes in size.

BACKGROUND

1. Field of the Invention

The present invention concerns methods and compositions for treating human immunodeficiency virus (HIV) in infected subjects. Preferably, the methods and compositions utilize complexes made by the DOCK-AND-LOCK® (DNL®) technique. In particular embodiments, the DNL® complexes comprise antibodies or antibody fragments against HIV envelope antigens, for example anti-gp120 or anti-gp41 antibodies such as P4/D10, 2G12, 2F5 or 4E10. In more particular embodiments, the DNL® complex may comprise one or more agents, such as therapeutic agents, diagnostic agents, virostatic agents and/or cytotoxic agents, including but not limited to chemotherapeutic agents such as doxorubicin. Such agents may be incorporated into the DNL® complex using the DDD (docking and dimerization domain) and AD (anchoring domain) binding interaction described below, or may be directly conjugated to another component of the DNL® complex, such as an anti-HIV antibody or antibody fragment. More preferably, the DNL® complex may comprise one or more agents known to have anti-HIV activity, such as the T20 (enfuvirtide) HIV fusion inhibitor. Most preferably, incorporation of anti-HIV agents into a DNL® complex improves the pharmacokinetic properties of the agent, for example by increasing its serum half-life, allowing less frequent dosing and/or improved efficacy. In alternative embodiments, the DNL® complex may comprise one or more polyethylene glycol (PEG) moieties to provide improved pharmacokinetics. The DNL® complexes may be used alone or in combination with one or more known anti-HIV agents.

2. Description of Related Art

Despite encouraging advances in the treatment of human immunodeficiency virus-1 (HIV-1) with anti-retroviral therapy (ART), analyses of peripheral blood and lymph nodes have documented the presence of persistent reservoirs of resting T cells which harbor latent provirus that can activate spontaneously even years after the termination of therapy (Berger et al., *Proc Natl Acad Sci USA* 1998, 95:11511-11513; Blankson et al., *Annu Rev Med* 2002, 53:557-593).

Binding and neutralizing antibodies can prevent attachment of free virus to the cellular receptor, they can bind to the viral surface, and they can induce complement-mediated virolysis of free virions (Parren et al., *AIDS* 1999, 13[Suppl A]:S137-162). Antibodies may also mediate killing of infected cells by antibody-dependent cellular cytotoxicity (ADCC), by coupling NK-cells to infected target cells (Broliden et al., *J Virol* 1990, 64:936-940). However, the use of anti-viral antibodies alone as part of an immunotherapy of patients infected with HIV has not fulfilled its initial promise (Hinkula et al., *J Acquir Immune Defic Syndr* 1994, 7:940-951; Trkola et al., *Nat Med* 2005, 11:615-622).

Attempts have been made to use various viral or cellular components as targets for antibody delivery of therapeutic agents to HIV-infected cells (Davey et al., *J Infect Dis* 1994, 170:1180-1188; Pincus et al., *J Immunol* 2003, 170:2236-2241; Ramachandran et al., *J Infect Dis* 1994, 170:1009-1013; Saavedra-Lozano et al., *Proc Natl Acad Sci USA* 2004, 101:2494-2499). Similar immunotoxins have proved promising in cancer patients (Wu and Senter, *Nat Biotechnol* 2005, 23:1137-1146). However, a need exists for more effective methods and compositions for treatment of HIV-infected cells.

SUMMARY OF THE INVENTION

The present invention fulfills an unresolved need in the art by providing methods and compositions for inhibiting, suppressing, detecting, identifying, localizing and/or eliminating HIV and/or HIV-infected cells. In certain embodiments, the compositions and methods may utilize DNL® complexes comprising antibodies, antibody fragments or other targeting molecules that bind to HIV antigens. HIV-binding molecules may include, but are not limited to, affibodies, monoclonal antibodies, humanized antibodies, chimeric antibodies, human antibodies, antibody fragments and/or antibody analogs. Any anti-HIV antibody or antigen-binding fragment thereof known in the art may be incorporated into the subject DNL® complexes, including but not limited to P4/D10, 2G12, 2F5 or 4E10.

In certain embodiments, the HIV targeting molecules may be conjugated to one or more therapeutic and/or diagnostic agents. Such agents may include, but are not limited to, a drug, prodrug, virostatic agent, toxin, enzyme, oligonucleotide, radioisotope, radionuclide, immunomodulator, cytokine, label, fluorescent label, luminescent label, paramagnetic label, MRI label, micelle, liposome, nanoparticle, or combination thereof. In alternative embodiments, the HIV targeting molecules may be attached to therapeutic agents via the DNL® technology described below.

The DNL® complexes may be administered to patients with a known or suspected HIV infection. Administration may be by any route known in the art, such as orthotopic, intradermal, intramuscular, subcutaneous, intraperitoneal, intraarterial, intrathecal or intravenous injection. Alternatively, administration may be oral, nasal, buccal, inhalational, rectal, vaginal or topical. Such administration may block or prevent infection of cells with HIV, may reduce or eliminate HIV-infected cells in the patient, and/or may reduce or eliminate residual foci of HIV-infected cells in patients treated previously and/or simultaneously with other known anti-retroviral therapies.

The skilled artisan will realize that the subject DNL® complexes may be administered either alone or in combination with other known therapeutic treatments for HIV infection, such as azidothymidine, other nucleoside/nucleotide reverse transcriptase inhibitors, non-nucleoside reverse transcriptase inhibitors, HIV protease inhibitors and/or fusion inhibitors. In certain embodiments, the conjugated HIV targeting molecules may be used in combination with HAART (highly active anti-retroviral therapy). Many anti-HIV therapeutic agents are known in the art and any such known agent may be used, including but not limited to abacavir, amdoxovir, apricitabine, atazanavir, bevirimat, calanolide A, CCR5, CD4, ceragenin, cobicistat, cyanovirin-N, darunavir, diarylpyrimidines, didanosine, dolutegravir, efavirenz, elvitegravir, elvucitabine, emtricitabine, epigallotachen gallate, festinavir, fosamprenavir, foscarnet, griffithsin, globoidnan A, hydroxycarbamide, indinavir, KP-146, lamivudine, lefinavir, lersivirine, lopinavir, miltefosine, MK-2048, nelfinavir, nevirapine, racivir, raltegravir, ritonavir, saquinavir, selicicib, stafudine, stampidine, stavudine, Tat antagonists, tenofovir, tipranavir, trichosanthin, TRIM5alpha, vivecon, zalcitabine, zidovudine or zidovudine, either alone or in any combination.

The subject DNL® complexes may comprise an anti-HIV antibody or antigen-binding fragment thereof attached to multiple copies of a toxin, such as a bacterial toxin, a plant toxin, ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, *Pseudomonas* endotoxin, ranpirnase (Rap) or Rap (N69Q). More preferably, the DNL® conjugated toxin is cytotoxic at nanomolar or lower concentrations.

Yet another embodiment relates to DNL® complexes for delivery of therapeutic nucleic acid species, such as artificial genes or siRNA. In such embodiments, the DNL® complex may comprise an anti-HIV antibody or fragment thereof attached to one or more copies of a nucleic acid carrier, such as a dendrimer, a protamine, a histone, histidine-containing reducible polycation, cationic comb-type copolymer, chitosan-thiamine pyrophosphate, polyethyleneimine or polylysine. Many examples of nucleic acid binding polymers are known in the art, such as PAMAM, polylysine, polypropyleneimine, polyethyleneimine, polyethyleneglycol or carbosilane. Generally, the carrier molecule is polycationic and binds to nucleic acids by electrostatic interaction. As discussed below, many examples of siRNA or other therapeutic nucleic acids are known in the art and any such known species may be delivered to a target cell, tissue, organ or pathogen using the DNL® complexes described herein.

The subject (DNL®) complexes comprise at least two copies of a dimerization and docking domain (DDD) moiety and at least one copy of an anchoring domain (AD) moiety. Preferably, the DDD moiety is from a human protein kinase A regulatory subunit protein (RIα, RIβ, RIIα, RIIβ) while the AD moiety is from an AKAP (A-kinase anchoring protein). The DDD moieties spontaneously form dimers which then bind to the AD moiety to form the DNL® complex. The DNL® complexes may comprise fusion proteins incorporating the AD and DDD moieties, although alternatively the AD and/or DDD moieties may be covalently attached to effector moieties by other methods, such as chemical coupling. Effectors incorporated into the DNL® complex may include, but are not limited to, proteins, peptides, antibodies, antibody fragments, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule known to produce physiological effects. The subject DNL® complexes may be comprised of dimers, trimers, tetramers, pentamers, hexamers or other multimers. The skilled artisan will realize that the DNL® technology allows the efficient and reproducible formation of multimeric complexes comprising virtually any combination of effector subunits.

Also described herein are isolated nucleic acids encoding a fusion protein or other DNL® subunit, as described herein. Other embodiments concern expression vectors and/or host cells comprising the encoding nucleic acid sequences. In certain preferred embodiments, the host cell may be an Sp2/0 cell line transformed with a mutant Bcl-2 gene, for example with a triple mutant Bcl-2 gene (T69E, S70E, S87E), that has been adapted to cell transformation and growth in serum free medium. (See, e.g., U.S. Pat. Nos. 7,531,327; 7,537,930; and 7,608,425, the Examples section of each of which is incorporated herein by reference.) The host cell transfected with expression vector(s) encoding a DNL® complex, or a subunit of a DNL® complex, may be cultured by standard techniques for production of the encoded protein or complex. Advantageously, the host cell is adapted for growth and protein production under serum-free conditions.

The skilled artisan will realize that the DNL® complexes and uses thereof disclosed above are exemplary only and that many other different types of DNL® complexes, for either therapeutic or diagnostic use, are included within the scope of the present invention.

BRIEF DESCRIPTION OF THE DRAWINGS

The following drawings form part of the present specification and are included to further demonstrate certain aspects of particular embodiments of the invention. The embodiments may be better understood by reference to one or more of these drawings in combination with the detailed description presented herein.

FIG. 1A. HIV-$1_{IIIB}$ neutralization of HIV infection in vitro. The neutralizing capacities of the immunoglobulins were tested by incubating different concentrations of the immunoglobulins with HIV-$1_{IIIB}$ and then assaying the viral infection of HIV susceptible Jurkat T-cells. Both 10 µg/ml doxorubicin-P4/D10 and unlabelled P4/D10 neutralized HIV-$1_{IIIB}$ significantly better than HIV negative sera (p=0.001).

FIG. 1B. HIV-$1_{IIIB}$ inhibition of intercellular spread of HIV infection in vitro. To test whether the immunoglobulins could limit the intercellular spread of HIV-1 infection Jurkat T-cells were mixed in the proportions 0.2%, 1%, 3%, and 5% infected and 99.8%, 99%, 97%, and 95% uninfected cells. The HIV-1 p24 production after treating 3% Jurkat T-cells infected with HIV-$1_{IIIB}$ and 97% uninfected cells with different concentrations of immunoglobulins is shown. The results are shown as percent inhibition of p24 production after 7 days in culture. Doxorubicin-P4/D10 had a significantly better inhibiting effect on production of HIV-1 p24 compared to unlabelled P4/D10, control antibody doxorubicin-LL1, free doxorubicin and HIV-negative serum at a concentration of 0.5 or 0.05 µg/ml (p=0.002).

FIG. 8. Structure of antibody-T20 DNL® complex. Schematic diagram showing AD2-antibody and DDD2-T20 fusion proteins combining to form a DNL® complex.

FIG. 9. In vitro efficacies of T20 compounds on HIV-1 6920 infected PBMC. The Y-axis values are P24 antigen concentration (as measured by ELISA) indicating viral replication in vitro in PBMC. The X-axis shows concentration of T20 compound in µg/ml.

DESCRIPTION OF ILLUSTRATIVE EMBODIMENTS

Figure 2:
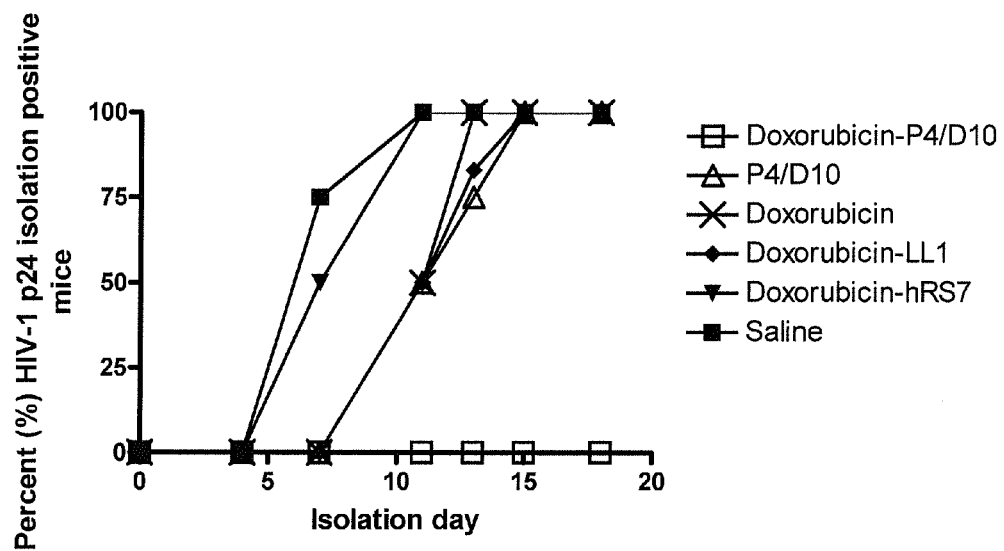
FIG. 2. Protection against HIV-1/MuLV infection in vivo. Mice (6-12/group) were challenged i.p. with HIV-1/MuLV infected splenocytes and immediately treated with monoclonal antibodies (MAb) or free doxorubicin. Unconjugated P4/D10 MAb was titrated 100-800 µg per mouse, free doxorubicin 100-400 µg and irrelevant doxorubicin-hRS7 100-200 µg. All other treatments were given at 100 µg per mouse. Ten days after challenge, peritoneal cells were collected and mixed with HIV susceptible Jurkat T-cells. HIV p24 production in these cell cultures was measured every 3-4 days for 18 days. Percent of mice with a p24 positive cell culture after treatment with 100 µg of MAb or free doxorubicin is shown. Only cells from mice treated with 100 µg doxorubicin-P4/D10 contained no infectious HIV, which was significantly different (p=0.0001) from all other groups.

All documents, or portions of documents, cited in this application, including but not limited to patents, patent applications, articles, books, and treatises, are hereby expressly incorporated by reference in their entirety.

Definitions

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would be mean any number between 90 and 110.

An "antibody", as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion or analog of an immunoglobulin molecule, like an antibody fragment.

An "antibody fragment" is a portion of an antibody such as $F(ab)_2$, $F(ab')_2$, Fab, Fv, sFv, and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition (CDR) units consisting of the amino acid residues that mimic the hypervariable region.

A "therapeutic agent" is an atom, molecule, or compound that is useful in the treatment of a disease. Examples of therapeutic agents include antibodies, antibody fragments, drugs, virostatic agents, toxins, enzymes, nucleases, hormones, immunomodulators, antisense oligonucleotides, small interfering RNA (siRNA), chelators, boron compounds, photoactive agents, dyes, and radioisotopes. Other exemplary therapeutic agents and methods of use are disclosed in U.S. Patent Application Publication Nos. 20050002945, 20040018557, 20030148409 and 20050014207, each incorporated herein by reference.

A "neutralizing antibody" or "neutralizing antibody fragment" is used herein to refer to an antibody or fragment that reacts with an infectious agent (such as a virus) and destroys or inhibits its infectivity and/or virulence.

A "diagnostic agent" is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An "immunoconjugate" is a conjugate of a binding molecule (e.g., an antibody component) with an atom, molecule, or a higher-ordered structure (e.g., with a carrier, a therapeutic agent, or a diagnostic agent).

A "naked antibody" is an antibody that is not conjugated to any other agent.

A "carrier" is an atom, molecule, or higher-ordered structure that is capable of associating with a therapeutic or diagnostic agent to facilitate delivery of such agent to a targeted cell. Carriers may include lipids (e.g., amphiphilic lipids that are capable of forming higher-ordered structures), polysaccharides (such as dextran), proteins, peptides, peptide analogs, peptide derivatives or other higher-ordered structures, such as micelles, liposomes, or nanoparticles. In certain embodiments, a carrier may be designed to be resistant to proteolytic or other enzymatic degradation, for example by substituting D-amino acids for naturally occurring L-amino acids in a protein or peptide.

As used herein, the term "antibody fusion protein" refers to a recombinantly produced antigen-binding molecule in which two or more of the same or different scFv or antibody fragments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds to one such epitope, for example a diabody with two binding site reactive with the same antigen. The fusion protein may comprise a single antibody component, a multivalent or multispecific combination of different antibody components, or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

An antibody or immunoconjugate preparation, or a composition described herein, is said to be administered in a "therapeutically effective amount" if the amount administered is physiologically significant. An agent is physiologically significant if its presence results in a detectable change in the physiology of a recipient mammal. In particular, an anti-HIV antibody preparation is physiologically significant if its presence reduces, inhibits or eliminates HIV-infected cells or reduces, inhibits or eliminates HIV infection of non-infected cells.

A composition is said to be a "pharmaceutically acceptable carrier" if its administration can be tolerated by a recipient patient. Sterile phosphate-buffered saline is one example of a pharmaceutically acceptable carrier. Other suitable carriers are well known to those in the art. See, for example, REMINGTON'S PHARMACEUTICAL SCIENCES, 19th Ed. (Mack Publishing Co. 1995), and Goodman and Gilman's THE PHARMACOLOGICAL BASIS OF THERAPEUTICS (Goodman et al., Eds. Macmillan Publishing Co., New York, 1980 and 2001 editions).

Abbreviations used are:

ABS, sodium acetate buffer containing 150 mM sodium chloride;
ADCC, antibody-dependent cellular cytotoxicity;
DTT, dithiothreitol;
ELISA, enzyme-linked immunosorbent assay;
ART, anti-retroviral therapy;
HIV, human immunodeficiency virus;
MAb, monoclonal antibody;
MuLV, Murine Leukemia Virus;
PBMC, peripheral blood mononuclear cells;
$TCID_{50}$, 50% tissue culture infectious dose.

DOCK-AND-LOCK® (DNL®)

The DOCK-AND-LOCK® (DNL®) technique has been used to prepare a wide variety of multimeric constructs (see, e.g., U.S. Pat. Nos. 7,521,056; 7,527,787; 7,534,866; 7,550,143 and 7,666,400, the Examples section of each of which is incorporated herein by reference.) The DNL® technique is capable of joining virtually any effector subunit(s) of interest in a stable complex, with very high reproducibility and efficiency. Generally, DNL® takes advantage of the specific and high-affinity binding interaction between a dimerization and docking domain (DDD) sequence derived from cAMP-dependent protein kinase regulatory subunit and an anchor domain (AD) sequence derived from any of a variety of AKAP proteins. The DDD and AD peptides may be attached to any protein, peptide or other molecule. Because the DDD sequences spontaneously dimerize and bind to the AD sequence, the DNL® technique allows the formation of complexes between any selected molecules that may be attached to DDD or AD sequences. Although the standard DNL® complex comprises a trimer with two DDD-linked molecules attached to one AD-linked molecule, variations in complex structure allow the formation of dimers, trimers, tetramers, pentamers, hexamers and other multimers.

In some embodiments, the DNL® complex may comprise two or more antibodies, antibody fragments or fusion proteins which bind to different epitopes of the same antigen or to two or more different antigens. The DNL® complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, polymers such as PEG, enzymes, therapeutic agents, hormones, cytotoxic agents, anti-angiogenic agents, pro-apoptotic agents or any other molecule or aggregate.

The DNL® method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four isoforms of PKA regulatory subunits are RIα, RIβ, RIIα and RIIβ. The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunit and the AD of AKAP as an excellent pair of linker modules for docking any two entities, referred to hereafter as A and B, into a noncovalent complex, which could be further locked into a DNL® complex through the introduction of cysteine residues into both the DDD and AD at strategic positions to facilitate the formation of disulfide bonds. The general methodology of the DOCK-AND-LOCK® approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL® constructs of different stoichiometry may be produced and used, including but not limited to dimeric, trimeric, tetrameric, pentameric and hexameric DNL® constructs (see, e.g., U.S. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL® construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL® constructs, different AD or DDD sequences may be utilized. Exemplary DDD and AD sequences are provided below.

```
DDD1
                                          (SEQ ID NO: 1)
SHIQIPPGLTELLQGYTVEVLRQQPPDLVEFAVEYFTRLREARA

DDD2
                                          (SEQ ID NO: 2)
CGHIQIPPGLTELLQGYTVEVLRQQPPDLVEFAVEYFTRLREARA

AD1
                                          (SEQ ID NO: 3)
QIEYLAKQIVDNAIQQA

AD2
                                          (SEQ ID NO: 4)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                          (SEQ ID NO: 5)
SLRECELYVQKHNIQALLKDSIVQLCTARPERPMAFLREYFERLEKEEA
K

DDD3C
                                          (SEQ ID NO: 6)
MSCGGSLRECELYVQKHNIQALLKDSIVQLCTARPERPMAFLREYFERL
EKEEAK

AD3
                                          (SEQ ID NO: 7)
CGFEELAWKIAKMIWSDVFQQGC
```

In other alternative embodiments, other sequence variants of AD and/or DDD moieties may be utilized in construction of the DNL® complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                          (SEQ ID NO: 8)
SLRECELYVQKHNIQALLKDVSIVQLCTARPERPMAFLREYFEKLEKEE
AK

PKA RIβ
                                          (SEQ ID NO: 9)
SLKGCELYVQLHGIQQVLKDCIVHLCISKPERPMKFLREHFEKLEKEEN
RQILA

PKA RIIα
                                          (SEQ ID NO: 10)
SHIQIPPGLTELLQGYTVEVGQQPPDLVDFAVEYFTRLREARRQ

PKA RIIβ
                                          (SEQ ID NO: 11)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                          (SEQ ID NO: 1)
SHIQIPPGLTELLQGYTVEVLRQQPPDLVEFAVEYFTRLREARA
```
(underlined: I, Q, I, P, P, G, L, T, E, L, L, Q, G, Y, T, V, E, V, L, V, E, F, A, V, E, Y, F)

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 1. In devising Table 1, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. Even with such conservative substitutions, there are over twenty million possible alternative sequences for the 44 residue peptide (2×3×2×2× 2×2×2×2×2×2×2×2×2×2×2×4×2×2×2×2×2×4×2×4). A limited number of such potential alternative DDD moiety sequences are shown in SEQ ID NO:12 to SEQ ID NO:31 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

TABLE 1

Conservative Amino Acid Substitutions in DDD1 (SEQ ID NO: 1). Consensus sequence disclosed as SEQ ID NO: 90.

| | | | | | | | | | | | | | | | | | | | | | |
|---|---|---|---|---|---|---|---|---|---|---|---|---|---|---|---|---|---|---|---|---|---|
| S | H | I | Q | I | P | P | G | L | T | E | L | L | Q | G | Y | T | V | E | V | L | R |
| T | K | | N | | | | A | | S | D | | | N | A | | S | | D | | | K |
| | R | | | | | | | | | | | | | | | | | | | | |
| Q | Q | P | P | D | L | V | E | F | A | V | E | Y | F | T | R | L | R | E | A | R | A |
| N | N | | | E | | | D | | L | | D | | | S | K | | K | D | L | K | L |
| | | | | | | | | | I | | | | | | | | | | I | | I |
| | | | | | | | | | V | | | | | | | | | | V | | V |

THIQIPPGLTELLQGYTVEVLRQQPPDLVEFAVEYFTRLREARA (SEQ ID NO: 12)

SKIQIPPGLTELLQGYTVEVLRQQPPDLVEFAVEYFTRLREARA (SEQ ID NO: 13)

SRIQIPPGLTELLQGYTVEVLRQQPPDLVEFAVEYFTRLREARA (SEQ ID NO: 14)

SHINIPPGLTELLQGYTVEVLRQQPPDLVEFAVEYFTRLREARA (SEQ ID NO: 15)

SHIQIPPALTELLQGYTVEVLRQQPPDLVEFAVEYFTRLREARA (SEQ ID NO: 16)

SHIQIPPGLSELLQGYTVEVLRQQPPDLVEFAVEYFTRLREARA (SEQ ID NO: 17)

SHIQIPPGLTDLLQGYTVEVLRQQPPDLVEFAVEYFTRLREARA (SEQ ID NO: 18)

SHIQIPPGLTELLNGYTVEVLRQQPPDLVEFAVEYFTRLREARA (SEQ ID NO: 19)

SHIQIPPGLTELLQAYTVEVLRQQPPDLVEFAVEYFTRLREARA (SEQ ID NO: 20)

SHIQIPPGLTELLQGYSVEVLRQQPPDLVEFAVEYFTRLREARA (SEQ ID NO: 21)

SHIQIPPGLTELLQGYTVDVLRQQPPDLVEFAVEYFTRLREARA (SEQ ID NO: 22)

SHIQIPPGLTELLQGYTVEVLKQQPPDLVEFAVEYFTRLREARA (SEQ ID NO: 23)

SHIQIPPGLTELLQGYTVEVLRNQPPDLVEFAVEYFTRLREARA (SEQ ID NO: 24)

SHIQIPPGLTELLQGYTVEVLRQNPPDLVEFAVEYFTRLREARA (SEQ ID NO: 25)

SHIQIPPGLTELLQGYTVEVLRQQPPELVEFAVEYFTRLREARA (SEQ ID NO: 26)

SHIQIPPGLTELLQGYTVEVLRQQPPDLVDFAVEYFTRLREARA (SEQ ID NO: 27)

SHIQIPPGLTELLQGYTVEVLRQQPPDLVEFLVEYFTRLREARA (SEQ ID NO: 28)

SHIQIPPGLTELLQGYTVEVLRQQPPDLVEFIVEYFTRLREARA (SEQ ID NO: 29)

SHIQIPPGLTELLQGYTVEVLRQQPPDLVEFVVEYFTRLREARA (SEQ ID NO: 30)

SHIQIPPGLTELLQGYTVEVLRQQPPDLVEFAVDYFTRLREARA (SEQ ID NO: 31)

Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3 below. The skilled artisan will realize that in designing sequence variants of the AD sequence, one would desirably avoid changing any of the underlined residues, while conservative amino acid substitutions might be made for residues that are less critical for DDD binding. Table 2 shows potential conservative amino acid substitutions in the sequence of AKAP-IS (AD1, SEQ ID NO:3), similar to that shown for DDD1 (SEQ ID NO:1) in Table 1 above.

Even with such conservative substitutions, there are over thirty-five thousand possible alternative sequences for the 17 residue AD1 (SEQ ID NO:3) peptide sequence (2×3×2×4×3×2×2×2×2×2×2×4). A limited number of such potential alternative AD moiety sequences are shown in SEQ ID NO:32 to SEQ ID NO:49 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

```
AKAP-IS
QIEYLAKQIVDNAIQQA        (SEQ ID NO: 3)
```

TABLE 2

Conservative Amino Acid Substitutions in AD1 (SEQ ID NO: 3). Consensus sequence disclosed as SEQ ID NO: 91.

| Q | I | E | Y | L | A | K | Q | I | V | D | N | A | I | the RII form of PKA. The sequences of various AKAP antagonistic peptides are provided in Table 1 of Hundsrucker et al., reproduced in Table 3 below. AKAPIS represents a synthetic RII subunit-binding peptide. All other peptides are derived from the RII-binding domains of the indicated AKAPs.

TABLE 3

AKAP Peptide sequences

| | Peptide Sequence |
|---|---|
| AKAPIS | QIEYLAKQIVDNAIQQA (SEQ ID NO: 3) |
| AKAPIS-P | QIEYLAKQIPDNAIQQA (SEQ ID NO: 67) |
| Ht31 | KGADLIEEAASRIVDAVIEQVKAAG (SEQ ID NO: 68) |
| Ht31-P | KGADLIEEAASRIPDAPIEQVKAAG (SEQ ID NO: 69) |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP10-pep | NTDEAQEELAWKIAKMIVSDIMQQA (SEQ ID NO: 80) |
| AKAP11-pep | VNLDKKAVLAEKIVAEAIEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Figure 4:
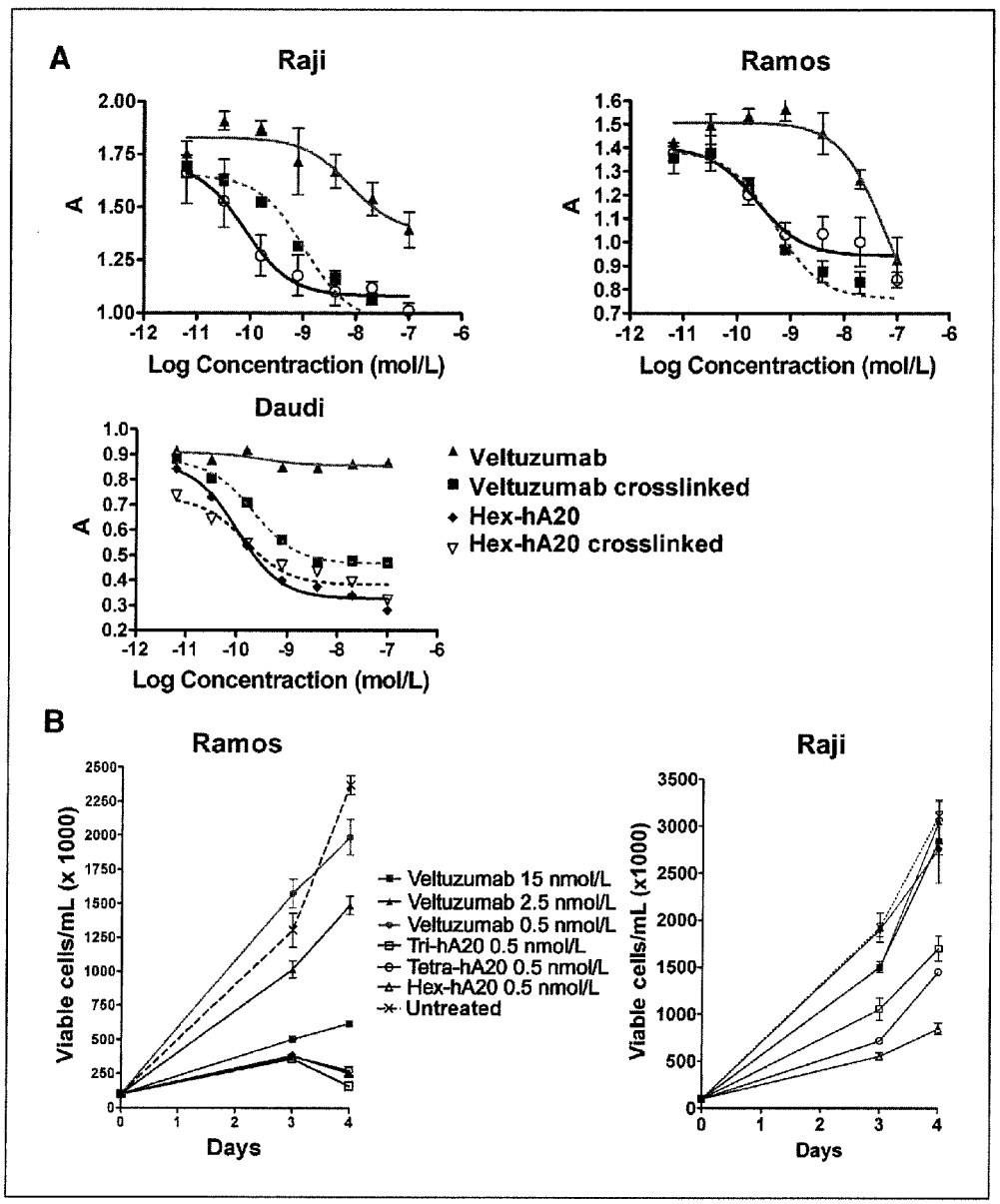
FIG. 4. Inhibition of cell proliferation. (A) In vitro antiproliferation determined by the 4-d MTS assay for Raji, Ramos, or Daudi. Cells were treated with Hex-hA20 (○), veltuzumab (], or veltuzumab plus goat anti-human Fc (■). Daudi cells were also treated with Hex-hA20 plus goat anti-human Fc (∇). Briefly, cells were placed in 96-well plates at 5,000 cells per well in complete RPMI 1640. Five-fold serial dilutions of Hex-hA20, veltuzumab, or veltuzumab cross-linked with goat-anti human Fc were added to triplicate wells at final concentrations ranging from $2\times10^{-8}$ to $6.4\times10^{-12}$ mol/L. The plates were incubated for 4 d, after which 20 µL of CELLTITER 96® Aqueous One Solution Reagent (Promega Corp.) was added, and the incubation was continued for an additional 4 h before reading the plates at 490 nm. (B) In vitro antiproliferation determined by the viable cell counting assay for Ramos (left) or Raji (right). Cells were seeded in T-flasks at $1\times10^5$ cells/mL and treated with veltuzumab, Tri-hA20, Tetra-hA20, or Hex-hA20 at the indicated concentrations. Viable cell densities (VCD) were determined daily over 5 d by flow cytometry. On day 3, cultures were split 1:2 to maintain logarithmic growth. Cells were plotted as viable cells per milliliter measured on days 3, 4, and 5 at the indicated concentrations.

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS
QIEYL<u>A</u>KQ<u>IV</u>DN<u>AI</u>QQA          (SEQ ID NO: 3)

Carr et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 1)
SH*IQIPP*GL*TELLQGYTVEVLRQQPPDLVEFAVEYFTRLREARA*

A modified set of conservative amino acid substitutions for the DDD1 (SEQ ID NO:1) sequence, based on the data of Carr et al. (2001) is shown in Table 4. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 1 and Table 2.

TABLE 4

Conservative Amino Acid Substitutions in DDD1 (SEQ ID NO: 1). Consensus sequence disclosed as SEQ ID NO: 92.

| S | H*I* | Q | *I* | P | P | G*L* | T | E | *LL* | Q*G* | *YT* | V | E | *VL* | R |
|---|---|---|---|---|---|---|---|---|---|---|---|---|---|---|---|
| T | | | N | | | | | S | | | | | | I | |
| | | | | | | | | | | | | | | L | |
| | | | | | | | | | | | | | | A | |

| Q | *QP* | P | *D* | *LV* | E*F* | A | V | E*Y* | *FT* | R | *L* | R | E | A*R* | A |
|---|---|---|---|---|---|---|---|---|---|---|---|---|---|---|---|
| N | | | | | | I | D | | S | K | | K | L | | L |
| | | | | | | L | | | | | | | | I | I |
| | | | | | | A | | | | | | | | V | V |

The skilled artisan will realize that these and other amino acid substitutions in the DDD or AD amino acid sequences may be utilized to produce alternative species within the genus of AD or DDD moieties, using techniques that are standard in the field and only routine experimentation.

Amino Acid Substitutions

In alternative embodiments, the disclosed methods and compositions may involve production and use of proteins or peptides with one or more substituted amino acid residues.

For example, the DDD and/or AD sequences used to make DNL® constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Antibodies

Various embodiments may concern antibodies and/or antibody fragments that bind to one or more antigens or epitopes of HIV. In preferred embodiments, the antigen or epitope is one that is exposed on the surface of HIV-infected cells, such as the HIV envelope protein. Alternatively, the antigen or epitope may be one that is displayed on the surface of an HIV-infected cell. Techniques for preparing and using various antibody-based constructs and fragments are well known in the art. Means for preparing and characterizing antibodies are also well known in the art (See, e.g., Harlowe and Lane, 1988, *Antibodies: A Laboratory Manual*, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.).

Monoclonal Antibodies

While preferred embodiments may concern the use of the P4/D10 antibody, other anti-HIV antibodies may be obtained, prepared and/or used. A variety of antibodies against HIV have been reported and in certain embodiments any such known anti-HIV antibody may be utilized. For example, 4E10 (Rosa et al., Immunity 2:163-73, 2005); 2F5 (Bryson et al., Protein and Peptide Letters, 8:413-18, 2001); 3D6 (Ruker et al., Ann. NY Acad. Sci. 646:212-19, 1991); C37 (Cao et al., DNA and Cell Biology, 12:836-41, 2004); 1ACY, 1F58, 1GGGC (Berry et al., Proteins, 45:281-82, 2001); 2G12 (Armbruster et al., J. Antimicrob. Chemother. 54:915-20, 2004), each incorporated herein by reference. In alternative embodiments, monoclonal antibodies may be readily prepared through use of well-known techniques, such as those exemplified in U.S. Pat. No. 4,196,265. Typically, this technique involves immunizing a suitable animal with a selected immunogen composition. Cells from rodents such as mice and rats are preferred. Mice are more preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the MAb generating protocol.

These cells may be obtained from biopsied spleens, tonsils or lymph nodes, or from a peripheral blood sample. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B-lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art. For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus, and those using polyethylene glycol (PEG), such as 37% (v/v) PEG, have been described. The use of electrically induced fusion methods is also appropriate.

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two wk. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines also could be cultured in vitro, where the MAbs are naturally secreted into the culture medium from which they can be readily obtained in high concentrations. MAbs produced by either means may be further purified, if desired, using filtration, centrifugation, and various chromatographic methods such as HPLC or affinity chromatography.

Production of Antibody Fragments

Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide a 5S fragment denoted $F(ab')_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotide linker sequence. The structural gene is inserted into an expression vector that is subsequently introduced into a host cell, such as E. coli. The recombinant host cells synthesize a single polypeptide chain with a linker peptide bridging the two V domains. Methods for producing sFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780). Single domain antibodies may be obtained, for example, from camels, alpacas or llamas by standard immunization techniques. (See, e.g., Muyldermans et al., TIBS 26:230-235, 2001; Yau et al., J Immunol Methods 281: 161-75, 2003; Maass et al., J Immunol Methods 324:13-25, 2007). They can have potent antigen-binding capacity and can interact with novel epitopes that are inaccessible to conventional $V_H$-$V_L$ pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and single domain antibodies can be isolated that bind to and neutralize the target antigen (Maass et al., 2007). PCR primers that amplify virtually all alpaca antibody coding sequences have been identified and may be used to construct single domain phage display libraries, which can be used for antibody fragment isolation by standard biopanning techniques well known in the art (Maass et al., 2007).

In certain embodiments, the sequences of antibodies or antibody fragments, such as the Fc portions of antibodies, may be varied to optimize their physiological characteristics, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797).

Chimeric and Humanized Antibodies

A chimeric antibody is a recombinant protein in which the variable regions of, for example, a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

Human Antibodies

In another embodiment, an antibody may be a human monoclonal antibody. Such antibodies may be obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994).

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as HIV infection or AIDS. The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ, and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, such as biopanning. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. A non-limiting example of such a system is the XenoMouse® (e.g., Green et al., 1999, *J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

HIV Neutralizing Antibodies

In certain embodiments, neutralizing antibodies or fragments thereof that are capable of destroying or inhibiting the infectivity and/or virulence of HIV are preferred. A variety of HIV neutralizing antibodies are known in the art and any such known antibodies or fragments thereof may be used, including but not limited to P4/D10, 2G12 (e.g., Joos et al., *Antimicrob Agents Chemother* 2006, 50:1773-79), 4E10 (Joos et al., 2006), 2F5 (Joos et al., 2006), b12 (e.g., Wu et al., *J Virol* 2006, 80:2585), X5 (Moulard et al., *Proc Natl Acad Sci* 2002, 99:6913-18) or any combination thereof. Where multispecific antibodies or fragments are used, the skilled artisan will realize that multiple antibodies or fragments that bind to the same or different HIV epitopes may be combined. Although antibodies against the HIV envelope protein (gp120) and/or gp41 are preferred, the skilled artisan will realize that other HIV target antigens may be utilized to develop antibodies or fragments thereof that will target HIV-infected cells. In some cases, antibodies or fragments that bind to one or more HIV antigens in combination with T-cell antigens (e.g., CD4, CCR5 and/or CXCR4) may be utilized.

Fusion Proteins

Various embodiments may concern fusion proteins. These molecules generally have all or a substantial portion of a peptide, linked at the N- or C-terminus, to all or a portion of a second polypeptide or protein. For example, fusions may employ leader sequences from other species to permit the recombinant expression of a protein in a heterologous host. Another useful fusion includes the attachment of an immunologically active domain, such as an antibody or fragment, to a therapeutic agent, such as a peptide or protein toxin or enzyme. Yet another useful form of fusion may include attachment of a moiety of use for purification, such as the FLAG epitope (Prickett et al., 1989, *Biotechniques* 7:580-589; Castrucci et al., 1992, *J Virol* 66:4647-4653). Methods of generating fusion proteins are well known to those of skill in the art. Such proteins may be produced, for example, by chemical attachment using bifunctional cross-linking reagents, by de novo synthesis of the complete fusion protein, or by attachment of a DNA sequence encoding a first protein or peptide to a DNA sequence encoding a second peptide or protein, followed by expression of the intact fusion protein.

Immunoconjugates

In various embodiments, the anti-HIV antibodies, antibody fragments or other targeting molecules of the DNL® complex may be directly conjugated to one or more therapeutic agents. Exemplary therapeutic agents may be selected from the group consisting of cytotoxic agents, drugs, toxins, radionuclides, enzymes, hormones, cytokines or other immunomodulators.

Therapeutic agents of use may comprise one or more of aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, dactinomycin, daunomycin glucuronide, daunorubicin, doxorubicin, 2-pyrrolinodoxorubicine (2P-DOX), cyanomorpholino doxorubicin, doxorubicin glucuronide, epirubicin glucuronide, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyurea, idarubicin, ifosfamide, L-asparaginase, leucovorin, lomustine, mechlorethamine, melphalan, mercaptopurine, 6-mercaptopurine, methotrexate, mitoxantrone, mithramycin, mitomycin, mitotane, phenyl butyrate, procarbazine, pentostatin, PSI-341, semustine, streptozocin, taxanes, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas* exotoxin, *Pseudomonas* endotoxin, an antisense oligonucleotide, an interference RNA, or a combination thereof.

Conjugation can be via, for example, covalent attachments to amino acid residues containing amine, carboxyl, thiol or hydroxyl groups in their side-chains. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the HIV targeting molecules preferably does not significantly affect the binding activity or specificity compared to the unmodified structures. In addition, cytotoxic and/or virostatic agents may be first coupled to a polymeric carrier, which is then conjugated to a HIV targeting molecule. For this method, see Ryser et al., *Proc. Natl. Acad. Sci. USA*, 75:3867-3870, 1978, U.S. Pat. No. 4,699,784, and U.S. Pat. No. 4,046,722, which are incorporated herein by reference.

The conjugates described herein can be prepared by methods known for linking antibodies with lipids, carbohydrates, proteins, radionuclides, or other atoms and molecules. For example, the HIV targeting molecules described herein can be linked to one or more of the carriers described herein (e.g., lipids, polymers, liposomes, micelles, or nanoparticles) to form a conjugate, which can then incorporate a therapeutic or diagnostic agent either covalently, non-covalently, or otherwise. Alternatively, any of the HIV targeting molecules described herein can be conjugated directly with one or more therapeutic or diagnostic agents described herein.

For example, a HIV targeting molecule can be radiolabeled with $^{131}$I and conjugated to a lipid, such that the resulting conjugate can form a liposome. The liposome may incorporate one or more therapeutic (e.g., a drug such as FUdR-dO) or diagnostic agents. The formation of liposomes and micelles is known in the art. See, e.g., Wrobel and Collins, Biochimica et Biophysica Acta (1995), 1235: 296-304; Lundberg et al., J. Pharm. Pharmacol. (1999), 51:1099-1105; Lundberg et al., Int. J. Pharm. (2000), 205:101-108; Lundberg, J. Pharm. Sci. (1994), 83:72-75; Xu et al., Molec. Cancer Ther. (2002), 1:337-346; Torchilin et al., Proc. Nat'l. Acad. Sci., U.S.A. (2003), 100:6039-6044; U.S. Pat. No. 5,565,215; U.S. Pat. No. 6,379,698; and U.S. 2003/0082154.

Nanoparticles or nanocapsules formed from polymers, silica, or metals, which are useful for drug delivery or imaging, have been described as well. See, e.g., West et al., Applications of Nanotechnology to Biotechnology (2000), 11:215-217; U.S. Pat. No. 5,620,708; U.S. Pat. No. 5,702,727; and U.S. Pat. No. 6,530,944. The conjugation of antibodies or binding molecules to liposomes to form a targeted carrier for therapeutic or diagnostic agents has been described. See, e.g., Bendas, Biodrugs (2001), 15:215-224; Xu et al., Mol. Cancer Ther (2002), 1:337-346; Torchilin et al., Proc. Nat'l. Acad. Sci. U.S.A (2003), 100:6039-6044; Bally, et al., J. Liposome Res. (1998), 8:299-335; Lundberg, Int. J. Pharm. (1994), 109:73-81; Lundberg, J. Pharm. Pharmacol. (1997), 49:16-21; Lundberg, Anti-cancer Drug Design (1998), 13: 453-461. See also U.S. Pat. No. 6,306,393; U.S. Ser. No. 10/350,096; U.S. Ser. No. 09/590,284, and U.S. Ser. No. 60/138,284, filed Jun. 9, 1999. All these references are incorporated herein by reference.

A wide variety of diagnostic and therapeutic agents can be advantageously used to form the conjugates of the HIV targeting molecules, or may be linked to haptens that bind to a recognition site on the HIV targeting molecules. Diagnostic agents may include radioisotopes, enhancing agents for use in MRI or contrast agents for ultrasound imaging, and fluorescent compounds. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509).

In order to load a HIV targeting molecule with radioactive metals or paramagnetic ions, it may be necessary to first react it with a carrier to which multiple copies of a chelating group for binding the radioactive metals or paramagnetic ions have been attached. Such a carrier can be a polylysine, polysaccharide, or a derivatized or derivatizable polymeric substance having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and the like known to be useful for this purpose. Carriers containing chelates are coupled to the HIV targeting molecule using standard chemistries in a way to minimize aggregation and loss of immunoreactivity.

Other, more unusual, methods and reagents that may be applied for preparing such conjugates are disclosed in U.S. Pat. No. 4,824,659, which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV. Some useful diagnostic nuclides may include $^{18}F$, $^{52}Fe$, $^{62}Cu$, $^{64}Cu$, $^{67}Cu$, $^{67}Ga$, $^{68}Ga$, $^{86}Y$, $^{89}Zr$, $^{94}Tc$, $^{94m}Tc$, $^{99m}Tc$, or $^{111}In$. The same chelates complexed with non-radioactive metals, such as manganese, iron and gadolinium, are useful for MRI, when used along with the HIV targeting molecules and carriers described herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}Ra$, may be used.

Therapeutic agents include, for example, chemotherapeutic drugs such as vinca alkaloids, anthracyclines, epipodophyllotoxins, taxanes, antimetabolites, alkylating agents, antibiotics, Cox-2 inhibitors, antimitotics, antiangiogenic and proapoptotic agents, particularly doxorubicin, methotrexate, taxol, CPT-11, camptothecans, and others from these and other classes of cytotoxic agents. Other cytotoxic agents include nitrogen mustards, alkyl sulfonates, nitrosoureas, triazenes, folic acid analogs, pyrimidine analogs, purine analogs, platinum coordination complexes, and the like. Suitable cytotoxic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable cytotoxic agents, such as experimental drugs, are known to those of skill in the art, and may be conjugated to the HIV targeting molecules described herein using methods that are known in the art.

Another class of therapeutic agents consists of radionuclides that emit α-particles (such as $^{212}Pb$, $^{212}Bi$, $^{213}Bi$, $^{211}At$, $^{223}Ra$, $^{225}Ac$), β-particles such as $^{32}P$, $^{33}P$, $^{47}Sc$, $^{67}Cu$, $^{67}Ga$, $^{89}Sr$, $^{90}Y$, $^{111}Ag$, $^{125}I$, $^{131}I$, $^{142}Pr$, $^{153}Sm$, $^{161}Tb$, $^{166}Ho$, $^{166}Dy$, $^{177}Lu$, $^{186}Re$, $^{188}Re$, $^{189}Re$), or Auger electrons (such as $^{111}In$, $^{125}I$, $^{67}Ga$, $^{191}Os$, $^{193m}Pt$, $^{195m}Pt$, $^{195m}Hg$). The HIV targeting molecules may be labeled with one or more of the above radionuclides using methods as described for the diagnostic agents.

In certain embodiments, the therapeutic agents of use may comprise one or more aggresome inhibitors. Aggresomes are large intracellular complexes that were thought to form in response to misfolded protein (see, e.g., Heath et al., J. Cell Biol. 153:449-55, 2001; Johnstone et al., J. Cell Biol. 143: 1883-98, 1998; Wileman, Science 312:875-78, 2006). More recently, it has been suggested that aggresomes may function in the assembly of viral particles (Heath et al., 2001; Wileman, 2006). Aggresome inhibitors may therefore function to block or inhibit the formation of new infectious viral particles from cells infected with HIV or other viruses. A variety of aggresome inhibitors are known, such as ALLN, nocodazole, colchicine and vinblastine (Johnston et al., 1998), other microtubule inhibitors (Gerdes and Katsanis, Hum. Molec. Genet. 14:R291-300, 2005); bortezomib (VELCADE®) (Catley et al., Blood 108:3441-49, 2006), tubacin, histone deacetylase inhibitors (Corcoran et al., Curr. Biol. 14:488-92, 2004), and any such known aggresome inhibitor may be used.

In various embodiments, one or more immunomodulators may be conjugated to an anti-HIV antibody or fragment. Alternatively, an immunomodulator may be attached to an AD or DDD moiety for incorporation into a DNL® complex, as described below. As used herein, the term "immunomodulator" includes cytokines, stem cell growth factors, lymphotoxins and hematopoietic factors, such as interleukins, colony stimulating factors, interferons (e.g., interferons-α, β and -γ) and the stem cell growth factor designated "S1 factor."

Examples of suitable immunomodulator moieties include IL-2, IL-6, IL-10, IL-12, IL-18, IL-21, interferon-gamma, TNF-alpha, and the like.

The term "cytokine" is a generic term for proteins or peptides released by one cell population which act on another cell as intercellular mediators. As used broadly herein, examples of cytokines include lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to a site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines. Similarly, the terms immunomodulator and cytokine overlap in their respective members.

A suitable peptide containing a detectable label (e.g., a fluorescent molecule), or a virostatic and/or cytotoxic agent, (e.g., a radioiodine), can be covalently, non-covalently, or otherwise associated with the HIV targeting molecules. For example, a therapeutically useful conjugate can be obtained by incorporating a photoactive agent or dye onto the HIV targeting molecules. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

HIV Fusion Inhibitors

HIV fusion inhibitors are described in PCT Patent Application Publ. No. WO 2007045463, the entire text of which is incorporated herein by reference. Generally, infection of cells by human immunodeficiency virus (HIV) is effected by a process in which the membrane of the cells to be infected and the viral membrane are fused. The viral envelope glycoprotein complex (gp120/gp41) interacts with a cell surface receptor located on the membrane of the cell to be infected. The binding of gp120 to e.g. the CD4 receptor in combination with a co-receptor such as CCR-5 or CXCR-4, causes a change in the conformation of the gp120/gp41 complex. As a result of of this conformational change the gp41 protein is able to insert into the membrane of the target cell. This insertion is the beginning of the membrane fusion process.

It is known that the amino acid sequence of the gp41 protein differs between the different HIV strains because of naturally occurring polymorphisms. But the same domain architecture can be recognized, a fusion signal, two heptad repeat domains (HR1, HR2) and a transmembrane domain. The fusion (or fusogenic) domain participates in the insertion into and disintegration of the cell membrane. Peptides with amino acid sequences deduced from the HR1 or HR2 domain of gp41 are effective in vitro and in vivo inhibitors of HIV uptake into cells (see, e.g. U.S. Pat. Nos. 5,464,933; 5,656, 480; 6,258,782; 6,348,568; 6,656,906). For example, T20, an HR2 peptide and T651 (U.S. Pat. No. 6,479,055) are potent inhibitors of HIV infection. Attempts have been made to enhance the efficacy of HR2 derived peptides, for example by amino acid substitution or chemical crosslinking (Sia et al, 2002, PNAS USA 99:14664-14669; Otaka et al, 2002, Angew. Chem. Int. 41:2937-2940).

Exemplary anti-fusogenic peptides are found in U.S. Pat. Nos. 5,464,933; 5,656,480; 6,013,263; 6,017,536; 6,020,459; 6,093,794; 6,060,065; 6,258,782; 6,348,568; 6,479,055; 6,656,906; and PCT Patent Application Publ. Nos. WO 1996/19495, WO 1996/40191, WO 1999/59615, WO 2000/69902, and WO 2005/067960, the Examples section of each incorporated herein by reference. The skilled artisan will realize that any such HIV fusion inhibitor may be incorporated into the subject DNL® complexes utilizing the techniques described in the Examples below.

Interference RNA

In certain embodiments a DNL® complex may be utilized to deliver an siRNA or interference RNA species. The siRNA, interference RNA or therapeutic gene may be attached to a carrier moiety that is incorporated into a DNL® construct. A variety of carrier moieties for siRNA have been reported and any such known carrier may be used. Non-limiting examples of carriers include protamine (Rossi, 2005, Nat Biotech 23:682-84; Song et al., 2005, Nat Biotech 23:709-17); dendrimers such as PAMAM dendrimers (Pan et al., 2007, Cancer Res. 67:8156-8163); polyethylenimine (Schiffelers et al., 2004, Nucl Acids Res 32:e149); polypropyleneimine (Taratula et al., 2009, J Control Release 140:284-93); polylysine (Inoue et al., 2008, J Control Release 126:59-66); histidine-containing reducible polycations (Stevenson et al., 2008, J Control Release 130:46-56); histone H1 protein (Haberland et al., 2009, Mol Biol Rep 26:1083-93); cationic comb-type copolymers (Sato et al., 2007, J Control Release 122: 209-16); polymeric micelles (U.S. Patent Application Publ. No. 20100121043); and chitosan-thiamine pyrophosphate (Rojanarata et al., 2008, Pharm Res 25:2807-14). The skilled artisan will realize that in general, polycationic proteins or polymers are of use as siRNA carriers. The skilled artisan will further realize that siRNA carriers can also be used to carry other oligonucleotide or nucleic acid species, such as antisense oligonucleotides or short DNA genes.

Many siRNA species are commercially available from known sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Mirus Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Other known siRNA species have been reported, for example, for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421). Such known siRNA species may be delivered using the subject DNL® complexes.

Immunotoxins Comprising Ranpirnase (Rap)

Ribonucleases, in particular, Rap (Lee, Exp Opin Biol Ther 2008; 8:813-27) and its more basic variant, amphinase (Ardelt et al., Curr Pharm Biotechnol 2008:9:215-25), are potential cytotoxic agents (Lee and Raines, Biodrugs 2008; 22:53-8). Rap is a single-chain ribonuclease of 104 amino acids originally isolated from the oocytes of *Rana pipiens*. Rap exhibits cytostatic and cytotoxic effects on a variety of cell lines in vitro, as well as antitumor activity in vivo. The amphibian ribonuclease enters cells via receptor-mediated endocytosis and once internalized into the cytosol, selectively degrades tRNA, resulting in inhibition of protein synthesis and induction of apoptosis. Rap can be administered repeatedly to patients without an untoward immune response, with reversible renal toxicity reported to be dose-limiting (Mikulski et al., J Clin Oncol 2002; 20:274-81; Int J Oncol 1993; 3:57-64).

Conjugation or fusion of Rap to a targeting antibody or antibody fragment is a promising approach to enhance its potency, as first demonstrated for LL2-onconase (Newton et al., Blood 2001; 97:528-35), a chemical conjugate comprising Rap and a murine anti-CD22 monoclonal antibody (MAb), and subsequently for 2L-Rap-hLL1-γ4P, a fusion protein comprising Rap and a humanized anti-CD74 MAb (Stein et al., Blood 2004; 104:3705-11).

The method used to generate 2L-Rap-hLL1-γ4P allowed us to develop a series of structurally similar immunotoxins, referred to in general as 2L-Rap-X, all of which consist of two Rap molecules, each connected via a flexible linker to the N-terminus of one L chain of an antibody of interest (X). We have also generated another series of immunotoxins of the same design, referred to as 2LRap(Q)-X, by substituting Rap with its non-glycosylation form of Rap, designated as Rap(Q) to denote that the potential glycosylation site at Asn69 is changed to Gln (or Q, single letter code). For both series, we made the IgG as either IgG1(γ1) or IgG4(γ4), and to prevent the formation of IgG4 half molecules (Aalberse and Schuurman, Immunology 2002; 105:9-19), we converted the serine residue in the hinge region (S228) of IgG4 to proline (γ4P). A pyroglutamate residue at the N-terminus of Rap is required for the RNase to be fully functional (Liao et al., Nucleic Acids Res 2003; 31:5247-55).

The skilled artisan will recognize that the cytotoxic RNase moieties suitable for use in the present invention include polypeptides having a native ranpirnase structure and all enzymatically active variants thereof. These molecules advantageously have an N-terminal pyroglutamic acid resides that appears essential for RNase activity and are not substantially inhibited by mammalian RNase inhibitors. Nucleic acid that encodes a native cytotoxic RNase may be prepared by cloning and restriction of appropriate sequences, or using DNA amplification with polymerase chain reaction (PCR). The amino acid sequence of *Rana Pipiens* ranpirnase can be obtained from Ardelt et al., J. Biol. Chem., 256: 245 (1991), and cDNA sequences encoding native ranpirnase, or a conservatively modified variation thereof, can be gene-synthesized by methods similar to the en bloc V-gene assembly method used in hLL2 humanization. (Leung et al., Mol. Immunol., 32: 1413, 1995). Methods of making cytotoxic RNase variants are known in the art and are within the skill of the routineer.

As described in the Examples below, Rap conjugates of targeting antibodies may be made using the DNL® technology. The DNL® Rap-antibody constructs show potent cytotoxic activity that can be targeted to disease-associated cells.

Formulation and Administration

The DNL® constructs may be further formulated to obtain compositions that include one or more pharmaceutically suitable excipients, one or more additional ingredients, or some combination of these. These can be accomplished by known methods to prepare pharmaceutically useful dosages, whereby the active ingredients are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

One route for administration of the compositions described herein is parenteral injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising DNL® complexes can be used for intravenous administration via, for example, bolus injection or continuous infusion. Compositions for injection can be presented in unit dosage form, e.g., in ampules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, tris (hydroxymethyl) aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. Systemic administration of the formulated composition is typically made every two to three days or once a week if a humanized form of anti-HIV antibody is used. Usually administration is by either intramuscular injection or intravascular infusion.

The compositions may be administered to subcutaneously or by other parenteral routes. Moreover, the administration may be by continuous infusion or by single or multiple boluses. Methods useful for the antibodies or immunoconjugates can be applied to the compositions described herein. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of the active ingredient that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

Pharmaceutical methods employed to control the duration of action of immunoconjugates or antibodies may be applied to the formulated compositions described herein. Control release preparations can be achieved through the use of biocompatible polymers to complex or adsorb the immunoconjugate or naked antibody, for example, matrices of poly(ethylene-co-vinyl acetate) and matrices of a polyanhydride copolymer of a stearic acid dimer and sebacic acid. See Sherwood et al., Bio/Technology (1992), 10: 1446. The rate of release from such a matrix depends upon the molecular weight of the DNL® complex, the amount of DNL® complex within the matrix, and the size of dispersed particles. See Saltzman et al., Biophys. J (1989), 55: 163; Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

A DNL® complex linked to a radionuclide may be effective for therapy. After it has been determined that the DNL® complex is localized at one or more infectious sites in a subject, higher doses of the labeled composition, generally from 20 mCi to 150 mCi per dose for $^{131}$I, 5 mCi to 30 mCi per dose for $^{90}$Y, or 5 mCi to 20 mCi per dose of $^{186}$Re, each based on a 70 kg patient weight, are injected. Injection may be intravenous, intraarterial, intralymphatic, intrathecal, or intracavitary (i.e., parenterally), and may be repeated. It may be advantageous for some therapies to administer multiple, divided doses, thus providing higher toxic doses without usually effecting a proportional increase in radiation of normal tissues.

Kits

Some embodiments concern kits for practicing the claimed methods. The kit may include a DNL® construct. The kit components may be packaged into containers, such as vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The following examples are included to demonstrate preferred embodiments of the invention. It should be appreciated by those of skill in the art that the techniques disclosed in the Examples which follow represent techniques discovered to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Inhibition of HIV Infection In Vitro and In Vivo Using Conjugated Anti-HIV Antibodies Summary Murine monoclonal antibody (MAb) against the envelope antigen of HIV (P4/D10) was conjugated with the conventional anti-cancer drug, doxorubicin, and tested against infectious virus and infected cells, both in vitro and in vivo. P4/D10 antibody was incubated with free virus (neutralization) or HIV-infected cells (inhibition) and the resulting infection was measured by a p24 capture enzyme-linked immunosorbent assay. In an HIV-1/MuLV mouse challenge model the ability of the conjugate to inhibit infection in vivo was measured.

Doxorubicin-conjugated P4/D10 neutralized HIV-1$_{IIIB}$ and eliminated intercellular spread and HIV replication in infected Jurkat cells in vitro. It also protected mice from challenge with HIV-1$_{IIIB}$/MuLV at an eight-fold lower concentration than needed for free antibody, whereas no effects were observed for free drug or irrelevant conjugate controls. These results demonstrate that doxorubicin was concentrated to HIV-infected cells by the P4/D10 antibody, significantly (p=0.0001) contributing to HIV elimination.

In this study, we conjugated doxorubicin, an anticancer anthracycline with known pharmacology, toxicology, and antitumor activity in patients, to a neutralizing and ADCC-mediating monoclonal antibody (MAb) developed against the HIV-1 outer envelope gp120 (third variable loop region).

The P4/D10 antibody conjugated to doxorubicin was tested in vitro for its efficacy in eliminating HIV-1-infected cells among non-infected cells and in a mouse model by removing HIV-1/MuLV (murine leukemia virus) infected syngeneic cells from the intraperitoneal cavity. The anti-gp120 antibody, P4/D10, neutralizes HIV-1 virus and mediates ADCC (Broliden et al., 1990). It has also been used in its unconjugated form in a phase-I clinical trial for late-stage HIV-1 infected individuals, where it decreased HIV antigens for an extended period of time (Hinkula et al., 1994). The present study was the first to examine the combination of P4/D10 in a drug-conjugated form in a preclinical HIV model, in comparison to free MAb, free drug, and the irrelevant antibodies hRS7 (Stein et al., *Int J Cancer* 1993, 55:938-946) and hLL1 Griffiths et al., *Clin Cancer Res* 2003, 9:6567-6571; Sapra et al., *Clin Cancer Res* 2005, 11:5257-5264), that were conjugated similarly with doxorubicin.

Materials and Methods

Antibodies and Drug Conjugation.

Conjugation of doxorubicin with the IgG1κ anti-gp120 antibody P4/D10 (Broliden et al., 1990) and control antibodies, as well as the preparation of the bifunctional doxorubicin hydrazone derivative with a maleimide group, were performed according to Griffiths et al. (2003). Briefly, antibodies P4/D10, hLL1 (humanized anti-CD74), and hRS7 (humanized anti-EGP-1) in a final concentration of approximately 9 mg/ml, were mildly reduced with DTT (dithiothreitol) in PBS (pH 7.5) containing 5 mM EDTA, using about 2.2 mM final DTT concentration, corresponding to a 38-fold molar excess of the reductant with respect to the antibodies. The solutions were incubated at 37° C. for 40 min. The reduced MAbs were purified on spin-columns of SEPHADEX® G50/80 in 50 mM sodium acetate buffer containing 150 mM NaCl and 2 mM EDTA (pH 5.3). The number of thiol groups generated on the antibodies was determined by Ellman's assay. For conjugation, mildly reduced antibodies at 6.5 mg/ml were mixed with the bifunctional doxorubicin. The incubates were kept on ice for 15 min, and purified on spin columns of G50/80 in 0.1 M sodium acetate (pH 6.5), followed by passage through a short column of Bio-Beads SM2 (Bio-Rad, Hercules, Calif.) equilibrated in the same buffer. The products were analyzed for doxorubicin/MAb substitution ratios by measuring absorbance.

A GMP-produced lot of IgG from HIV infected patients (HIVIgG) (Guay et al. *Aids* 2002, 16:1391-1400) was used as positive control and sera from HIV-negative individuals as negative controls. Free doxorubicin, as well as the anticancer humanized MAbs LL1 and RS7, similarly conjugated with doxorubicin, were included as controls for the conjugated P4/D10 antibody.

HIV-1 Neutralization Assay.

Doxorubicin P4/D10, unlabelled P4/D10, HIV immunoglobulin (HIVIgG), and HIV-negative serum were mixed with the HIV-1 isolate HIV-1$_{IIIB}$ (LAI) and incubated for 1 h at 37° C. before 50,000 Jurkat T-cells/well were added. After 1 h of incubation, the cells were washed with medium and new complete medium added (200 μl/well). After 7 days of culture, the amount of p24 produced was measured by a p24 capture ELISA (enzyme-linked immunosorbent assay) and the percent inhibition of HIV-1 p24 production was calculated.

HIV-1 Inhibition In Vitro.

Jurkat T-cells were infected with HIV-1$_{IIIB}$ by mixing 5-10×10$^6$ cells with 100×TCID$_{50}$ HIV-1$_{IIIB}$ and incubating for 1 h at 37° C. The cells were washed in medium and incubated at 37° C. Every third day, medium was changed and supernatant checked for p24 production. When close to 100% of the cells were infected, different proportions of HIV-1$_{IIIB}$-infected cells were mixed with uninfected cells. The cells were treated with serial dilutions of antibodies, serum, or free doxorubicin from 100 to 0.00001 μg/ml. After seven days of culture at 37° C., HIV-1 p24 inhibition was measured and supernatants from cells previously treated with 0.1-10 μg/ml of doxorubicin-P4/D10, unconjugated P4/D10, and 0.05-0.5 mg/ml HIV-negative serum were collected and transferred to fresh Jurkat T-cells to test if infectious HIV was identified by the p24 ELISA at days 3, 7, 10, 12, and 15 after initiation of the culture.

HIV-1/MuLV Challenge Model.

A human T-cell line, CEM-1B, with a genetically integrated MuLV genome was infected with HIV-1$_{IIIB}$, which led to the production of pseudoviruses with the HIV-1 genome and the MuLV envelope (Adang et al., PNAS USA 1999, 96:12749-753; Hinkula et al., *Cells Tissues Organs* 2004, 177:169-184). These virus supernatants were used to infect splenocytes from C57B1/6×DBA F1 K$^{b/d}$ mice transgenic for HLA-A201. Isogenic mice were challenged with HIV-1$_{IIIB}$/MuLV infected splenocytes i.p. and were immediately given conjugated antibodies, free antibodies or free doxorubicin i.p. Ten days after challenge, mice were sacrificed and peritoneal cells collected. Peritoneal cells were pelleted and added to 1×10$^6$ HIV susceptible Jurkat T-cells or human PBMC grown in 24-well plates. From these secondary cultures, supernatant was removed and fresh medium added every 3-4 days. The amount of infectious HIV recovered in the supernatant was measured for 3 weeks by p24 ELISA.

Statistical Analysis.

To compare the in vitro HIV-1 neutralizing capacities of the anti-gp120 MAbs and control antibodies, Student's t-test and the non-parametric Kruskal-Wallis test were used. Statistical comparisons between the groups of mice treated with different antibodies were performed using the nonparametric Mann-Whitney U and Kruskal-Wallis tests. A difference was considered significant when a p-value of <0.05 was obtained. A non-parametric one-way ANOVA test was performed using PRISM® version 4.0a (GRAPHPAD® Software, San Diego, Calif.) and was used for comparisons of HIV-1 isolation and p24 antigen positivity between the study groups.

Results

The number of thiol groups generated on the respective antibodies by mild reduction, as well as the doxorubicin/MAb substitution ratios in the final purified conjugates, ranged between 8.8 (P4/D10, hRS7) and 9.4 (hLL1), giving a ratio of approximately 9 drug molecules per IgG. High-pressure liquid chromatographic analyses showed that the conjugates and the native MAbs possessed similar retention times, with zero to minimal aggregation (data not shown).

No significant difference in HIV-1 neutralizing capacity of free HIV-1 virus (FIG. 1A) could be shown between the doxorubicin-conjugated P4/D10 MAb and either unconjugated P4/D10 MAb or the HIVIgG antibodies. However, all anti HIV-1 specific antibodies were significantly better then the negative control serum (p=0.001) at neutralizing HIV-1$_{IIIB}$.

When 3% HIV-1$_{IIIB}$ infected Jurkat cells were mixed with 97% uninfected cells, doxorubicin-P4/D10 mediated a significantly (p=0.002) stronger inhibition of intercellular spread of HIV-1 infection than free P4/D10, doxorubicin-conjugated control antibody, hLL1, or free doxorubicin at a concentration of 0.5 or 0.05 μg/ml (FIG. 1B). Similar results were seen at all other concentrations of infected and uninfected cells. It was of particular interest that the intercellular spread of infection appeared to be inhibited even more potently than the effect obtained with doxorubicin-P4/D10 as a neutralizing agent. Also, no infectious virus could be found in the cultures treated with high doses of doxorubicin-P4/

D10, since no p24 production was detected after transfer of supernatants from these cell cultures to uninfected Jurkat cells (data not shown). The significant difference in effect between doxorubicin-P4/D10 and unconjugated P4/D10 could not have been predicted from the results on neutralization of free HIV-1 virus (FIG. 1A).

To test the efficacy of doxorubicin-P4/D10 antibody in vivo, mice were given isogeneic HIV/MuLV-infected cells together with conjugates intraperitoneally. Peritoneal cells were harvested 10 days later and infectious HIV was demonstrated in all controls, similar to previous studies (Hinkula et al., 2004). The doxorubicin-P4/D10 antibody protected mice completely against challenge with HIV-1 infected primary lymphoid cells (p=0.0001) (FIG. 2). No infectious HIV was recovered from peritoneal cells after challenge and treatment with 100 μg of doxorubicin-P4/D10 antibody. When mice were treated with 100 μg of unconjugated P4/D10 antibody, all were positive for p24 production. Complete protection by antibody alone was seen only when the dose was increased eight-fold, to 800 μg unconjugated P4/D10 per mouse. None of the doxorubicin-conjugated control antibodies (hLL1 or hRS7) provided any protection at doses of 100-200 μg, nor did doses of 100-400 μg of free doxorubicin.

Summary

Doxorubicin-P4/D10 was capable of eliminating HIV-1 infected cells in vitro, as well as in an experimental in vivo challenge model. The ability of the unconjugated P4/D10 MAb to mediate ADCC against HIV-1 infected target cells as well as neutralizing HIV-1 (Broliden et al., 1990; Hinkula et al., 1994) may enhance its efficacy as a drug immunoconjugate in a non-toxic manner.

Similarly efficacious anti-HIV immunoconjugates may be incorporated into DNL® complexes, utilizing the compositions and methods disclosed in the following Examples.

Example 2

Preparation of DOCK-AND-LOCK® (DNL®) Constructs DDD and AD Fusion Proteins

The DNL® technique can be used to make dimers, trimers, tetramers, hexamers, etc. comprising virtually any antibody, antibody fragment, immunomodulator, cytokine, PEG moiety, toxin, or other effector moiety. For certain preferred embodiments, an anti-HIV antibody or antibody fragment and an HIV inhibitor may be produced as fusion proteins comprising either a dimerization and docking domain (DDD) or anchoring domain (AD) sequence. Although in preferred embodiments the DDD and AD moieties may be the effector moieties as fusion proteins, the skilled artisan will realize that other methods of conjugation exist, such as chemical cross-linking, click chemistry reaction, etc.

The technique is not limiting and any protein or peptide of use may be produced as an AD or DDD fusion protein for incorporation into a DNL® complex. Where chemical cross-linking is utilized, the AD and DDD conjugates may comprise any molecule that may be cross-linked to an AD or DDD sequence using any cross-linking technique known in the art.

Expression Vectors

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain ($V_H$ and $V_L$) sequences. Using molecular biology tools known to those skilled in the art, these IgG expression vectors can be converted into Fab-DDD or Fab-AD expression vectors.

To generate Fab-DDD expression vectors, the coding sequences for the hinge, CH2 and CH3 domains of the heavy chain were replaced with a sequence encoding the first 4 residues of the hinge, a 14 residue Gly-Ser linker and a DDD moiety, such as the first 44 residues of human RIIα (referred to as DDD1, SEQ ID NO:1). To generate Fab-AD expression vectors, the sequences for the hinge, CH2 and CH3 domains of IgG were replaced with a sequence encoding the first 4 residues of the hinge, a 15 residue Gly-Ser linker and an AD moiety, such as a 17 residue synthetic AD called AKAP-IS (referred to as AD1, SEQ ID NO:3), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1 Antibody Domain

The CH1 antibody domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC, SEQ ID NO:85) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide was synthesized to code for the amino acid sequence of DDD1 preceded by 11 residues of the linker peptide, with the first two codons comprising a BamHI restriction site. A stop codon and an EagI restriction site are appended to the 3'end. The encoded polypeptide sequence is shown below.

(SEQ ID NO: 86)
GSGGGGSGGGGSHIQIPPGLTELLQGYTVEVLRQQPPDLVEFAVEYFTRL
REARA

Two oligonucleotides, designated RIIA1-44 top and RIIA1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3'end. The encoded polypeptide sequence is shown below.

GSGGGGSGGGGSQIEYLAKQIVDNAIQQA    (SEQ ID NO: 87)

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective PGEMT® shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI. The 679 antibody is a hapten-binding antibody specific for histamine succinyl glycine (HSG) (see, e.g., U.S. Pat. Nos. 7,429,381; 7,563,439).

Production and Purification of h679-Fab-AD1

The h679-Fd-AD1-pdHL2 vector was linearized by digestion with Sal I restriction endonuclease and transfected into Sp/EEE myeloma cells by electroporation. The di-cistronic expression vector directs the synthesis and secretion of both h679 kappa light chain and h679 Fd-AD1, which combine to form h679 Fab-AD1. Following electroporation, the cells were plated in 96-well tissue culture plates and transfectant clones were selected with 0.05 µM methotrexate (MTX). Clones were screened for protein expression by ELISA using microtiter plates coated with a BSA-IMP260 (HSG) conjugate and detection with HRP-conjugated goat anti-human Fab. BIAcore analysis using an HSG (IMP239) sensorchip was used to determine the productivity by measuring the initial slope obtained from injection of diluted media samples. The highest producing clone had an initial productivity of approximately 30 mg/L. A total of 230 mg of h679-Fab-AD1 was purified from 4.5 liters of roller bottle culture by single-step IMP291 affinity chromatography. Culture media was concentrated approximately 10-fold by ultrafiltration before loading onto an IMP291-affigel column. The column was washed to baseline with PBS and h679-Fab-AD1 was eluted with 1 M imidazole, 1 mM EDTA, 0.1 M NaAc, pH 4.5. SE-HPLC analysis of the eluate shows a single sharp peak with a retention time consistent with a 50 kDa protein (not shown). Only two bands, which represent the polypeptide constituents of h679-AD1, were evident by reducing SDS-PAGE analysis (not shown).

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN-14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL® complex comprising two Fab fragments of a first antibody and one Fab fragment of a second antibody.

Production and Purification of C-DDD1-Fab-hMN-14

The C-DDD1-Fd-hMN-14-pdHL2 vectors was transfected into Sp2/0-derived myeloma cells by electroporation. C-DDD1-Fd-hMN-14-pdHL2 is a di-cistronic expression vector, which directs the synthesis and secretion of both hMN-14 kappa light chain and hMN-14 Fd-DDD1, which combine to form C-DDD1-hMN-14 Fab. The fusion protein forms a stable homodimer via the interaction of the DDD1 domain.

Following electroporation, the cells were plated in 96-well tissue culture plates and transfectant clones were selected with 0.05 µM methotrexate (MTX). Clones were screened for protein expression by ELISA using microtiter plates coated with WI2 (a rat anti-id monoclonal antibody to hMN-14) and detection with HRP-conjugated goat anti-human Fab. The initial productivity of the highest producing C-DDD1-Fab-hMN14 Fab clone was 60 mg/L. The secreted C-DDD1-Fab-hMN14 may be purified by affinity column chromatograph using and AD1 column. AD1-C is a synthetic peptide consisting of the AD1 sequence and a carboxyl terminal cysteine residue, which was used to couple the peptide to Affigel following reaction of the sulfhydryl group with chloroacetic anhydride. DDD-containing dimer structures specifically bind to the AD1-C-Affigel resin at neutral pH and can be eluted at low pH (e.g., pH 2.5).

The binding activity of C-DDD1-Fab-hMN-14 was determined by SE-HPLC analysis of samples in which the test article was mixed with various amounts of WI2. A sample prepared by mixing WI2 Fab and C-DDD1-Fab-hMN-14 at a molar ratio of 0.75:1 showed three peaks, which were attributed to unbound C-DDD1-Fab-hMN14 (8.71 min), C-DDD1-Fab-hMN-14 bound to one WI2 Fab (7.95 min), and C-DDD1-Fab-hMN14 bound to two WI2 Fabs (7.37 min) (not shown). When a sample containing WI2 Fab and C-DDD1-Fab-hMN-14 at a molar ratio of 4 was analyzed, only a single peak at 7.36 minutes was observed (not shown). These results demonstrated that hMN14-Fab-DDD1 is dimeric and has two active binding sites. A competitive ELISA demonstrated that C-DDD1-Fab-hMN-14 binds to CEA with an avidity similar to hMN-14 IgG, and significantly stronger than monovalent hMN-14 Fab (not shown).

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 (SEQ ID NO:2) appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

h679-Fd-AD2-pdHL2 h679-Fab-AD2, was designed to pair to C-DDD2-Fab-hMN-14. h679-Fd-AD2-pdHL2 is an expression vector for the production of h679-Fab-AD2, which possesses an anchoring domain sequence of AD2 (SEQ ID NO:4) appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Creation of C-H-AD2-IgG-pdHL2 Expression Vectors

A plasmid shuttle vector was produced to facilitate the conversion of any IgG-pdHL2 vector into a C-H-AD2-IgG-pdHL2 vector. The gene for the Fc (CH2 and CH3 domains) was amplified using the pdHL2 vector as a template and Fc BglII Left and Fc Bam-EcoRI Right primers. The amplimer was cloned in the PGEMT® PCR cloning vector. The Fc insert fragment was excised from PGEMT® with XbaI and BamHI restriction enzymes and ligated with AD2-pdHL2 vector that was prepared by digestion of h679-Fab-AD2-pdHL2 with XbaI and BamHI, to generate the shuttle vector Fc-AD2-pdHL2.

Fc BgIII Left (SEQ ID NO: 88)
5'-AGATCTGGCGCACCTGAACTCCTG-3'

Fc Bam-EcoRI Right (SEQ ID NO: 89)
5'-GAATTCGGATCCTTTACCCGGAGACAGGGAGAG-3'

To convert any IgG-pdHL2 expression vector to a C-H-AD2-IgG-pdHL2 expression vector, an 861 bp BsrGI/NdeI restriction fragment is excised from the former and replaced with a 952 bp BsrGI/NdeI restriction fragment excised from the Fc-AD2-pdHL2 vector. BsrGI cuts in the CH3 domain and NdeI cuts downstream (3') of the expression cassette.

Example 3

Generation of TF2 DNL® Complex

A trimeric DNL® complex designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP291 affinity chromatography. Before the addition of TCEP, SE-HPLC did not show any evidence of $a_2b$ formation (not shown). Addition of 5 mM TCEP rapidly resulted in the formation of $a_2b$ complex consistent with a 157 kDa protein expected for the binary structure (not shown). TF2 was purified to near homogeneity by IMP291 affinity chromatography (not shown). IMP291 is a synthetic peptide containing the HSG hapten to which the 679 Fab binds (Rossi et al., 2005, Clin Cancer Res 11:7122s-29s). SE-HPLC analysis of the IMP291 unbound fraction demonstrated the removal of $a_4$, $a_2$ and free kappa chains from the product (not shown).

The functionality of TF2 was determined by BIACORE® assay. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response (not shown). The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Serum Stability of TF2

The stability of TF2 in human sera was assessed using BIACORE®. TF2 was diluted to 0.1 mg/ml in fresh human serum and incubated at 37° C. under 5% $CO_2$ for seven days. Daily samples were diluted 1:25 and then analyzed by BIACORE® using an IMP239 HSG sensorchip. An injection of WI2 IgG was used to quantify the amount of intact and fully active TF2. Serum samples were compared to control samples that were diluted directly from the stock. TF2 was highly stable in serum, retaining 98% of its bispecific binding activity after 7 days (not shown).

Example 4

Production of AD- and DDD-Linked Fab and IgG Fusion Proteins from Multiple Antibodies Using the techniques described in the preceding Examples, the IgG and Fab fusion proteins shown in Table 5 were constructed and incorporated into DNL® complexes. The fusion proteins retained the antigen-binding characteristics of the parent antibodies and the DNL® complexes exhibited the antigen-binding activities of the incorporated antibodies or antibody fragments.

TABLE 5

Fusion proteins comprising IgG or Fab

| Fusion Protein | Binding Specificity |
|---|---|
| C-AD1-Fab-h679 | HSG |
| C-AD2-Fab-h679 | HSG |
| C-(AD)$_2$-Fab-h679 | HSG |
| C-AD2-Fab-h734 | Indium-DTPA |
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

The skilled artisan will realize that the DNL® technique may be applied to produce multimeric complexes comprising any combination of antibodies, antibody fragments and/or other therapeutic agents, such as anti-HIV therapeutic agents. The Examples herein demonstrate that antibodies or fragments thereof may be incorporated into DNL® complexes without any impairment of the antibody binding characteristics, compared to the parent antibodies.

Example 5

Production and Use of Multivalent DNL® Complexes

Multivalent antibodies, either monospecific or bispecific, may improve the efficacy of current therapeutic interventions involving a single monoclonal antibody (mAb). Multivalent anti-CD20 antibody antibodies were generated from veltuzumab (hA20, see U.S. Pat. Nos. 7,151,164; 7,435,803; 7,919,273). We applied the DNL® method to prepare a hexavalent, anti-CD20 antibody, designated Hex-hA20, which comprises six Fabs with one Fc. We showed that Hex-hA20 retained the binding activity of all six Fabs, associated with CD20 in lipid rafts, affected antibody-dependent cell-mediated cytotoxicity, but not complement-dependent cytotoxicity, and inhibited proliferation of Daudi, Raji, and Ramos cells in vitro at subnanomolar concentrations without the need for a cross-linking antibody (Rossi et al., 2008, Cancer Res 68:8384-92). In addition, Hex-hA20 induced strong homotypical adhesion and was inefficient in stimulating calcium mobilization (Id.) Thus, Hex-hA20 exhibited biological properties attributable to both type I and type II anti-CD20 mAbs, as exemplified by rituximab and tositumomab, respectively. Although Hex-hA20 has a short serum half-life, it showed antitumor efficacy in tumor-bearing mice comparable with veltuzumab at equivalent doses (Id.)

The DNL® method was also applied to generate two other multivalent anti-CD20 antibodies without the Fc region, Tri-hA20 and Tetra-hA20, comprising three and four Fabs of veltuzumab, respectively. Similar to Hex-hA20, these were purified to near homogeneity and shown to have potent anti-proliferative activity in vitro (Id.), thus indicating the need for clustering three or more CD20 molecules on the cell surface to induce growth inhibition.

Materials and Methods

Cell Lines.

Daudi, Raji, and Ramos were purchased from the American Type Culture Collection. Sp/ESF, a variant of Sp2/0-Ag14 engineered to grow in serum-free medium, was used as the host cell for transfection.

Generation of Hex-hA20.

The expression vector encoding $C_{H1}$-DDD2-Fab-hA20 was generated from the $C_{H3}$-AD2-IgG-hA20-pdHL2 by excising the coding sequence for the $C_{H1}$-Hinge-$C_{H2}$-$C_{H3}$ domains with SacII and EagI and replacing it with a 507-bp sequence encoding $C_{H1}$-DDD2, which was excised from the C-DDD2-hMN-14-pdHL2 expression vector (as described in Example 2 above) with the same enzymes. The expression vector $C_{H3}$-AD2-IgG-hA20-pdHL2 or $C_{H1}$-DDD2-Fab-hA20-pdHL2, each 30 µg, was linearized by digestion with SalI and transfected into Sp/ESF (2.8×10$^6$ cells) by electroporation (450 V, 25 µF). The pdHL2 vector contains the gene for dihydrofolate reductase, thus allowing clonal selection, as well as gene amplification, with methotrexate (MTX). After transfection, the cells were plated in 96-well plates and selected in media containing 0.2 µmol/L MTX. Clones were screened for $C_{H3}$-AD2-IgG-hA20 or $C_{H1}$-DDD2-Fab-hA20 productivity by a sandwich ELISA using 96-well microtiter plates coated with WR2 (rat anti-idiotype antibody to veltuzumab) to capture the fusion protein, which was detected with horseradish peroxidase-conjugated goat anti-human IgG F(ab')$_2$. Wells giving the highest signal were expanded and ultimately used for production.

$C_{H3}$-AD2-IgG-hA20 and $C_{H1}$-DDD2-Fab-hA20 were produced in roller bottles, purified by affinity chromatography on Protein A and Protein L, respectively, and stored in PBS. To generate Hex-hA20, a mixture of $C_{H1}$-DDD2-Fab-hA20 (134 mg) and $C_{H3}$-AD2-IgG-hA20 (100 mg) was treated with 1 mmol/L reduced glutathione at room temperature for 16 h, followed by 2 mmol/L oxidized glutathione for 24 h, from which Hex-hA20 was purified by Protein A. DNL®-20/14 was made similarly by reacting $C_{H3}$-AD2-IgG-hA20 with $C_{H1}$-DDD2-Fab-hMN-14.

Generation of Tetra-hA20 and Tri-hA20.

Tetra-hA20 was obtained by purifying the tetrameric form of $C_{H1}$-DDD2-Fab-hA20 over a SUPERDEX™-200 column. Tri-hA20 was obtained by linking the dimeric form of $C_{H1}$-DDD2-Fab-hA20 covalently to $C_{H1}$-AD2-Fab-hA20, which was produced as described in Example 2 above for h679-Fab-AD2.

Competition ELISA.

Microtiter plates were coated overnight with veluzumab at 5 µg/mL and blocked with PBS containing 2% bovine serum albumin (BSA) for 1 h. Hex-hA20 and veltuzumab, serially diluted in triplicate, were each mixed with WR2 at 1 nmol/L and added to the coated wells. The bound WR2 was quantified with peroxidase-conjugated goat anti-rat IgG and O-phenylenediamine dihydrochloride.

Flow Cytometry.

Apoptosis, viable cell counting, cell binding, and off-rate measurements were performed by flow cytometry on a GUAVA® PCA (Guava Technologies, Inc.) using the manufacturer's reagents, protocols, and software.

Scatchard Analysis.

The maximum number of binding sites per cell and the apparent affinity constants were determined by nonlinear regression analysis of the saturation binding data obtained with radio-iodinated samples and Raji cells using PRISM® software (GRAPHPAD® Software, Inc.). Samples were run in triplicate. Immunoreactivity of each radiolabeled preparation was 90% or greater, as measured by binding to WR2.

Cell Proliferation Assay.

The in vitro cytotoxicity was determined using 3-(4,5-dimethylthiazol-2-yl)-5-(3-carboxymethoxyphenyl)-2-(4-sulfophenyl)-2H-tetrazolium (MTS), which is chemically reduced by metabolically active cells into formazan, and the intensity of the resulting color is proportional to the number of living cells.

CDC.

Cells were seeded in black 96-well microtitre plates at $5 \times 10^4$ cells in 50 µL/well and incubated with serial dilutions (concentration range, $3.33 \times 10^{-8}$ to $2.6 \times 10^{-10}$ mol/L) of test and control mAbs in the presence of human complement (1:20 final dilution) for 2 h at 37° C. and 5% $CO_2$. Viable cells were then quantified using the VYBRANT™ Cell Metabolic Assay Resazurin kit (Invitrogen). Controls included cells treated with 0.25% Triton X-100 (100% lysis) and cells treated with complement alone (background).

ADCC.

Daudi cells were incubated with each test article in triplicate at 5 µg/mL for 30 min at 37° C. and 5% $CO_2$. Freshly isolated peripheral blood mononuclear cells obtained from healthy volunteers were then added at a predetermined optimal effector to target ratio of 50:1. After a 4-h incubation, cell lysis was assessed by CYTOTOX-ONE™ (Promega).

Calcium Mobilization.

Intracellular calcium was measured in Ramos cells loaded with 20 µmol/L Fluo-3 AM (Invitrogen) using a Becton Dickinson FACSCAN® and the FlowJo program (Tree Star, Inc.). For all samples, a baseline was obtained for 60 s before adding each test article, which includes ionomycin and anti-human IgM as positive controls. To evaluate the effect of cross-linking, cells were incubated with 1 µg/mL of veltuzumab, rituximab, or tositumomab for further 15 min and stimulated with an appropriate second antibody (50 µg/mL final).

Homotypical Adhesion.

Daudi cells ($1.5 \times 10^6$/mL) were treated with veltuzumab, Tri-hA20, Tetra-hA20, or Hex-hA20 at 1 nmol/L for 20 h and then examined with an inverted phase-contrast microscope. The results were scored semiquantitatively according to Polyak and Deans (2002, Blood 99:3256-62).

Animal Studies.

The pharmacokinetic analysis was performed in naive female Swiss-Webster mice and compared with Hex-hA20 and veltuzumab given either i.v. or s.c. using radio-iodinated samples. The in vivo efficacy was evaluated in tumor-bearing SCID mice. Depletion of natural killer (NK) cells and neutrophils was performed as described (Hernandez-Ilizaliturri et al., 2003, Clin Cancer Res 9:5866-73), with the following modifications. Briefly, mice received i.p. injections of anti-mouse Gr-1 ascites (100 µL) and TMβ-1 mAb (100 µg) 1 d before inoculating Raji cells and three more weekly i.p. injections of antimouse Gr-1 ascites on days 6, 13, and 20 to maintain neutrophil depletion, which was confirmed by fluorescence-activated cell sorting analysis of blood samples taken from one treated and one untreated mouse on days 3, 13, and 20. Mice deemed to have succumbed to disease progression, when hind-limb paralysis developed or if they otherwise became moribund, were humanely sacrificed. Additionally, if mice lost >20% of initial body weight, they were sacrificed. Survival curves were analyzed using Kaplan-Meier plots (log-rank analysis) and PRISM® software.

Results

Hexavalent Antibodies Made by DNL®.

Hex-hA20 was readily obtained by mixing $C_{H1}$-DDD2-Fab-hA20 and $C_{H3}$-AD2-IgG-hA20 under redox conditions followed by purification with Protein A. Both $C_{H1}$-DDD2-Fab-hA20 and $C_{H3}$-AD2-IgG-hA20 were produced with good yields as fusion proteins in myeloma cells, with subsequent purification from culture supernatants by Protein L and Protein A, respectively.

The purity of Hex-hA20 by reducing SDS-PAGE showed only three bands from the constitutive polypeptides (data not shown). Nonreducing SDS-PAGE analysis of Hex-hA20 confirmed its covalent structure, because no bands corresponding to the monomeric form of $C_{H3}$-AD2-IgG-hA20 were observed (not shown). The molecular mass of Hex-hA20 was determined to be 368,475 Da by MALDI-TOF mass spectrometry, which agrees well with the calculated molecular weight of 362 kDa for Hex-hA20 from the deduced amino acid sequences of the constituent polypeptides.

Binding Analysis.

Figure 3:
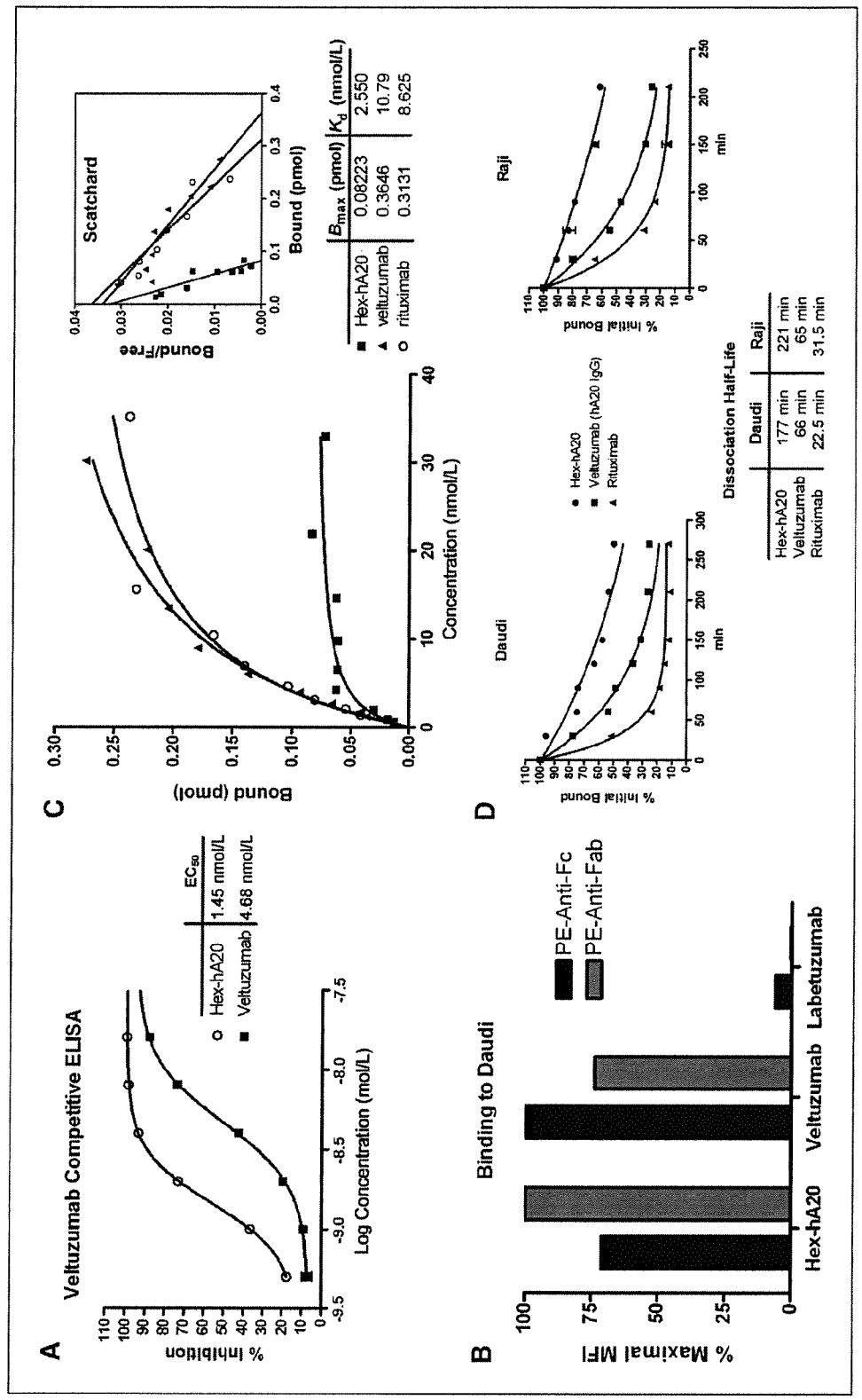
FIG. 3. Analysis of Hex-hA20 binding. (A) Competition ELISA showing Hex-hA20 has a higher avidity than veltuzumab for binding to WR2. Hex-hA20 (○) or veltuzumab (■) were incubated at varying concentrations in the presence of WR2 for competition of binding with immobilized veltuzumab. The percentage of inhibition was plotted versus mAb concentration, and $EC_{50}$ values were generated with PRISM® software. (B) Binding to Daudi cells as determined by flow cytometry using PE-conjugated anti-human Fab (PE-anti-Fab) or PE-conjugated anti-human Fc (PE-anti-Fc). All incubations and washes were performed at 4° C. Daudi cells were suspended at $1\times10^6$ cells/mL in 1% BSA-PBS and incubated with Hex-hA20, veltuzumab, or labetuzumab for 1 h. The cells were washed with 1% BSA-PBS, incubated with a 1:200 dilution of PE-anti-Fab or PE-anti-Fc for 30 min, washed once more, and analyzed on a GUAVA® PCA. (C) Scatchard analysis using radio-iodinated Hex-hA20 (■), veltuzumab (▲), or rituximab (○) and Raji cells. (D) Dissociation from Daudi or Raji cells. Hex-hA20 (•), veltuzumab (■), and rituximab (▲) were labeled with PE using a ZENON® R-phycoerythrin Human IgG Labeling kit (Invitrogen Corp.). Cells were suspended in CM (phenol red-free RPMI 1640 supplemented with 10% FBS at $1\times10^6$ cells/mL), and $5\times10^5$ cells were incubated with each PE-labeled antibody at 65 nmol/L for 30 min at room temperature. The cells were washed twice with CM to remove unbound antibody, resuspended in 1.5 mL of CM in the presence of 1 µmol/L $C_{H1}$-DDD2-Fab-hA20 at 37° C., and analyzed for cell-bound PE-labeled antibody at several time points on a GUAVA® PCA. The dissociation half-life was determined by nonlinear regression using PRISM® software.

As shown by competition ELISA (FIG. 3A), Hex-hA20 has a 3-fold higher avidity than veltuzumab, suggesting that at least three or more of the six Fab components are capable of binding simultaneously to the WR2 antiidiotype antibody. The binding of Hex-hA20 to CD20 on live cells was compared with that of veltuzumab by flow cytometry. Hex-hA20 resulted in 40% to 50% greater fluorescence intensity than veltuzumab when probed by PE-anti-Fab (FIG. 3B). In contrast, the signal observed for Hex-hA20 with PE-anti-Fc was lower than that of veltuzumab. These results are consistent with Hex-hA20 having four more Fabs than veltuzumab, but only one Fc like veltuzumab.

Additional evidence for the higher valency and avidity of Hex-hA20 is provided by Scatchard analysis of binding to Raji cells (FIG. 3C), which showed that the apparent association constant of Hex-hA20 [$\sim 3.9 \times 10^8$ $(mol/L)^{-1}$] was ~4-fold higher (P<0.0001) than that of veltuzumab [$\sim 1 \times 10^8$ $(mol/L)^{-1}$], whereas an F test determined that the saturation binding curves for rituximab and veltuzumab were similar (P=0.1859). More importantly, the number of receptors per cell calculated from the maximum number of binding sites ($B_{max}$) obtained for Hex-hA20 was found to be ~¼ of that obtained with veltuzumab (~100,000 versus ~437,5000), suggesting that all six Fabs of Hex-hA20 are capable of binding to CD20 on the cell surface, because the same number of CD20 molecules would require three times as many veltuzumab to occupy them. The data obtained from the off-rate measurements (FIG. 3D) also indicated that Hex-hA20 dissociates ~3-fold slower than veltuzumab, which dissociates ~2-fold to 3-fold slower than rituximab (Glennie et al., 2007, Mol Immunol 44: 3823-37).

Antiproliferative Activity.

Based on the MTS assay (FIG. 4A), Hex-hA20 strongly inhibited proliferation in three Burkitt lymphoma cell lines, Raji, Ramos, and Daudi, with an $EC_{50}$ of 0.064, 0.15, and 0.15 nmol/L, respectively. In contrast, veltuzumab in the absence of a cross-linking antibody showed detectable potency in all three cell lines only at >10 nmol/L. As expected, cross-linking of veltuzumab with goat anti-human Fc resulted in significant inhibition of proliferation. For Hex-hA20, cross-linking did not increase its potency further in Daudi. Additional experiments compared the effects of Hex-hA20, Tri-hA20, and Tetra-hA20 on cell proliferation over 5 days by viable cell counting. Representative results are shown in FIG. 4B for Raji and Ramos, which show the ability of Tri-hA20, Tetra-hA20, and Hex-hA20 to prevent 50% or greater cell proliferation without cross-linking at concentrations as low as 0.5 nmol/L. Similar results were obtained for Daudi (data not shown). The cell counting assay also showed that Hex-hA20 ($EC_{50}$=0.17 nmol/L) was considerably more potent than anti-B1 ($EC_{50}$=4.65 nmol/L) when evaluated with Ramos for 3 days.

Apoptosis and the Roles of Caspases and Calcium.

Figure 5:
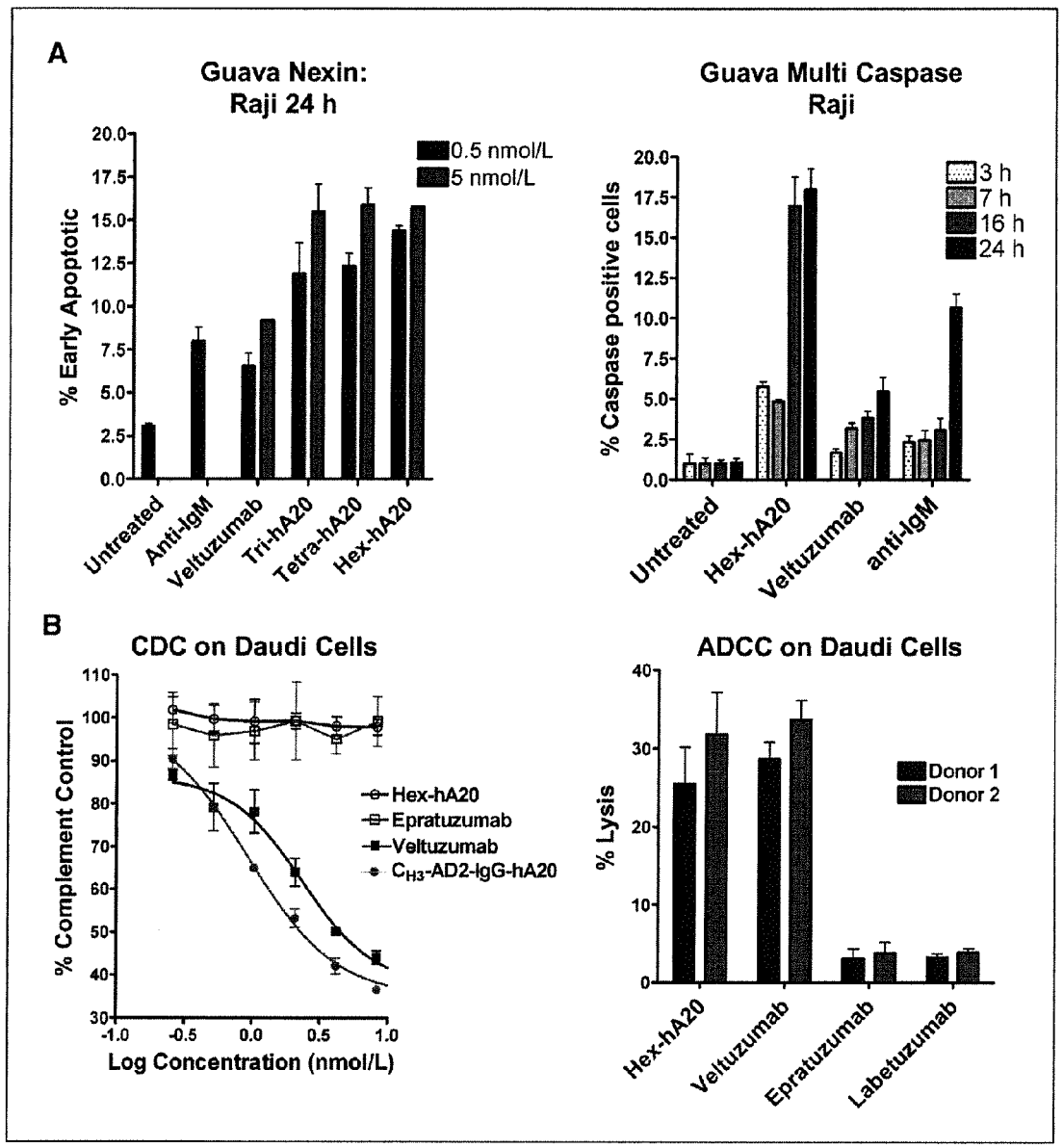
FIG. 5 (A) Apoptosis measured by GUAVA® Nexin (left) showing percentage of early apoptotic cells (Annexin V-PE positive/7-AAD negative) induced in Raji after 24-h incubation with veltuzumab, Tri-hA20, Tetra-hA20, or Hex-hA20 at 0.5 nmol/L (black columns) or 5 nmol/L (gray columns). Apoptosis measured by GUAVA® MultiCaspase (right) for which Raji cells were cultured in the presence of Hex-hA20 (5 nmol/L), veltuzumab (5 nmol/L), or anti-IgM (5 µg/mL) and analyzed at 3, 7, 16, and 24 h by flow cytometry after staining with SR-VAD-FMK. Cells were plated at $2\times10^5$ cells/mL in fresh media and incubated at 37° C. with each test article at the indicated concentrations for up to 24 h, and duplicate wells were processed for GUAVA® analysis. (B) CDC (left) was measured in Daudi cells for Hex-hA20 (○), epratuzumab (□), veltuzumab (■), or $C_{H3}$-AD2-IgG-hA20 (✻) in the presence of human complement. The percentage complement control (number of viable cells in the test sample compared with cells treated with complement only) was plotted versus the log of the nanomolar concentration. ADCC (right) was measured for Hex-hA20, veltuzumab, epratuzumab, or labetuzumab at 5 µg/mL using Daudi as the target cells and freshly isolated peripheral blood mononuclear cells from two donors as the effector cells. A 100% lysis reference was generated by the addition of detergent to wells containing target cells only. The bar graphs show percentage of lysis obtained for each of the two donors.

Raji cells were treated with the three multivalent anti-CD20 constructs at 0.5 or 5 nmol/L and analyzed with the GUAVA® Nexin assay after 24 hours (FIG. 5A, left). Treatment with Tri-hA20, Tetra-hA20, or Hex-hA20 resulted in more cells in early apoptosis (12-16%) compared with the bivalent veltuzumab (6-9%) and the untreated control (3%). Comparable results were obtained with Daudi and Ramos cells (data not shown).

The extent of apoptosis was also assessed for Raji cells treated with 5 nmol/L Hex-hA20 or veltuzumab over a 24-hour period using the GUAVA® MultiCaspase assay (FIG. 5A, right). The results at 24 hours were 17% and 6% for Hex-hA20 and veltuzumab, respectively, which agree with those determined by the GUAVA® Nexin assay.

The effect of Z-VAD-FMK (a broad-spectrum caspase inhibitor) on apoptosis induced by Hex-hA20 was examined in Ramos, and the results (not shown) indicated that Z-VAD-FMK at 100 µmol/L completely prevented the apoptosis induced by antihuman IgM, but not that induced by Hex-hA20, suggesting that both caspase-dependent and caspase-independent pathways occur for Hex-hA20. Although CD20 clustering is presumably achievable either indirectly by cross-linking the antigen-bound veltuzumab with a second antibody or directly via multivalent engagement of Hex-hA20, the former, but not the latter, leads to a rapid rise in intracellular calcium levels (not shown).

Effector Functions.

CDC activity was evaluated in vitro using human complement and Daudi cells (FIG. 5B, left). Veltuzumab exhibited potent CDC activity. Surprisingly, Hex-hA20 failed to induce CDC in Daudi cells. Because $C_{H3}$-AD2-IgG-hA20 induces CDC with similar potency as veltuzumab, modification of the carboxyl termini of veltuzumab by the addition of the small AD2 peptide does not affect CDC, suggesting that the addition of the four Fab-DDD2 groups apparently prevents complement fixation, despite the ability of Hex-hA20 to bind C1q (data not shown). Hex-hA20 and veltuzumab have comparable ADCC (FIG. 5B, right). Thus, the Fc of Hex-hA20 induces ADCC.

Homotypical Adhesion.

Hex-hA20, Tetra-hA20, and Tri-hA20 induced homotypical adhesion of Daudi cells, resulting in >50% of cells having medium-size to large-size aggregates, whereas under the same conditions, the extent of cell aggregation observed for veltuzumab was similar to that of the untreated control (not shown).

Membrane Localization of CD20/Hex-hA20.

The distribution of CD20 at the cell surface upon binding to veltuzumab or Hex-hA20 was examined with immunofluorescence microscopy using cholera toxin subunit B-Alexa Fluor 488 as the reporter for ganglioside GM-1, a common lipid raft marker. Incubation of Daudi cells with veltuzumab or Hex-hA20 led to the formation of membrane patches or caps with punctuate spots, which were superbly matched by the images obtained with cholera toxin subunit B, indicating the localization of CD20 in lipid rafts (not shown). Although the fluorescent patterns observed were similar, veltuzumab seemed to form larger and fewer patches than Hex-hA20 (not shown).

Serum Stability.

Hex-hA20 was found to have the same stability in serum as veltuzumab, maintaining 86% binding activity after 11 days (not shown). These results are similar to those of the bispecific Tri-Fab complexes reported previously (Rossi et al., 2006, Proc. Natl Acad Sci USA 103; 6841-6).

Pharmacokinetic Analysis.

Using radio-iodinated preparations, it was found that Hex-hA20 cleared ~4.5 times faster than veltuzumab when given i.v. (not shown), resulting in a 3.7-fold lower mean residence time for Hex-hA20 compared with veltuzumab (127 hours versus 472 hours). When given s.c., Hex-hA20 cleared at a much faster rate ($T_{1/2}$~3 days) than veltuzumab ($T_{1/2}$>9 days), with both having the same $T_{max}$ of 24 hours (not shown). However, the $C_{max}$ was only half as high for Hex-hA20 compared with veltuzumab (12.9 nmol/L versus 25.7 nmol/L).

In Vivo Efficacy.

Figure 6:
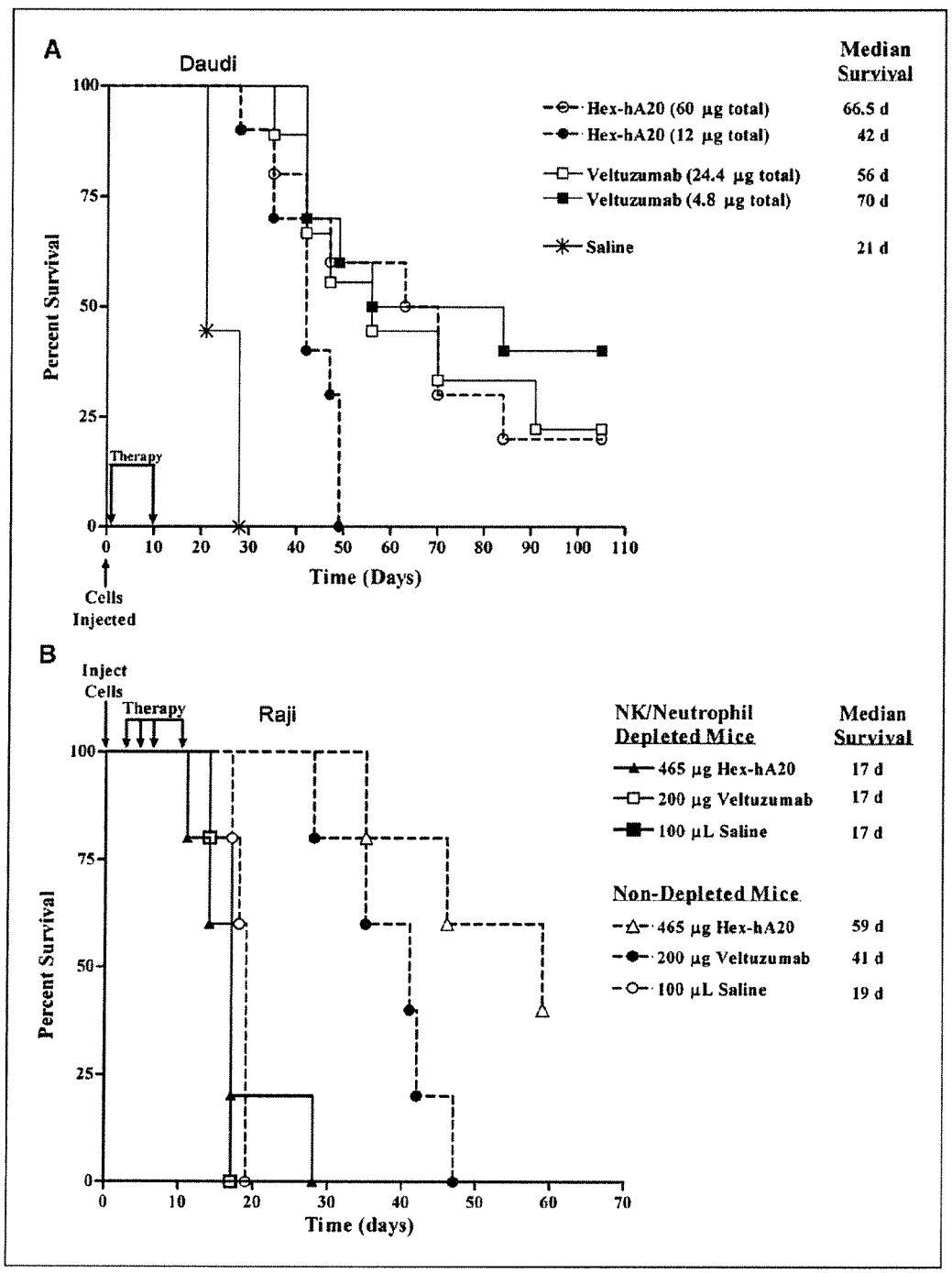
FIG. 6. Efficacy of Hex-hA20 in human lymphoma xenograft models. (A) Daudi cells ($1.5\times10^7$) were injected i.v. into SCID mice on day 0. On days 1 and 8, groups of mice (n=9-10) were given either Hex-hA20 at two different doses (30 or 6 µg) or equimolar amounts of veltuzumab (12.4 or 2.4 µg). (B) SCID mice were depleted of NK cells and neutrophils before the administration of Raji cells with antimouse Gr-1 ascites and TMβ-1 mAb specific for mouse IL-2 receptor, as described in Materials and Methods. On day 0, Raji cells ($1\times10^6$) were injected i.v. into both depleted and nondepleted mice. Hex-hA20 (465 µg) or veltuzumab (200 µg) was given i.v. on days 3, 5, 7, and 11, whereas the control group received saline.

In the multiple-dose study with the Daudi model, mice were treated with Hex-hA20 at 30 µg (q7dx2) and 6 µg (q7dx2). As shown in FIG. 6A, both treatments resulted in significantly improved median survival time (MST) when compared with the saline control (66.5 and 42 versus 21 days; P<0.0001). Although no significant difference in survival was observed between mice given Hex-hA20 and veltuzumab at the higher doses, it seemed that mice receiving Hex-hA20 at the lower doses had significantly lower MST than those receiving veltuzumab at an equivalent dose (P=0.0044).

We also examined the role of effector cells in inhibiting tumor growth using the Raji model (FIG. 6b). In those animals depleted of NK cells and neutrophils, there was no difference between the saline control and mice treated with veltuzumab or Hex-hA20 (MST=17 days for all three groups). In contrast, nondepleted mice that received Hex-hA20 or veltuzumab had significantly improved survival than the saline control (P=0.0034), with the MST of 59, 41, and 19 days for Hex-hA20, veltuzumab, and untreated, respectively. Importantly, a better treatment outcome was observed for Hex-hA20 than for veltuzumab (P=0.05) at this higher mole-equivalent dose (465 µg Hex-hA20 versus 200 µg veltuzumab).

Discussion

The fact that Tri-hA20, but not veltuzumab, can potently inhibit the proliferation of CD20-positive cells in vitro is consistent with the model that all three Fabs in Tri-hA20 are capable of simultaneously binding to CD20, resulting in clustering of CD20 and the onset of signal transduction, which leads us to conclude that a minimum valency of 3 is required for an anti-CD20 antibody to effectively induce growth inhibition without cross-linking Based on their efficacy in certain in vitro assays, anti-CD20 mAbs have been classified by Cragg and colleagues (Cragg et al., 2003, Blood 101:1045-52) as either type I, represented by rituximab, or type II, represented by tositumomab. We note that Hex-hA20 exhibits biological properties attributable to both type II (for example, negative for CDC and calcium mobilization; positive for antiproliferation, apoptosis, and homotypical adhesion) and type I (for example, positive for trafficking to lipid rafts). Thus, one effective approach to converting a type I anti-CD20 mAb to a type B can be achieved by making the type I mAb multivalent, Preliminary investigation of the signaling pathway indicates that Hex-hA20 induces caspase-dependent, as well as caspase-independent, apoptosis. Additional studies are in progress to identify the subcellular events associated with the binding of CD20 by Hex-hA20 or Tri-hA20, which may reveal unequivocally the molecular factors that account for the antiproliferative potency of a multivalent anti-CD20 antibody with defined composition.

These results demonstrate that production of multivalent antibodies by the DNL® methodology produces superior efficacy. The skilled artisan will realize that multivalent DNL® complexes comprising one or more anti-HIV antibodies or fragments thereof, such as P4/D10, 2G12, 2F5 or 4E10, may be constructed using the same technique.

Example 6

PEGylated DNL® Complexes

In certain embodiments, PEG moieties may be incorporated into DNL® complexes, for example to provide for a reproducible and homogeneous PEGylated product of an effector moiety. As a first step, the following peptide subunits capable of covalent conjugation to PEG moieties for incorporation into DNL® complexes were synthesized on a commercial peptide synthesizer. Fmoc-Cys(t-Buthio)-OH was used to add the SS-tbu residue. Fmoc-Gly-EDANS resin was used to attach the G-EDANS moiety.

```
IMP350
                                          (SEQ ID NO: 93)
CGQIEYLAKQIVDNAIQQAGC(SS-tbu)-NH2

IMP360
                                          (SEQ ID NO: 94)
CGQIEYLAKQIVDNAIQQAGC(SS-tbu)-G-EDANS IMP421
                                          (SEQ ID NO: 95)
Ac-C-PEG3-C(S-tBu)GQIEYLAKQIVDNAIQQAGC(S-tBu)G-NH2
```

Generation of IMP362, IMP413 and IMP457

The two linear PEG-AD2 modules were prepared by coupling IMP360 to mPEG-OPTE (Nectar Therapeutics, San Carlos, Calif.) of 20-kDa or 30-kDa, resulting in IMP362 or IMP413, respectively. To prepare IMP362, IMP360 (11.5 mg) was mixed with 20-kDa mPEG-OPTE (127 mg) in 7 mL of 1 M Tris-HCL, pH 7.8. Acetonitrile (1 mL) was added to dissolve some suspended material. The reaction was stirred at room temperature for 4 h to effect the attachment of mPEG to the amino-terminal cysteine via an amide bond. Subsequently, 41 mg of Tris[2-carboxyethyl]phosphine hydrochloride (TCEP) and 43 mg of cysteine were added to de-protect the remaining cysteine. The reaction mixtures were stirred for 1 h and desalted using PD-10 columns, which had been equilibrated with 20% methanol in water. The samples were lyophilized to obtain approximately 150 mg of IMP362. IMP413 was made similarly using 30-kDa mPEG-OPTE (190 mg). IMP457 was made similarly using mPEG2-MAL-40K (Nectar Therapeutics) to obtain the branched PEG-AD2 module (IMP457).

Construction of IFN-α2b-DDD2-pdHL2 for Expression in Mammalian Cells

The cDNA sequence for IFN-α2b was amplified by PCR using a full length human IFNα2b cDNA clone (Invitrogen ULTIMATE™ ORF human clone cat# HORF01Clone ID IOH35221) as a template and the following oligonucleotides as primers:

```
IFNA2 Xba I Left
                                          (SEQ ID NO: 96)
5'-TCTAGACACAGGACCTCATCATGGCCTTGACCTTTGCTTTACTGG-3'

IFNA2 BamHI right
                                          (SEQ ID NO: 97)
5'-GGATCCATGATGGTGATGATGGTGTGACTTTTCCTTACTTCTTAAACTTTCTTGC-3'
```

The resulting secreted protein consists of IFN-α2b fused at its C-terminus to a polypeptide consisting of SEQ ID NO:98.

```
                                          (SEQ ID NO: 98)
KSHHHHHHGSGGGGSGGGCGHIQIPPGLTELLQGYTVEVLRQQPPDLVEF

AVEYFTRLREARA
```

The PCR amplimer was cloned into the pGEM®-T vector. A DDD2-pdHL2 mammalian expression vector was prepared for ligation with IFN-α2b by digestion with XbaI and Bam HI restriction endonucleases. The IFN-α2b amplimer was excised from PGEMT® with XbaI and Bam HI and ligated into the DDD2-pdHL2 vector to generate the expression vector IFN-α2b-DDD2-pdHL2.

IFN-α2b-DDD2-pdHL2 was linearized by digestion with SalI enzyme and stably transfected into Sp/EEE myeloma cells by electroporation for producing the expressed protein (see. e.g., U.S. Pat. No. 7,537,930, the Examples section of which is incorporated herein by reference).

Preparation and Purification of α2b-362 (IFN-α2b-DDD2-IMP362)

The structure of α2b-362 has two copies of IFNα2b-DDD2 coupled to a 20 kDa PEG-AD. A DNL® reaction was performed by the addition of 11 mg of reduced and lyophilized IMP362 in 10-fold molar excess to 2.25 mg (3.5 ml) of IFN-α2b-DDD2 in 250 mM imidazole, 0.02% Tween 20, 150 mM NaCl, 1 mM EDTA, 50 mM NaH$_2$PO$_4$, pH 7.5. After 6 h at room temperature in the dark, the reaction mixture was dialyzed and purified by column chromatography on a cation-exchange resin.

The DNL® reaction resulted in the site-specific and covalent conjugation of IMP362 with a dimer of IFN-α2b. Overall, the DNL® reaction resulted in a near quantitative yield of a homogeneous product that was >90% pure after purification by cation-exchange chromatography (not shown).

The PEGylated products α2b-457 (IFN-α2b-DDD2-IMP457) and α2b-413 (IFN-α2b-DDD2-IMP413) were prepared by similar techniques.

Pharmacokinetics

The study was performed in adult female Swiss-Webster mice (~35 g). Each reagent (test and control) was administered at equimolar protein doses (3 μg of rhuIFN-α2a, 5 μg of PEGINTRON®, 11 μg of α2b-362, and 13 μg of α2b-413) as a single bolus i.v. injection. Mice were bled via the retro-orbital method at various time-points (pre-dose, 5-min, 2-, 8-, 24-, 48-, 72-, 96-, and 168-h post-injection). The blood was allowed to clot, centrifuged, and the serum was isolated and stored at −70° C. until assayed for IFN-α concentration and subsequent PK-analysis.

The PK properties of each agent are summarized in Table 6. As expected, rhIFN-α2a had the most rapid clearance from the blood of injected mice. Its clearance was approximately 3-fold faster than the PEGINTRON® and more than 13-fold faster than the DNL®-IFN reagents. The PEGINTRON® was in turn cleared greater than 4-fold faster than α2b-362 or α2b-413. There was little difference in the elimination rates between α2b-362 and α2b-413.

In terms of mean residence time (MRT), there is a clear correlation with size among the various reagents. The 19-kDa rhIFN-α2a had a MRT that was 7-fold less than the 31 kDa PEGINTRON® (0.7 h versus 5.1 h, respectively), which had a 2-fold lower MRT when compared to the 70 kDa α2b-362 (10.3 h). The MRT for the 80 kDa α2b-413 (21.7 h) was 2-fold longer than α2b-362. Finally, a test for bioequivalence showed that none of the reagents tested were the same in terms of PK, indicating that the differences are genuine (i.e., circulating half-life for α2b-413>α2b-362>PEGINTRON®>rhIFN-α2a).

Survival curves were generated. PEGINTRON®, α2b-362, and α2b-413 all demonstrated significant improvement in survival when compared to saline control mice (P<0.0016) (not shown). Except for the 3,500 IU dose of α2b-362, both α2b-413 and α2b-362 were superior to PEGINTRON® when administered at equal activity doses (P≤0.0027) (not shown). α2b-362 showed more than twice the potency of PEGINTRON® (not shown). Doses of 7,000 IU and 3,500 IU of α2b-362 were superior to 14,000 IU (P=0.0016) and 7,000 IU (P=0.0027) doses of PEGINTRON®, respectively (not shown). α2b-413 is more than four times as potent as PEGINTRON® since a 3,500 IU dose of the former was superior to 14,000 IU of the latter (P=0.0027) (not shown). α2b-413 was significantly better than α2b-362 (P<0.0025) when administered at equivalent doses. However, there were no statistically significant differences among the three doses of α2b-413, even though the 14,000 IU dose resulted in a median survival of 60 days in comparison to the 3,500 IU dose and its 46 day median survival (P=0.1255). The in vivo efficacy observed for α2b-362, α2b-413, and PEGINTRON® thus correlate well with the PK data.

The increased bioavailability of α2b-362 and α2b-413 demonstrated by PK analysis contributes to the enhanced in vivo anti-tumor potency of DNL®-PEGylated IFNα. In turn, these two factors allow for a less frequent dosing schedule used in tumor therapy. This was demonstrated with a similar in vivo tumor therapy study as above, in which equal units of activity of PEGINTRON® or α2b-413 were administered with varied dosing schedules. Each reagent (test and control) was administered at 14,000 IU via a s.c. injection in either the left or right flank.

TABLE 6

Blood Pharmacokinetic Analysis of Interferon-α2b Containing DNL Molecules Administered as Intravenous Injections to Naive Swiss-Webster Mice.

| Animal Number | IFN Dose (pmol) | $C_{max}$ (pM) | $T_{1/2\alpha}$ (hours) | $T_{1/2\beta}$ (hours) | $AUC_{0.08\to\infty}$ (h * pM) | Elimination Rate (1/h) | $MRT_{0.08\to\infty}$ (h) |
|---|---|---|---|---|---|---|---|
| Recombinant Human Interferon-α2a | | | | | | | |
| Animal No. 1 | 160 | 16,411 | 0.29 | 10.53 | 7,011 | 2.34 | 0.63 |
| Animal No. 2 | 160 | 21,835 | 0.31 | 7.14 | 10,147 | 2.15 | 0.78 |
| Mean | 160 | 19,123 | 0.30 | 8.84 | 8,579 | 2.25 | 0.71 |
| PEGINTRON ® | | | | | | | |
| Animal No. 1 | 160 | 87,090 | 0.53 | 6.29 | 137,790 | 0.63 | 5.42 |
| Animal No. 2 | 160 | 105,774 | 0.43 | 5.11 | 150,905 | 0.70 | 4.79 |
| Mean | 160 | 96,432 | 0.48 | 5.70 | 144,348 | 0.67 | 5.11 |
| IFN-α2b-IMP362 | | | | | | | |
| Animal No. 1 | 320 | 60,833 | 1.72 | 7.54 | 379,462 | 0.16 | 9.03 |
| Animal No. 2 | 320 | 97,089 | 1.43 | 10.14 | 570,336 | 0.17 | 11.56 |
| Mean | 320 | 78,961 | 1.58 | 8.84 | 474,899 | 0.17 | 10.30 |
| IFN-α2b-IMP413 | | | | | | | |
| Animal No. 1 | 320 | 152,923 | 0.69 | 12.85 | 1,012,470 | 0.15 | 16.75 |
| Animal No. 2 | 320 | 100,495 | 4.03 | 28.53 | 1,179,056 | 0.09 | 26.56 |
| Mean | 320 | 126,709 | 2.36 | 20.69 | 1,095,763 | 0.12 | 21.66 |

In Vivo Efficacy

An in vivo tumor therapy study demonstrated that the DNL®-PEGylated interferons were more potent and longer-lasting compared to PEGINTRON®. Eight-week-old female C.B.-17 SCID mice were injected i.v. with a human Burkitt's lymphoma cell-line (Daudi) at $1.5 \times 10^7$ cells per animal. Equivalent units of activity of PEGINTRON®, α2b-362 and α2b-413 were administered once every 7 days via s.c. injection in either the left or right flank at three different doses (3500, 7000, and 14000 Units). Therapy commenced 1 day after the Daudi cells were transplanted.

All the IFN-IMP413-treated mice had significantly improved survival when compared to those animals treated at the same schedule with PEGINTRON® (P<0.0097) (not shown). Of note, those mice treated every other week with IFN-IMP413 (q2wkx4) not only had significantly improved survival in comparison to those treated with PEGINTRON® at the same schedule (MST=>54 days versus 28 days, respectively; P=0.0002), but were also significantly better than those animals treated weekly (q7dx4) with PEGINTRON® (MST=36.5 days; P=0.0049) (not shown). Further, survival of mice treated every three weeks with IFN-IMP413

(q3wkx4) was significantly better than those treated with PEGINTRON® every two weeks (MST=54 days versus 28 days; P=0.002) and approaches significance when compared to those treated weekly with PEGINTRON® (P=0.0598) (not shown).

In another study, we found that administering α2b-413 at 14,000 IU every 4 weeks increased the median survival to 56 days from 23 days of the saline control and was more potent than PEGINTRON® given 14,000 IU every week (not shown).

For a better comparison with PEGASYS®, we conjugated IFNα2b-DDD2 to IMP457, an AD2-module of 40-kDa branched PEG, and obtained a resulting α2b-457. The in vitro biological activities of α2b-457 were determined by three different assays to be lower than PEGINTRON®, comparable to α2b-413, and considerably higher than PEGASYS® (not shown). The PK data obtained in mice with a single s.c. injection indicate a longer circulating half-life of α2b-457 than either α2b-413 or PEGASYS®, with all three clearing much slower than PEGINTRON® (not shown).

When given once every four weeks at a low dose of 20 pmol, α2b-457 was more effective than PEGINTRON® given as a mole-equivalent dose once weekly. Administration of α2b-457 extended the median survival of Daudi-bearing mice to 47 days from 23 days when compared to the saline group (not shown). In the same study, α2b-457 at 20 pmol was significantly better than either α2b-413 or PEGINTRON® at 20 pmol (MST=47 days versus 41 and 37 days, respectively; P<0.0151) (not shown). The 20 pmol dose of α2b-413 also improved survival in comparison to PEGINTRON® (P=0.002) (not shown). At 10 pmol, there was no difference between α2b-457 and α2b-413 but both significantly improved survival over PEGINTRON® treated mice (P<0.001) (not shown).

These studies demonstrated that PEGylation of therapeutic agents using the DNL® technique resulted in improved and long-lasting efficacy, even when compared with other PEGylated forms of IFNα2b, allowing for less frequent dosing. The skilled artisan will realize that DNL® PEG conjugates may provide similarly improved pharmacokinetics and/or efficacy for anti-HIV therapeutic agents.

Example 7

Anti-HIV DNL® Complex

Among the various antibodies that neutralize HIV-1, the murine anti-gp120 antibody, P4/D10, is distinguished by its ability to induce antibody-dependent cellular cytotoxicity (ADCC) to eliminate infected T cells that express the antigenic gp120 epitope bound by P4/D10 (Broliden et al., 1990, J Virol 64:936-40). Enhanced potency was also shown in Example 1 above for doxorubicin-conjugated P4/D10 to neutralize and inhibit intercellular spread of HIV infection in vitro, as well as to protect against HIV-1/MuLV infection in vivo (Johansson et al., 2006, AIDS 20:1911-15).

DOCK-AND-LOCK® (DNL®) method is used to generate a DNL® complex comprising P4/D10 IgG, or other anti-HIV antibodies or fragments thereof, along with one or more anti-HIV agents. In a preferred embodiment illustrated herein, the anti-HIV agent is the T20 HIV fusion inhibitor (enfuvirtide, FUZEON®) [Asboe, 2004, HIV Clin Trials 5:1-6). However, the skilled artisan will realize that other anti-HIV therapeutic agents known in the art, described in more detail above, may be utilized either attached to an anti-HIV DNL® complex or separately administered before, simultaneously with, or after an anti-HIV DNL® complex.

In a preferred embodiment illustrated in FIG. 8, the DNL® method is used to develop a novel class of anti-HIV agents that comprise multiple copies of enfuvirtide (T20) linked to a chimeric, human or humanized antibody with specificity for HIV-1, such as P4/D10. Such conjugates allow less frequent dosing than with unconjugated T20 to block entry of HIV-1 into T cells, neutralize free HIV-1 and eliminate HIV-infected cells. A schematic diagram showing such an exemplary DNL® construct is illustrated in FIG. 8. The C-terminal end of each heavy chain of an IgG antibody is attached via a short linker to an AD2 moiety (SEQ ID NO:4) and expressed as a fusion protein as described in the Examples above. The T20 HIV fusion inhibitor is attached to a DDD2 moiety (SEQ ID NO:2) and also expressed as a fusion protein. Two copies of the DDD2 moiety spontaneously form a dimer that binds to the AD2 moiety, forming a DNL® complex comprising one IgG antibody and four copies of T20 (FIG. 8).

The DDD2-T20 amino acid sequence is shown below in SEQ ID NO:99. The sequence of DDD2 is underlined. This is followed by a short linker and hinge region and a polyhistidine tag for affinity purification. The sequence of T20 at the C-terminal end is in bold. DDD2-T20 has been produced and used to make DNL® complexes, as described below.

DDD2-T20

(SEQ ID NO: 99)

MCGHIQIPPGLTELLQGYTVEVLRQQPPDLVEFAVEYFTRLREARAEFPKPSTPPGSSGH

HHHHHGSYTSLIHSLIEESQNQQEKNEQELLELDKWASLWNWF

Figure 7:
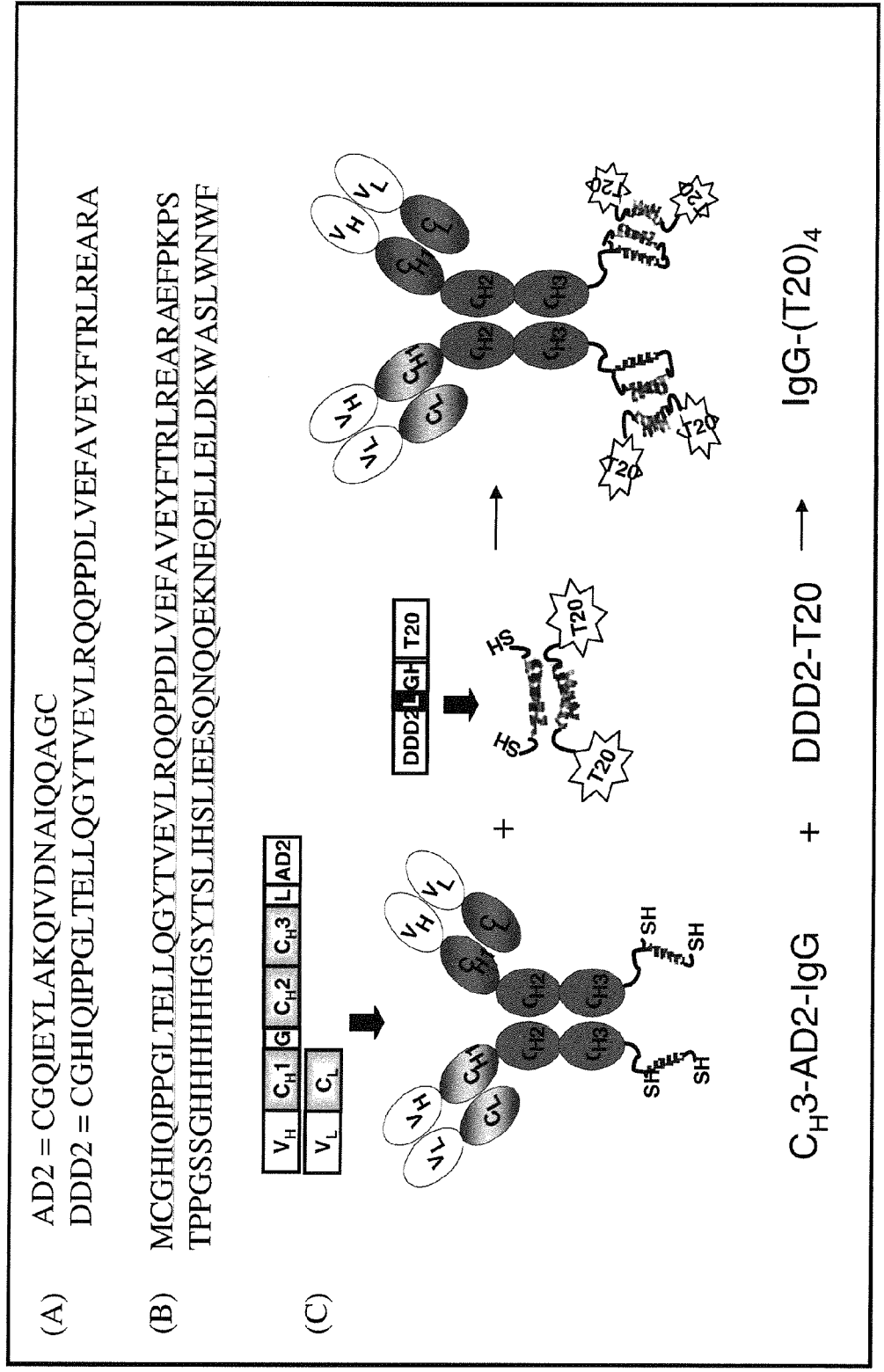
FIG. 7. In vitro activity of cP4/D10 versus murine P4/D10. Activity was measured as the ability to inhibit production of viral p24 protein (measured by ELISA) indicating HIV replication in PMBC.
Figure 10A:
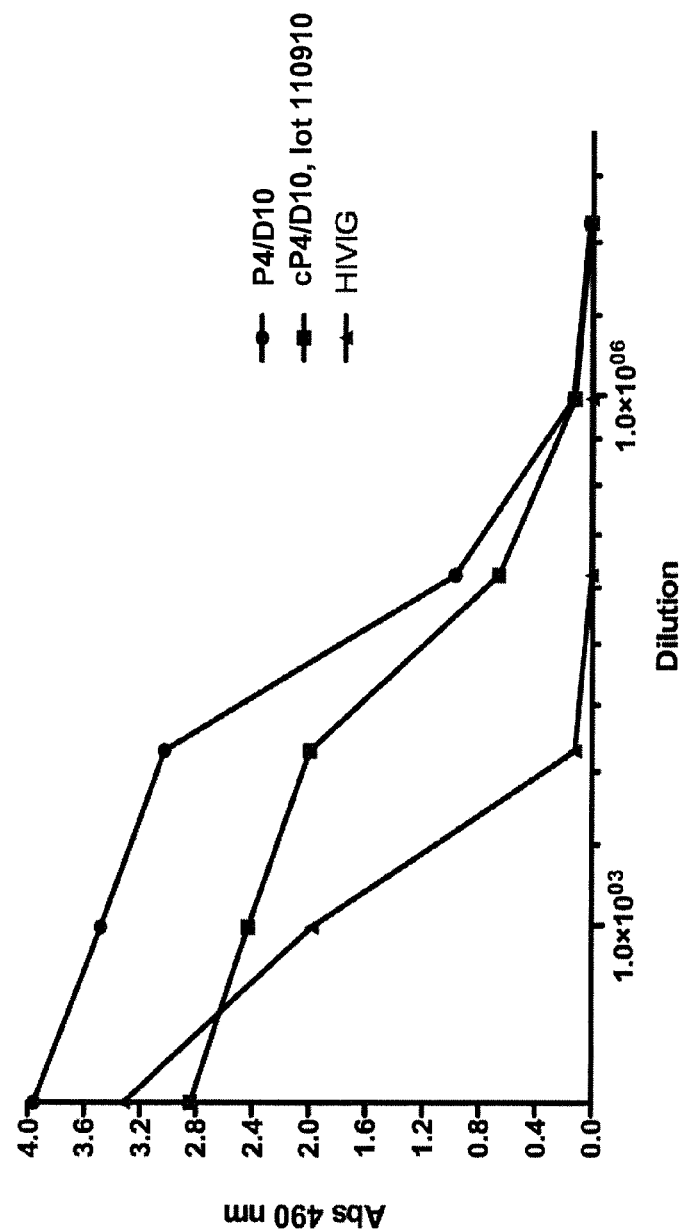
FIG. 10. Replotted data of T20 compound efficacy. The data of FIG. 9 were replotted to take into account the molecular weight of the different T20 compositions. The Y-axis is the same as FIG. 9. The X-axis shows nanomolar concentration of T20, taking into account the number of T20 moieties present in the DNL® construct and the DDD2 fusion protein.
Figure 10B:
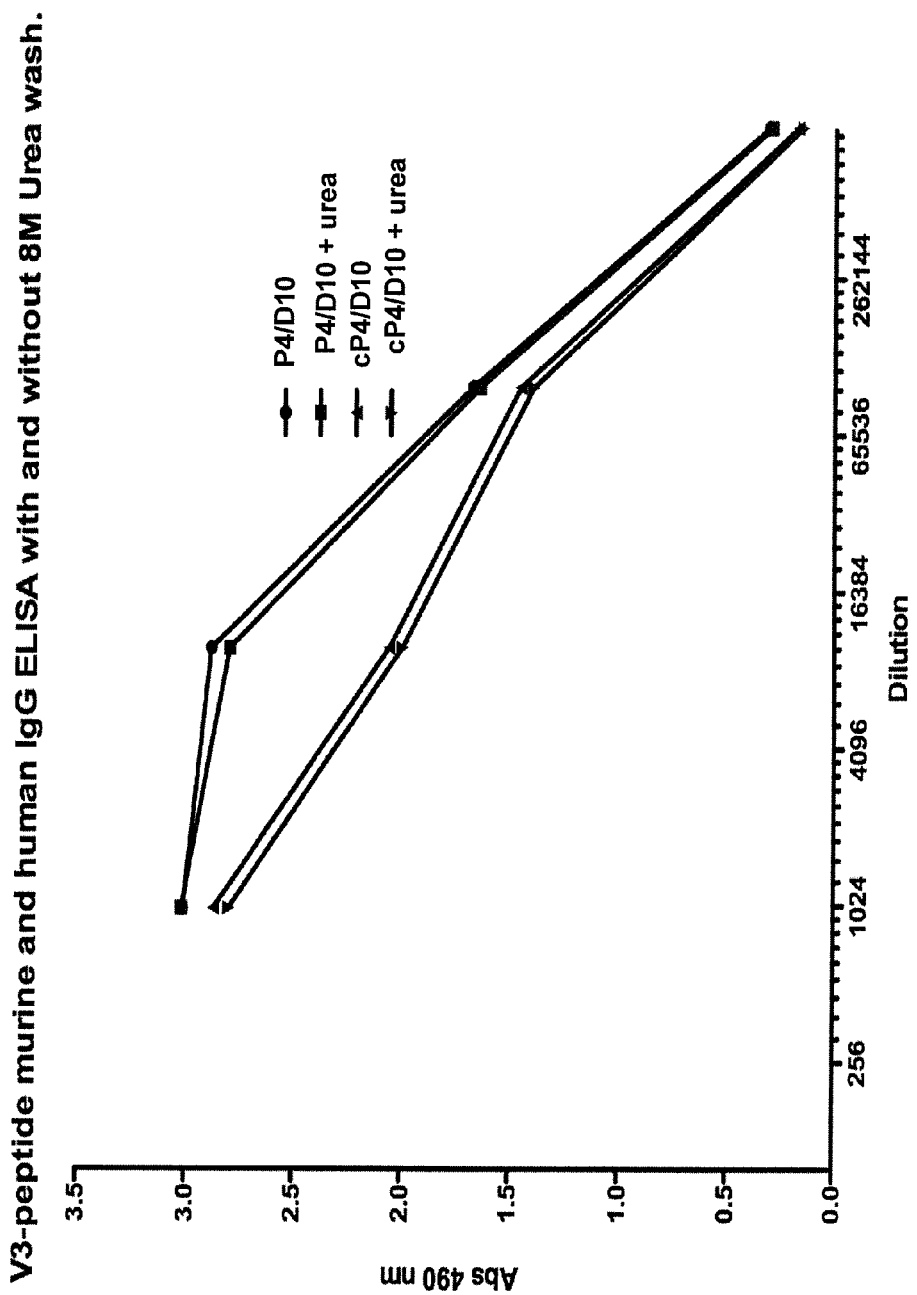
Figure 11A:
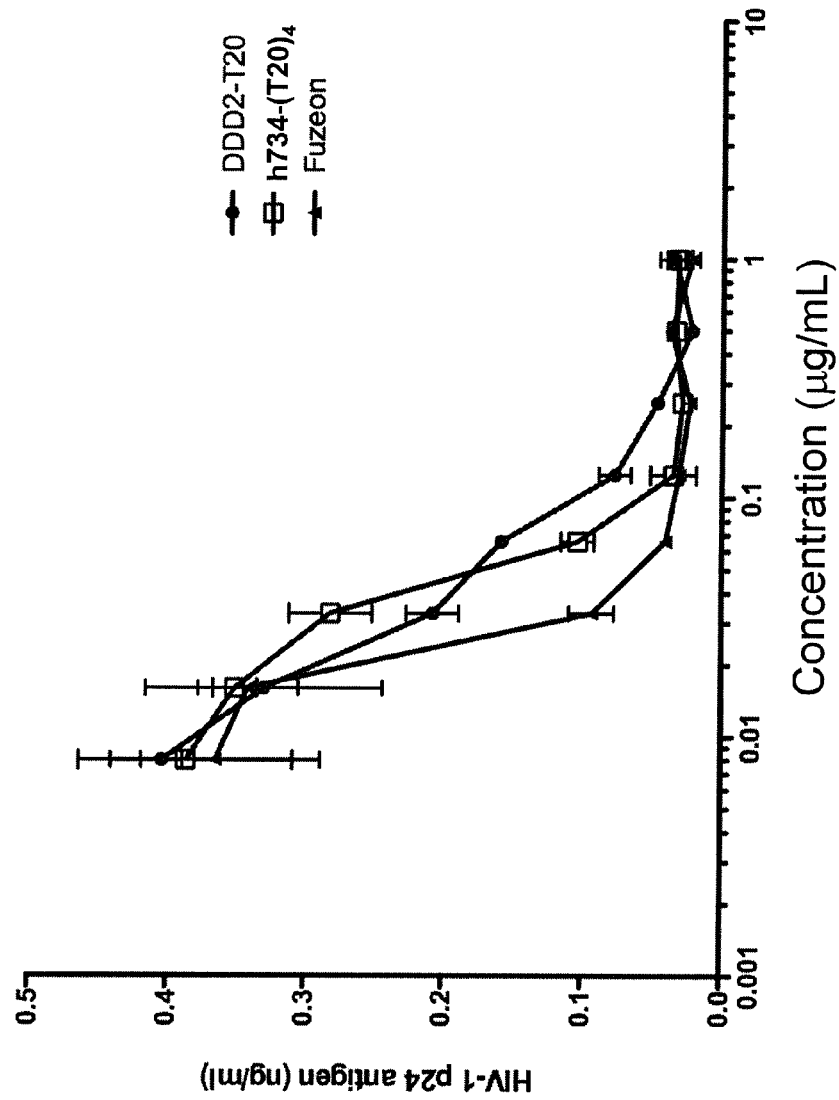
FIG. 11. Comparative potencies of anti-HIV fusion inhibitors. All data shown were determined with a PBMC/p24-based assay. Potency is dependent in part on the specific HIV-strains and clades tested. Data for T20 and 734-T20 was estimated from the experiment of FIG. 10. EP40111 was made by site-specific conjugation of T20 to an anti-thrombin binding pentasaccharide via a PEG-12 linker (Huet et al., 2010, Antimicrob Agents Chemother 54:134-42). Data for Fc-T20 was as reported by Syntonix. C34 is a T20 analog (Stoddart et al., 2008, J Biol Chem 283:34045-52). PC-1505 is a T20 analog made by site-specific conjugation of maleimido-C34 to HSA (at Cys34).
Figure 11B:
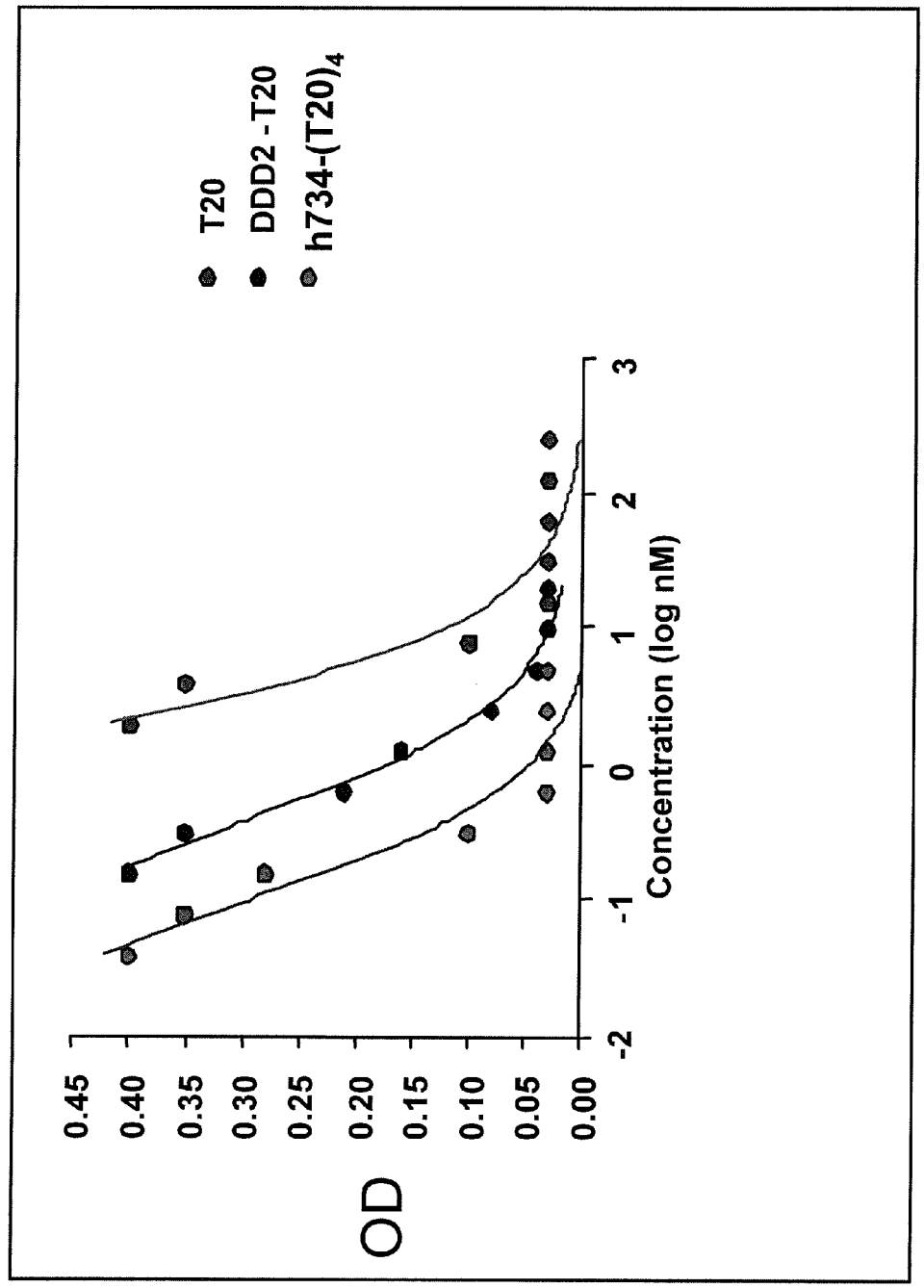
Figure 12A:
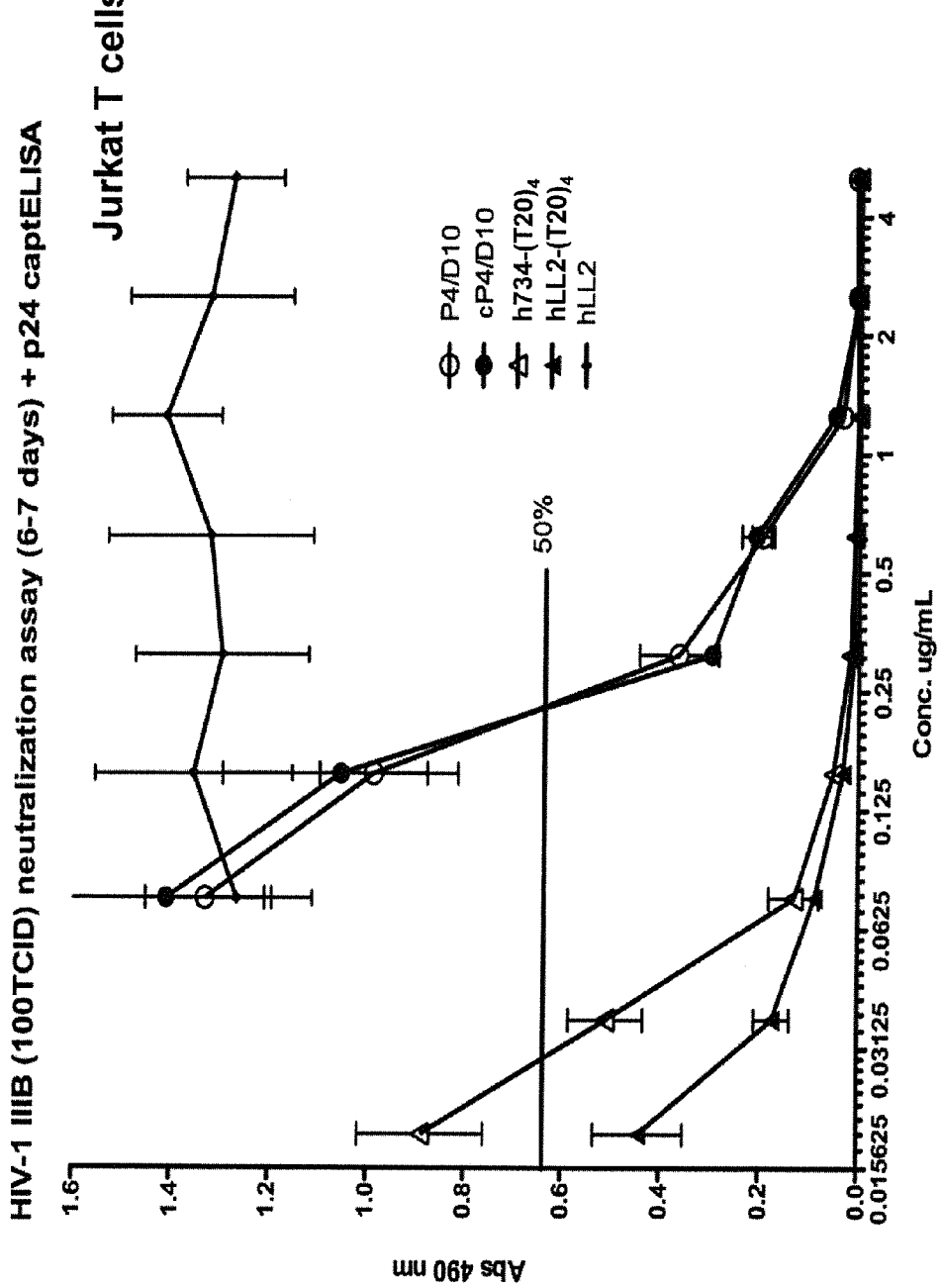
Figure 12B:
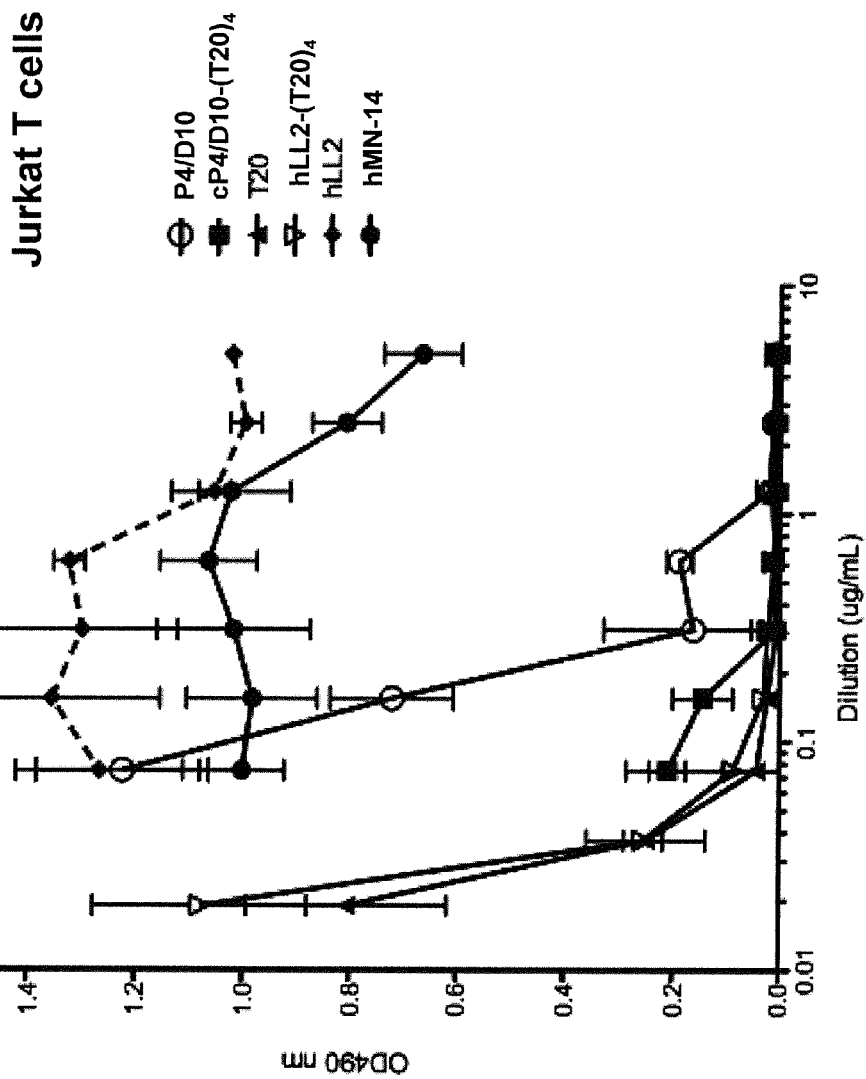
Figure 12D:
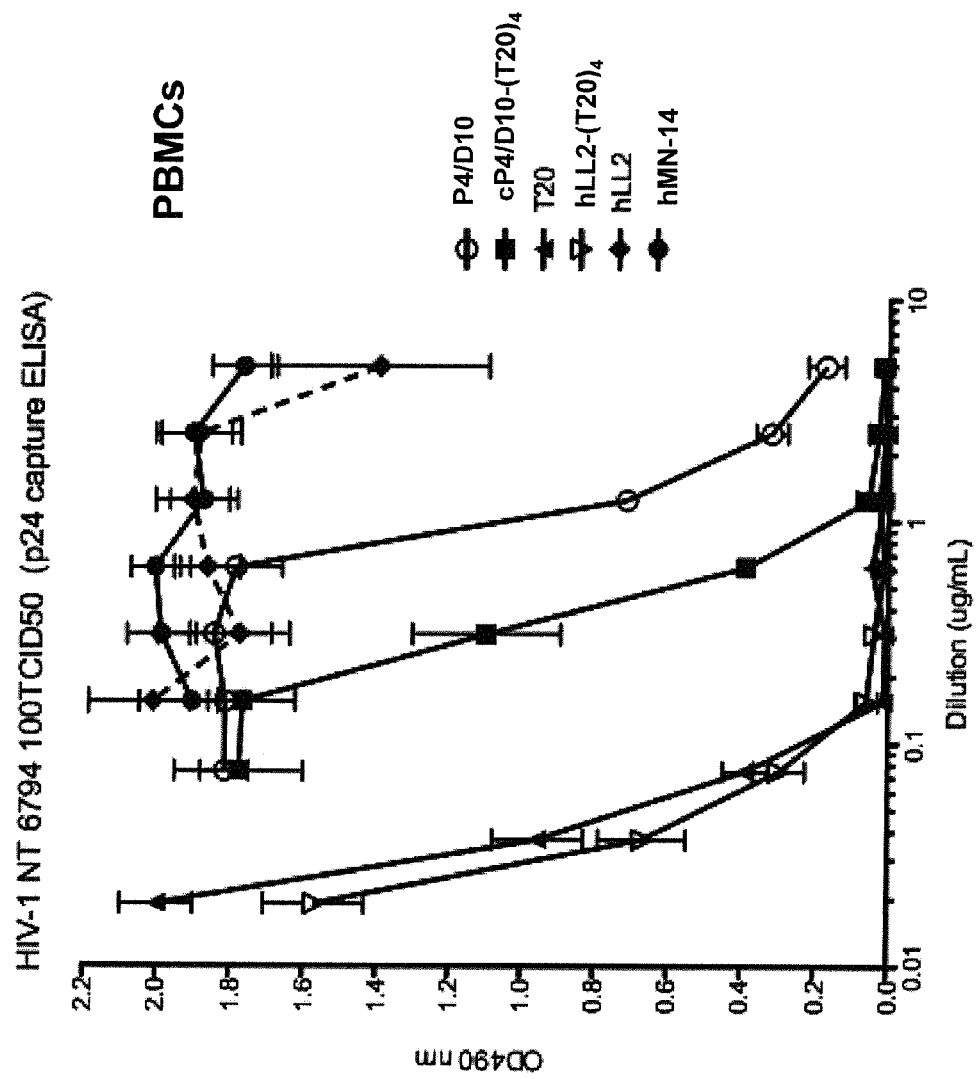
Figure 13A:
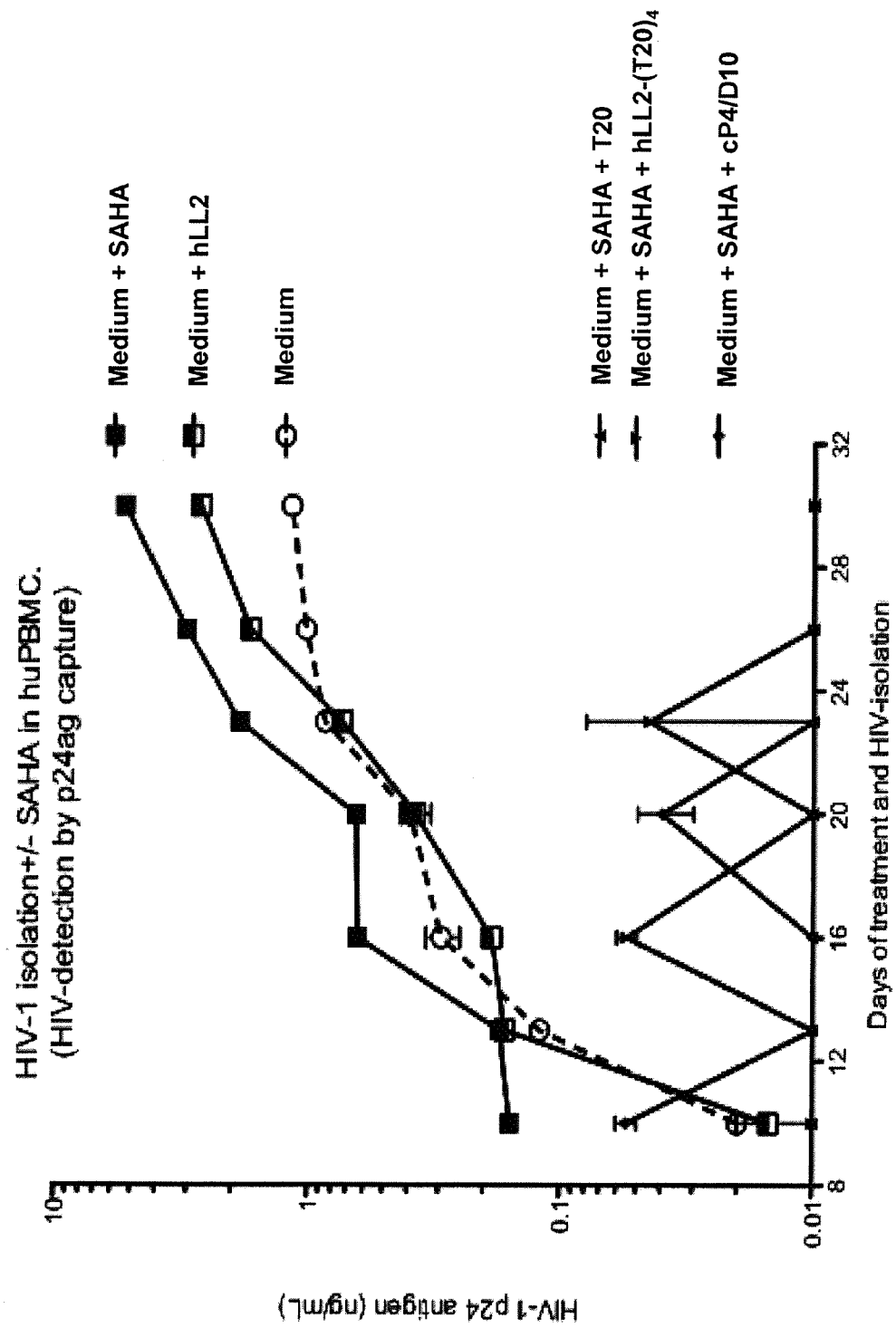
Figure 13B:
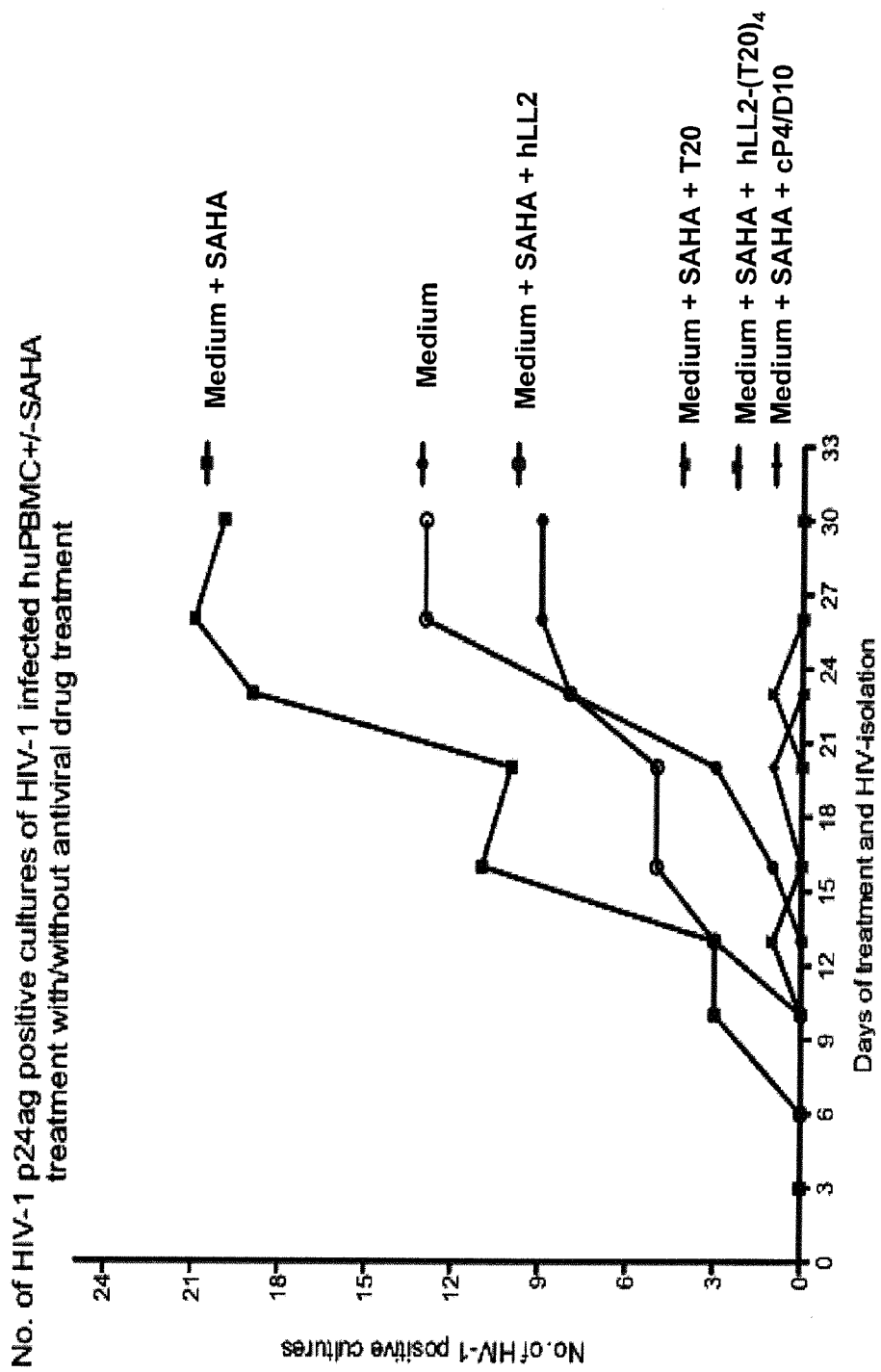
Figure 13C:
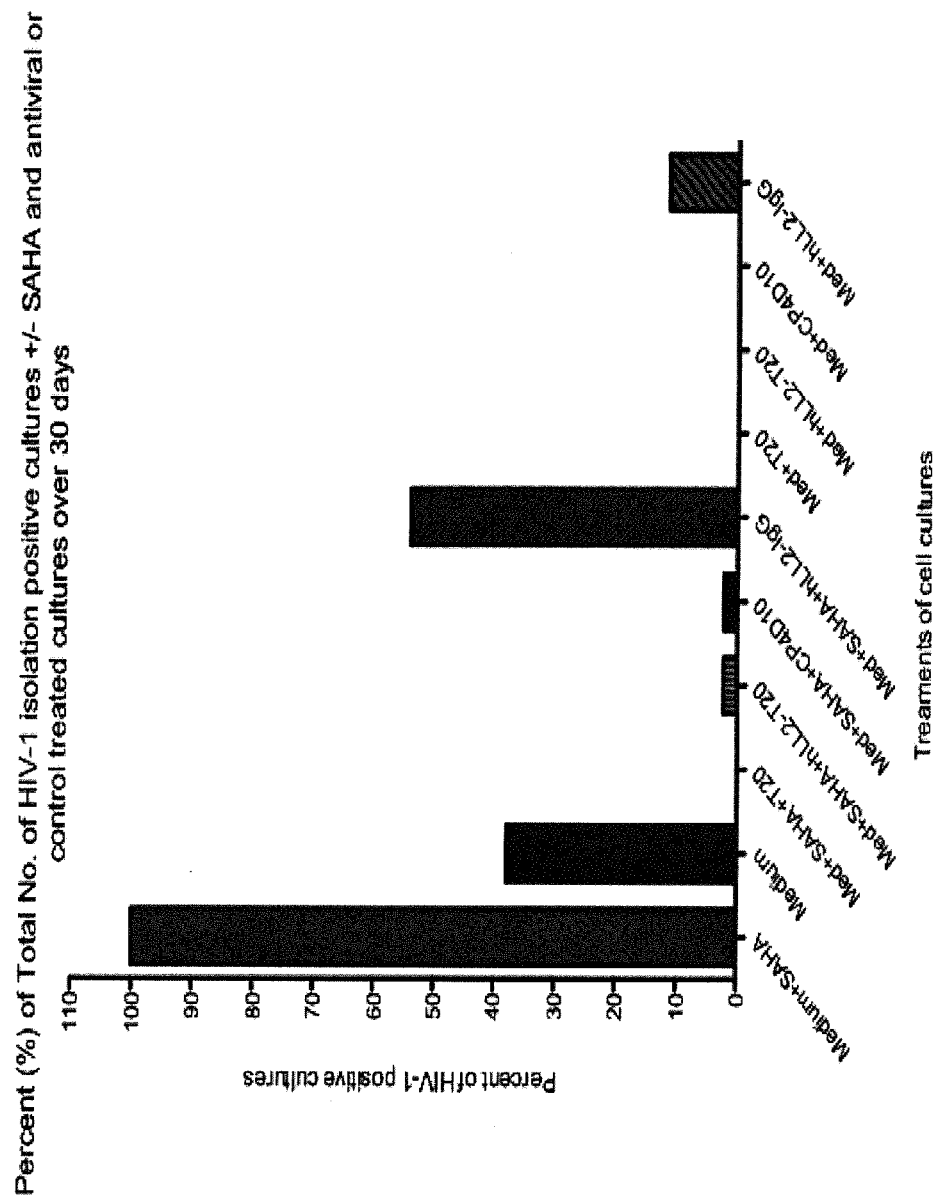
Figure 14:
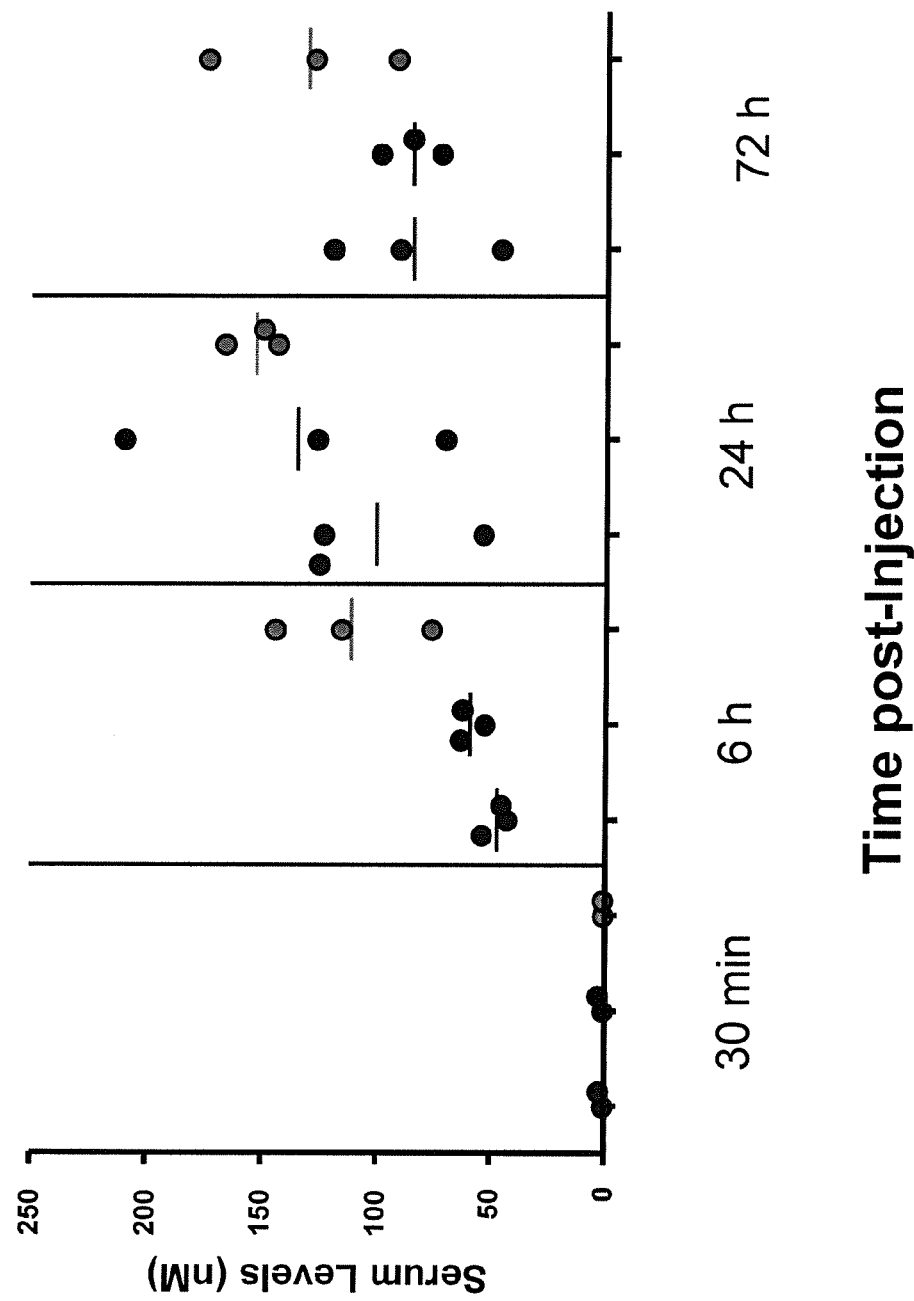

P4/D10 is a murine antibody that may induce human anti-mouse antibodies (HAMA) when administered to human subjects. Chimeric or humanized forms of P4/D10 would be more suitable for human therapeutic use. A chimeric P4/D10 (cP4/D10) was constructed by substituting human antibody constant region sequences for the murine constant region sequences of P4/D10. cP4/D10 was prepared and its binding affinity for gp160 (comprising both gp120 and gp41) was compared to the murine P4/D10 and a control non-targeting T4-2 (anti-CD4) antibody. The affinity (not shown) and in vitro activity (FIG. 7) of cP4/D10 were determined to be about two-fold lower than the parental P4/D10, which is acceptable and may be further improved by additional subcloning and humanization. Control non-targeting antibody did not bind to gp160.

In addition to anti-HIV antibodies, two humanized antibodies, h734 (anti-indium-DTPA) and hLL2 (epratuzumab; anti-CD22), are used as non-targeting controls. The HIV-targeting anti-gp120 murine P4/D10 is first chimerized (cP4/D10) and then humanized (hP4/D10). A second HIV-targeting antibody, 2G12 (Hessell et al., 2009, PLoS Pathogens 5:e1000433), which is already a human antibody and has a broader neutralizing activity than P4/D10, is also incorporated into a DNL® complex with T20. Other antibodies targeting both HIV-specific and cellular viral receptors (such as CD4 or CCR5) may be combined to increase efficacy and overcome virus variability and neutralizing antibody escape. The primary target HIV patient population is individuals failing HAART therapy, where several doses of the DNL® conjugates may effectively reduce the number of infected cells and circulating virions. A secondary patient population is individuals on effective HAART, with the goal to reach and delete the few persisting, virus-producing cells. Table 7 below lists exemplary T20-containing DNL® conjugates and their respective antibody component.

TABLE 7

Anti-HIV DNL® Complexes.

| DNL Complex | Antigen | Antibody | Advantages over Unconjugated T20 |
|---|---|---|---|
| h734-(T20) | Indium-DTPA | h734 | Improved PK |
| hLL2-(T20) | CD22 | hLL2 | Improved PK |
| hP4/D10-(T20) | gp120 (V3 loop) | hP4/D10 | Improved PK, neutralizing HIV, killing infected T cells |
| 2G12-(T20) | gp120 (oligo-mannose) | 2G12 | Improved PK, broadly neutralizing HIV |

In alternative embodiments, HIV therapeutic agents such as T20 are incorporated into DNL® constructs with PEG, as described in Example 6 above, to provide improved pharmacokinetic properties and decreased frequency of administration.

We have produced DDD2-T20 in *E. coli* and used the available non-targeting h734-IgG-AD2 and hLL2-IgG-AD2 antibodies to produce DNL® constructs that are not specific for HIV. Following reaction with DDD2-T20, the resulting h734-T20 conjugate was evaluated for in vitro activity by p24 ELISA, according to Johansson et al. (2006, AIDS 20:1911-15). FIG. 9 compares the relative potencies of the DDD2-T20 fusion protein, the non-targeting h734 IgG-T20 DNL® construct, and the unconjugated T20 (FUZEON®) in vitro, with concentration measured as μg/ml of T20-containing compound. As shown in FIG. 9, the DNL® construct and the DDD2-T20 fusion protein showed approximately equal efficacy with unconjugated T20 in this assay. However, because the molecular weight of the DNL® construct is significantly higher than the unconjugated T20, these results do not show equal efficacy on a molar basis.

When the results are replotted to account for the molecular weight of the different T20 constructs (FIG. 10), The T20-DDD2 construct was more efficacious than unconjugated T20 and the 734-T20 DNL® construct was more than an order of magnitude more efficacious than unconjugated T20. The relative potencies and Pk values of the T20 compounds are shown in FIG. 11. The 734-T20 construct exhibited an $EC_{50}$ of about 0.1 nM, compared to 1 to 2 nM for T20. The DNL® construct showed $EC_{90}$ of about 0.6 nM, compared to about 10 nM for T20. The DNL® construct also exhibited a significantly greater half-life in vivo, of about 24 hours compared to 2.8 hours for T20. These results show that even when a non-targeting antibody is used, DNL® complexes comprising T20 exhibit a substantially longer half-life in circulation and a substantially higher efficacy than unconjugated T20.

The X-axis of FIG. 10 shows the nanomolar concentration of T20, taking into account the four T20 moieties per DNL® construct. Thus, considered on the basis of the nanomolar concentration of the DNL® complex vs. unconjugated T20, the DNL® complex was 50-fold more potent than unconjugated T20. Because the 734 antibody does not target HIV-infected cells, it is expected that DNL® complexes comprising T20 attached to an anti-HIV antibody would be even more efficacious. The increased efficacy of 734-T20 compared to unconjugated T20 may result from more effective blocking of viral entry into cells by multiple binding of T20 moieties.

FIG. 11 also shows results obtained with a PEG-pentasaccharide conjugate of T20 (EP40111), which exhibited a longer half-life, but substantially decreased potency compared to unconjugated T20. C34 is a T20 analog that shows somewhat improved efficacy, but similar half-life compared to T20. PC-1505 is a human serum albumin conjugate of C34, with longer half-life but similar potency to T20.

The in vitro efficacy of the new agents is compared to parental constructs as well as applicable controls in seven different HIV strains (3 Glade B viruses, 1 each of Glade A, C, D and AE viruses), all available through WHO and NIBSC/NIH. A preclinical validation of the IgG-T20 conjugates is assessed in a mouse model of HIV-1 challenge, in which young murine spleen cells infected with pseudotyped HIV-1 through a phosphate ion channel are injected i.p. into young mice of the analogous strain C57BL that is transgenic for HLA-2. The resulting infectious virus is assessed by HIV culture from the peritoneum (Boberg et al., 2008, Vaccine 26:5079-82).

Antibodies with a broad and effective HIV neutralization activity are continuously being identified or engineered (Burton and Weiss, Science 2010; 329:770-3) and some of them may have superior properties. Additional antibodies, such as anti-CD4, and alternative HIV-inhibitors, such as next-generation fusion inhibitors, may also be used as components of the DNL® conjugates. Enhanced efficacy may also be achieved with the co-administration of unconjugated antibodies that are themselves effective in monotherapy.

Humanized and fully human mAbs targeting multiple glyco-epitopes of HIV carbohydrates and glycoproteins will effectively target HIV-infected cells and virions during passive immunization against early HIV-1 infection or HIV-1 during effective or failing HAART. The HIV-specific targeting will be further aided by a molecule inserting itself at the transmembrane region of HIV virions and/or infected cells. As a result, the DNL® conjugates of the present design should more selectively target the infected cells than non-infected cells.

The skilled artisan will realize that other antibodies and/or HIV therapeutic agents may be incorporated into DNL® constructs using the techniques described above. Examples of other HIV therapeutic agents include, but are not limited to, sCD4-D1-D2 (West et al., 2010, J Virol. 84:261-69), CP32M (He et al., PNAS 2008; 105:16332-7), IZN17 (Eckert and Kim, PNAS 2001; 98:11187-92), C34 (Stoddart et al., J Biol Chem 2008; 283:34045-52), T1144 (Dwyer et al., PNAS 2007; 104:12772-7), C52L (Deng et al., Biochemistry 2007; 46:4360-9), CCR5 antagonists such as maraviroc or vicriviroc; and agents such as abacavir, amdoxovir, AOP-RANTES, apricitabine, atazanavir, bevirimat, BMS-378806, calanolide A, CCR5, CD4, ceragenin, cobicistat, cyanovirin-N, darunavir, diarylpyrimidines, didanosine, dolutegravir, efavirenz, elvitegravir, elvucitabine, emtricitabine, epigallotachen gallate, festinavir, fosamprenavir, foscarnet, griffithsin, globoidnan A, hydroxycarbamide, indinavir, KP-146, lamivudine, lefinavir, lersivirine, lopinavir, miltefosine, MK-2048, nelfinavir, nevirapine, racivir, raltegravir, ritonavir, saquinavir, selicicib, stafudine, stampidine, stavudine, T61, T651, T1249, T2635, Tat antagonists, tenofovir, tipranavir, trichosanthin, TRIM5alpha, vivecon, zalcitabine, zidovudine or zidovudine. Such other anti-HIV therapeutic agents may be attached or incorporated into the DNL® complex, or may alternatively be co-administered to the subject before, concurrently with or after the DNL® complex.

Other antibodies of potential use include anti-CD4 antibodies such as ibalizumab (Bruno and Jacobson, 2010, J Antimicrob Chemother 65:1839-41), anti-Leu3a, L120, OKT4A, 13B8.2 or L71; anti-CCR5 antibodies such as NBP1-43335, ab10397, 2D7, HGS004, MC-1, MC-4, MC-5, PA9, PA14 or PRO140 (see, e.g., Lopalco, 2011, J Transl Med 9:S4); or neutralizing anti-HIV antibodies such as 2G12 (Armbruster et al., J. Antimicrob. Chemother. 54:915-20, 2004), 2F5 (Bryson et al., Protein and Peptide Letters, 8:413-18, 2001), 3D6 (Ruker et al., Ann. NY Acad. Sci. 646:212-19, 1991), b12 (e.g., Wu et al., *J Virol* 2006, 80:2585), X5 (Moulard et al., *Proc Natl Acad Sci* 2002, 99:6913-18), C37 (Cao et al., DNA and Cell Biology, 12:836-41, 2004), 1ACY, 1F58, 1GGGC (Berry et al., Proteins, 45:281-82, 2001) or 4E10 (Cardoso et al., 2005, Immunity 22:163-73). The skilled artisan will realize that DNL® complexes comprising any antibody or antigen-binding fragment thereof may be incorporated into a DNL® complex using the methods described herein.

Example 8

PEGylated Anti-HIV Agent DNL® Complex

A PEG-AD2 moiety is prepared as described in Example 6 above, selected from IMP362, IMP413 and IMP457. T20-DDD2 is prepared as described in Example 7 above. A DNL® complex is formed from the PEG-AD2 and T20-DDD2, comprising one PEG moiety attached to two T20 moieties. The PEGylated T20 DNL® complex shows comparable efficacy and over an order of magnitude higher serum half-life than unconjugated T20, allowing weekly instead of daily administration. A decreased incidence of injection site adverse reactions is observed with the DNL® complex compared to unconjugated T20.

Example 9

DNL® Complex with Humanized Anti-HIV Antibody

Chimeric P4/D10 antibody prepared as described in Example 7 above is used to prepare a humanized P4/D10 (hP4/D10), according to Leung et al. (1995, Mol. Immunol., 32: 1413), by attaching the murine CDR sequences to human antibody framework region (FR) and constant region sequences. The human antibody FR sequences are constructed using the same human IgG donor FRs as the humanized anti-CD22 antibody epratuzumab (Leung et al., Mol Immunol 1995; 32: 1413-1427). Specifically, FR1, FR2, and FR3 of the human EU antibody and FR4 of the human NEWM antibody are selected for the heavy chain and the FRs of the human REI antibody are selected for the light chain of the hP4/D10 antibody. As disclosed in U.S. Pat. No. 7,151, 164, key murine residues are retained in the FRs to maintain the binding specificity and affinity of hP4/D10 for gp120.

The Vκ sequence for the MAb is amplified using the primers VK1BACK and VK1FOR (Orlandi et al, 1989). The $V_H$ sequence is amplified using the primer pair VH1BACK/ VH1FOR (Orlandi et al., 1989). PCR reaction mixtures contain 10 µl of the first strand cDNA product, 10 µl of 10×PCR buffer [500 mM KCl, 100 mM Tris-HCl (pH 8.3), 15 mM $MgCl_2$, and 0.01% (w/v) gelatin](Perkin Elmer Cetus, Norwalk, Conn.), 250 µM of each dNTP, 200 nM of the primers, and 5 units of Taq DNA polymerase (Perkin Elmer Cetus) are subjected to 30 cycles of PCR. Each PCR cycle consists of denaturation at 94° C. for 1 min, annealing at 50° C. for 1.5 min, and polymerization at 72° C. for 1.5 min. Amplified Vκ and $V_H$ fragments are purified on 2% agarose (BioRad, Richmond, Calif.). The humanized V genes are constructed by a combination of long oligonucleotide template syntheses and PCR amplification as described by Leung et al. (Mol. Immunol., 32:1413 (1995)).

PCR products for Vκ are subcloned into a pBR327-based staging vector, VKpBR, that contains an Ig promoter, a signal peptide sequence and convenient restriction sites to facilitate in-frame ligation of the Vκ PCR products. PCR products for $V_H$ are subcloned into the pBluescript-based VHpBS. Individual clones containing the respective PCR products are sequenced by the method of Sanger et al. (Proc. Natl. Acad. Sci., USA, 74: 5463 (1977)).

Expression cassettes containing the Vκ and $V_H$ sequences, together with the promoter and signal peptide sequences, are excised from VKpBR and VHpBS, respectively, by double restriction digestion as HindIII-BamHI fragments. The Vκ and VH expression cassettes are assembled in the modified staging vectors, VKpBR2 and VHpBS2, excised as XbaI/ BamHI and XhoI/BamHI fragments, respectively, and subcloned into a single expression vector, pdHL2, as described by Gilles et al. (J. Immunol. Methods 125:191 (1989) and also shown in Losman et al., Cancer, 80:2660 (1997)). The expression vector is transfected into Sp-EEE, Sp-ESF or Sp-ESF-X mammalian host cells for expression and antibody production.

Antibodies are isolated from cell culture media as follows. Cells are grown as a 500 ml culture in roller bottles using HSFM. Cultures are centrifuged and the supernatant filtered through a 0.2 µl membrane. The filtered medium is passed through a protein A column. The resin is then washed with about 10 column volumes of PBS and protein A-bound antibody is eluted from the column with 0.1 M glycine buffer (pH 3.5) containing 10 mM EDTA. Peak fractions are pooled, dialyzed against PBS, and the antibody concentrated with a CENTRICON® 30 concentrator (Amicon, Beverly, Mass.).

Purified hP4/D10 is attached to AD2 moieties as described in Example 7 above. The CP32M fusion inhibitor peptide is attached to DDD2 and expressed as a fusion protein as described in Example 7 above. A DNL® complex comprising hP4/D10-AD2 attached to DDD2-CP32M is prepared as described for the 734-T20 DNL® complex in Example 7 above. The hP4/D10-CP32M DNL® complex shows significantly improved efficacy and equivalent serum half-life, compared to the 734-T20 DNL® complex.

Example 10

Use of Other Anti-HIV Antibodies for DNL® Complex Formation

The 2G12 anti-HIV antibody is purchased from Polymun Scientific (Vienna, Austria). An AD2-2G12 fusion protein is prepared as described in Example 7 above. DDD2-T20 is prepared as described in Example 7 above. A DNL® complex comprising 2G12-AD2 attached to DDD2-T20 is prepared as described for the 734-T20 DNL® complex in Example 7 above. The 2G12-T20 DNL® complex shows significantly improved efficacy and equivalent serum half-life, compared to the 734-T20 DNL® complex.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the methods described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of treating an HIV infection comprising administering to a subject a complex comprising:
   a) an antibody or antigen-binding fragment thereof that binds to an antigen gp120, conjugated to a protein kinase A protein (AKAP) anchoring domain (AD) moiety; and
   b) at least one anti-HIV therapeutic agent conjugated to a human protein kinase A (PKA) regulatory subunit dimerization and docking domain (DDD) moiety;
   wherein two copies of the DDD moiety bind to one copy of the AD moiety to form the complex.

2. The method according to claim 1, wherein the antibody or fragment thereof and AD moiety comprise a first fusion protein and the anti-HIV therapeutic agent and DDD moiety comprise a second fusion protein.

3. The method according to claim 1, wherein the anti-HIV therapeutic agent is not a protein or peptide and is covalently attached to DDD2.

4. The method according to claim 1, wherein the amino acid sequence of the AD moiety is selected from the group consisting of SEQ ID NO:3, SEQ ID NO:4, SEQ ID NO:7, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84 and SEQ ID NO:91.

5. The method according to claim 1, wherein the regulatory subunit is selected from the group consisting of RIα, RIβ, RIIα and RIIβ.

6. The method according to claim 1, wherein the amino acid sequence of the DDD moiety is selected from the group consisting of SEQ ID NO:1, SEQ ID NO:2, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:90 and SEQ ID NO:92.

7. The method of claim 1, further comprising administering to the subject at least one additional anti-HIV therapeutic agent.

8. The method of claim 7, wherein the subject is treated with HAART (highly active antiretroviral therapy).

9. The method of claim 1, wherein the antibody or fragment thereof is attached to two copies of the AD moiety and the complex comprises four copies of the DDD-conjugated therapeutic agent.

* * * * *

```
                              SEQUENCE LISTING

<160> NUMBER OF SEQ ID NOS: 105

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Gln Ile Glu Tyr Leu Ala Lys Gln Ile Val Asp Asn Ala Ile
1               5                   10                  15
```

```
Gln Gln Ala Gly Cys
        20

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Phe Glu Glu Leu Ala Trp Lys Ile Ala Lys Met Ile Trp Ser
1               5                   10                  15

Asp Val Phe Gln Gln Gly Cys
        20

<210> SEQ ID NO 8
<211> LENGTH: 51
<212> TYPE: PRT
<213> ORGANISM: Homo sapiens

<400> SEQUENCE: 8

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30
```

-continued

```
Arg Pro Met Ala Phe Leu Arg Glu Tyr Phe Glu Lys Leu Glu Lys Glu
            35                  40                  45

Glu Ala Lys
    50

<210> SEQ ID NO 9
<211> LENGTH: 54
<212> TYPE: PRT
<213> ORGANISM: Homo sapiens

<400> SEQUENCE: 9

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
            35                  40                  45

Asn Arg Gln Ile Leu Ala
    50

<210> SEQ ID NO 10
<211> LENGTH: 44
<212> TYPE: PRT
<213> ORGANISM: Homo sapiens

<400> SEQUENCE: 10

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
            35                  40

<210> SEQ ID NO 11
<211> LENGTH: 44
<212> TYPE: PRT
<213> ORGANISM: Homo sapiens

<400> SEQUENCE: 11

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
            35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
```

```
                35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30
```

Val Glu Tyr Phe Thr Arg Leu Arg Glu Ala Arg Ala
            35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala

```
            20                  25                  30

Val Glu Tyr Phe Thr Arg Leu Arg Glu Ala Arg Ala
        35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Gly Tyr
1               5                   10                  15
```

```
Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
            35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
            35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
            35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
            35                  40

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ile Glu Tyr Leu Ala Lys Gln Ile Val Asp Asn Ala Ile Gln Gln
1               5                   10                  15
```

```
<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Leu Glu Tyr Leu Ala Lys Gln Ile Val Asp Asn Ala Ile Gln Gln
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Glu Tyr Leu Ala Lys Gln Ile Val Asp Asn Ala Ile Gln Gln
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Asp Tyr Leu Ala Lys Gln Ile Val Asp Asn Ala Ile Gln Gln
1               5                   10                  15

Ala

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ile Glu Phe Leu Ala Lys Gln Ile Val Asp Asn Ala Ile Gln Gln
1               5                   10                  15

Ala

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ile Glu Thr Leu Ala Lys Gln Ile Val Asp Asn Ala Ile Gln Gln
```

```
1               5                   10                  15
Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Glu Ser Leu Ala Lys Gln Ile Val Asp Asn Ala Ile Gln Gln
1               5                   10                  15

Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Ile Ala Lys Gln Ile Val Asp Asn Ala Ile Gln Gln
1               5                   10                  15

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ile Glu Tyr Val Ala Lys Gln Ile Val Asp Asn Ala Ile Gln Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr Leu Ala Arg Gln Ile Val Asp Asn Ala Ile Gln Gln
1               5                   10                  15

Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

Gln Ile Glu Tyr Leu Ala Lys Asn Ile Val Asp Asn Ala Ile Gln Gln
1               5                   10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Val Glu Asn Ala Ile Gln Gln
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Tyr Leu Ala Lys Gln Ile Val Asp Gln Ala Ile Gln Gln
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ile Glu Tyr Leu Ala Lys Gln Ile Val Asp Asn Ala Ile Asn Gln
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Leu Ala Lys Gln Ile Val Asp Asn Ala Ile Gln Asn
1               5                   10                  15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Leu Ala Lys Gln Ile Val Asp Asn Ala Ile Gln Gln
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Leu Ala Lys Gln Ile Val Asp Asn Ala Ile Gln Gln
1               5                   10                  15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Lys Gln Ile Val Asp Asn Ala Ile Gln Gln
1               5                   10                  15

Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Val Ala Lys Gln Ile Val Asp Tyr Ala Ile His Gln
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Lys Ala Lys Gln Ile Val Asp His Ala Ile His Gln
1               5                   10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 52

Gln Ile Glu Tyr His Ala Lys Gln Ile Val Asp His Ala Ile His Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Val Ala Lys Gln Ile Val Asp His Ala Ile His Gln
1               5                   10                  15

Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Glu Glu Ala Ala Ser Arg Ile Val Asp Ala Val Ile Glu Gln
1               5                   10                  15

Val Lys

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 57

Ala Leu Tyr Gln Phe Ala Asp Arg Phe Ser Glu Leu Val Ile Ser Glu
1               5                   10                  15

Ala Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Gln Val Ala Asn Gln Leu Ala Asp Gln Ile Ile Lys Glu Ala
1               5                   10                  15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Glu Glu Leu Ala Trp Lys Ile Ala Lys Met Ile Trp Ser Asp Val
1               5                   10                  15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Val Arg Leu Ser Lys Arg Leu Val Glu Asn Ala Val Leu Lys
1               5                   10                  15

Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ala Glu Glu Val Ser Ala Arg Ile Val Gln Val Val Thr Ala Glu
1               5                   10                  15

Ala Val

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Gln Ile Lys Gln Ala Ala Phe Gln Leu Ile Ser Gln Val Ile Leu Glu
1               5                   10                  15

Ala Thr

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ala Trp Lys Ile Ala Lys Met Ile Val Ser Asp Val Met Gln Gln
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Glu Gln Tyr Ala Asn Gln Leu Ala Asp Gln Ile Ile Lys Glu Ala
1               5                   10                  15

Thr Glu

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Glu Glu Leu Ala Trp Lys Ile Ala Lys Met Ile Trp Ser Asp Val
1               5                   10                  15

Phe Gln Gln Cys
            20

<210> SEQ ID NO 67
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 67

Gln Ile Glu Tyr Leu Ala Lys Gln Ile Pro Asp Asn Ala Ile Gln Gln
1               5                   10                  15
Ala

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly Ala Asp Leu Ile Glu Glu Ala Ala Ser Arg Ile Val Asp Ala
1               5                   10                  15
Val Ile Glu Gln Val Lys Ala Ala Gly
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Gly Ala Asp Leu Ile Glu Glu Ala Ala Ser Arg Ile Pro Asp Ala
1               5                   10                  15
Pro Ile Glu Gln Val Lys Ala Ala Gly
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Val Glu Asn
1               5                   10                  15
Ala Val Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Thr Ser Lys Arg Leu Val Glu Asn
1               5                   10                  15
Ala Val Leu Lys Ala Val Gln Gln Tyr
            20                  25
```

```
<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Glu Gly Leu Asp Arg Asn Glu Glu Ile Lys Arg Ala Ala Phe Gln
```

```
                 1               5                  10                 15

Ile Ile Ser Gln Val Ile Ser Glu Ala
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Val Asp Asp Pro Leu Glu Tyr Gln Ala Gly Leu Leu Val Gln Asn
1               5                  10                  15

Ala Ile Gln Gln Ala Ile Ala Glu Gln
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Tyr Glu Thr Leu Leu Ile Glu Thr Ala Ser Ser Leu Val Lys Asn
1               5                  10                  15

Ala Ile Gln Leu Ser Ile Glu Gln Leu
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Glu Lys Gln Tyr Gln Glu Gln Leu Glu Glu Val Ala Lys Val
1               5                  10                  15

Ile Val Ser Met Ser Ile Ala Phe Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Thr Asp Glu Ala Gln Glu Glu Leu Ala Trp Lys Ile Ala Lys Met
1               5                  10                  15

Ile Val Ser Asp Ile Met Gln Gln Ala
            20                  25

<210> SEQ ID NO 81
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 81

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Lys Ser Cys
1

<210> SEQ ID NO 86
<211> LENGTH: 55
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Ser Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 87
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Ser Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agatctggcg cacctgaact cctg                                          24

<210> SEQ ID NO 89
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaattcggat cctttacccg gagacaggga gag                                33

<210> SEQ ID NO 90
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys, or Arg
```

-continued

```
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile, or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile, or Val
<220> FEATURE:
<221> NAME/KEY: MOD_RES
<222> LOCATION: (43)..(43)
```

```
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile, or Val

<400> SEQUENCE: 90

Xaa Xaa Ile Xaa Ile Pro Pro Xaa Leu Xaa Xaa Leu Leu Xaa Xaa Tyr
 1               5                  10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu, or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr, or Ser
<220> FEATURE:
<221> NAME/KEY: MOD_RES
<222> LOCATION: (5)..(5)
<223> OTHER INFORMATION: Leu, Ile, or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile, or Val

<400> SEQUENCE: 91

Xaa Xaa Xaa Xaa Xaa Ala Xaa Xaa Ile Val Xaa Xaa Ala Ile Xaa Xaa
 1               5                  10                  15

Xaa

<210> SEQ ID NO 92
```

```
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu, or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu, or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile, or Val
<220> FEATURE:
<221> NAME/KEY: MOD_RES
<222> LOCATION: (44)..(44)
<223> OTHER INFORMATION: Ala, Leu, Ile, or Val

<400> SEQUENCE: 92

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
            35                  40

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Cys(SS-tbu)
```

```
<400> SEQUENCE: 93

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Cys(SS-tbu)

<400> SEQUENCE: 94

Cys Gly Gln Ile Glu Tyr Leu Ala Lys Gln Ile Val Asp Asn Ala Ile
1               5                   10                  15

Gln Gln Ala Gly Cys Gly
            20

<210> SEQ ID NO 95
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-PEG3
<220> FEATURE:
<221> NAME/KEY: MOD_RES
<222> LOCATION: (2)..(2)
<223> OTHER INFORMATION: Cys(S-tbu)
<220> FEATURE:
<221> NAME/KEY: MOD_RES
<222> LOCATION: (22)..(22)
<223> OTHER INFORMATION: Cys(S-tbu)

<400> SEQUENCE: 95

Cys Cys Gly Gln Ile Glu Tyr Leu Ala Lys Gln Ile Val Asp Asn Ala
1               5                   10                  15

Ile Gln Gln Ala Gly Cys Gly
            20

<210> SEQ ID NO 96
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tctagacaca ggacctcatc atggccttga cctttgcttt actgg              45

<210> SEQ ID NO 97
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 97
ggatccatga tggtgatgat ggtgtgactt ttccttactt cttaaacttt cttgc      55

<210> SEQ ID NO 98
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Lys Ser His His His His His Gly Ser Gly Gly Gly Gly Ser Gly
1               5                   10                  15

Gly Gly Cys Gly His Ile Gln Ile Pro Pro Gly Leu Thr Glu Leu Leu
            20                  25                  30

Gln Gly Tyr Thr Val Glu Val Leu Arg Gln Gln Pro Pro Asp Leu Val
        35                  40                  45

Glu Phe Ala Val Glu Tyr Phe Thr Arg Leu Arg Glu Ala Arg Ala
    50                  55                  60

<210> SEQ ID NO 99
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Cys Gly His Ile Gln Ile Pro Pro Gly Leu Thr Glu Leu Leu Gln
1               5                   10                  15

Gly Tyr Thr Val Glu Val Leu Arg Gln Gln Pro Pro Asp Leu Val Glu
            20                  25                  30

Phe Ala Val Glu Tyr Phe Thr Arg Leu Arg Glu Ala Arg Ala Glu Phe
        35                  40                  45

Pro Lys Pro Ser Thr Pro Pro Gly Ser Ser Gly His His His His His
    50                  55                  60

His Gly Ser Tyr Thr Ser Leu Ile His Ser Leu Ile Glu Glu Ser Gln
65                  70                  75                  80

Asn Gln Gln Glu Lys Asn Glu Gln Glu Leu Leu Glu Leu Asp Lys Trp
                85                  90                  95

Ala Ser Leu Trp Asn Trp Phe
            100

<210> SEQ ID NO 100
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Ile Ser Phe Met His Trp Tyr Gln Gln Lys Leu Gly Gln Pro Pro
        35                  40                  45

Lys Leu Leu Ile Tyr Arg Ala Ser Asn Leu Glu Ser Gly Ile Pro Ala
            50                  55                  60

Arg Phe Ser Gly Ser Gly Ser Gly Thr Glu Phe Thr Leu Thr Ile Asn
 65                  70                  75                  80

Pro Val Glu Thr Asp Asp Val Ala Thr Tyr Tyr Cys Gln Gln Ser Asn
                 85                  90                  95

Lys Asp Pro Leu Thr Phe Gly Ala Gly Thr Lys Leu Gln Ile Lys Arg
             100                 105                 110

<210> SEQ ID NO 101
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Val Gln Leu Gln Glu Ser Gly Ala Glu Leu Ala Ser Pro Gly Ala Ser
 1               5                  10                  15

Val Thr Leu Ser Cys Lys Ala Ser Gly Tyr Thr Phe Thr Asp His Ile
            20                  25                  30

Met Asn Trp Lys Lys Arg Pro Gly Gln Gly Leu Glu Trp Ile Gly Arg
        35                  40                  45

Ile Phe Pro Val Ser Gly Glu Thr Asn Tyr Asn Gln Lys Phe Met Gly
 50                  55                  60

Lys Ala Thr Phe Ser Val Asp Ser Ser Ser Thr Val Ser Met Val Leu
 65                  70                  75                  80

Asn Ser Leu Thr Ser Glu Asp Pro Ala Val Tyr Tyr Cys Asp Leu Ile
                 85                  90                  95

Tyr Tyr Asp Tyr Glu Glu Asp Tyr Tyr Phe Asp Trp Gly Gln Gly Thr
             100                 105                 110

Thr Leu Thr Val Ser Ser
        115

<210> SEQ ID NO 102
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gacatccagc tcacccagtc cccagcctct ctggctgtgt ccctgggaca gagggccaca     60
atctcttgca gagctagcga gtccgtggac gattacggga ttagtttcat gcactggtat    120
cagcagaagc tgggccagcc ccctaaactg ctgatctacc gggccagtaa cctggaaagc    180
ggcattccag ctcgcttctc tggcagtgga agcgggaccg agtttaccct gacaatcaac    240
cccgtggaaa ctgacgatgt ggccacctac tattgtcagc agagcaacaa ggaccccctg    300
acatttggcg ctggaactaa gctgcagatc aagagg                             336

<210> SEQ ID NO 103
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Ile Ser Phe Met His Trp Tyr Gln Gln Lys Leu Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Gly Thr Glu Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Leu Thr Phe Gly Ala Gly Thr Lys Leu Gln Ile Lys Arg
            100                 105                 110

<210> SEQ ID NO 104
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
gtgcagctcc aggagtccgg agccgaactg gctagtccag gggccagcgt gacactgtcc        60
tgcaaggctt ctgggtacac tttcaccgat cacatcatga actgggtgaa gaaaaggcca       120
ggacagggac tggagtggat cggaagaatt tttcctgtgt ctggagaaac taactataat       180
cagaagttca tggaaaaagc caccttcagc gtggacagga gctcctctac tgtgagcatg       240
gtgctgaaca gcctgacctc tgaggacccc gccgtgtact attgtgacct gatctactat       300
gactacgagg aagattacta tttcgactat tgggggcagg gcaccacact gacagtgagt       360
agc                                                                     363

<210> SEQ ID NO 105
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Val Gln Leu Gln Glu Ser Gly Ala Glu Leu Ala Ser Pro Gly Ala Ser
1               5                   10                  15

Val Thr Leu Ser Cys Lys Ala Ser Gly Tyr Thr Phe Thr Asp His Ile
            20                  25                  30

Met Asn Trp Val Lys Lys Arg Pro Gly Gln Gly Leu Glu Trp Ile Gly
        35                  40                  45

Arg Ile Phe Pro Val Ser Gly Glu Thr Asn Tyr Asn Gln Lys Phe Met
    50                  55                  60

Gly Lys Ala Thr Phe Ser Val Asp Arg Ser Ser Ser Thr Val Ser Met
65                  70                  75                  80

Val Leu Asn Ser Leu Thr Ser Glu Asp Pro Ala Val Tyr Tyr Cys Asp
                85                  90                  95

```
Leu Ile Tyr Tyr Asp Tyr Glu Glu Asp Tyr Tyr Phe Asp Tyr Trp Gly
            100                 105                 110

Gln Gly Thr Thr Leu Thr Val Ser Ser
        115             120
```